US012691065B2

(12) United States Patent
Liu et al.

(10) Patent No.: US 12,691,065 B2
(45) Date of Patent: Jul. 28, 2026

(54) LIPOSOME FORMULATIONS FOR TREATMENT OF CANCERS AND DRUG RESISTANCE OF CANCERS

(71) Applicant: NanoTech Pharma Inc., Hillsborough, NJ (US)

(72) Inventors: Fang Liu, Flemington, NJ (US); Xian Xu, Monmouth Junction, NJ (US)

(73) Assignee: NanoTech Pharma Inc., Hillsborough, NJ (US)

( * ) Notice: Subject to any disclaimer, the term of this patent is extended or adjusted under 35 U.S.C. 154(b) by 753 days.

(21) Appl. No.: 17/998,063

(22) PCT Filed: May 6, 2021

(86) PCT No.: PCT/US2021/031142

§ 371 (c)(1),
(2) Date: Nov. 7, 2022

(87) PCT Pub. No.: WO2021/226368

PCT Pub. Date: Nov. 11, 2021

(65) Prior Publication Data

US 2023/0172856 A1      Jun. 8, 2023

Related U.S. Application Data

(60) Provisional application No. 63/020,845, filed on May 6, 2020.

(51) Int. Cl.

| | |
|---|---|
| *A61K 9/127* | (2025.01) |
| *A61K 9/08* | (2006.01) |
| *A61K 9/1273* | (2025.01) |
| *A61K 9/1277* | (2025.01) |
| *A61K 9/1278* | (2025.01) |
| *A61K 31/404* | (2006.01) |
| *A61K 31/506* | (2006.01) |
| *A61K 31/704* | (2006.01) |
| *A61K 31/7068* | (2006.01) |
| *A61K 47/02* | (2006.01) |
| *A61K 47/24* | (2006.01) |
| *A61K 47/26* | (2006.01) |
| *A61K 47/40* | (2006.01) |
| *A61P 1/00* | (2006.01) |
| *A61P 11/00* | (2006.01) |
| *A61P 17/00* | (2006.01) |
| *A61P 19/00* | (2006.01) |
| *A61P 35/00* | (2006.01) |

(52) U.S. Cl.
CPC .............. *A61K 9/127* (2013.01); *A61K 9/08* (2013.01); *A61K 9/1273* (2013.01); *A61K 9/1277* (2013.01); *A61K 9/1278* (2013.01); *A61K 31/404* (2013.01); *A61K 31/506* (2013.01); *A61K 31/704* (2013.01); *A61K 31/7068* (2013.01); *A61K 47/02* (2013.01); *A61K 47/24* (2013.01); *A61K 47/26* (2013.01);

*A61K 47/40* (2013.01); *A61P 1/00* (2018.01); *A61P 11/00* (2018.01); *A61P 17/00* (2018.01); *A61P 19/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 2014/0356416 A1 | 12/2014 | Kesari et al. | |
| 2016/0256387 A1 | 9/2016 | Zhu et al. | |
| 2018/0098945 A1 | 4/2018 | Nel et al. | |
| 2020/0016079 A1 | 1/2020 | Kasagi et al. | |

FOREIGN PATENT DOCUMENTS

| | | |
|---|---|---|
| CN | 106999419 A | 8/2017 |
| CN | 107530291 A | 1/2018 |
| CN | 110505869 A | 11/2019 |
| WO | 2016022549 A1 | 2/2016 |
| WO | 2018181963 A1 | 10/2018 |
| WO | 2018218208 A1 | 11/2018 |

OTHER PUBLICATIONS

Chou, T.C., Derivation and Properties of Michaelis-Menten Type and Hill Type Equations for Referencere Ligands, J. Theor. Biol. (1976) 39:253-276.

Chou, T.C., et al., Quantative Analysis of Dose-Effect Relationships: The Combined Effects of Multiple Drugs or Enzyme Inhibitors, Talalay Adv. Enzyme Reg. (1984), 22:27-55.

ChunLei, L. et al., Novel sulfobutyl ether cyclodextrin gradient leads to highly active liposomal irinotecan formulation, Journal of Pharmacy and Pharmacology, vol. 63 No. 6, pp. 765-773.

Cobleigh, M., Other Options in the Treatment of Advanced Breast Cancer, (2011). Semin. Oncol., 38, Suppl 2: S11-16.

Cui, J. et al., Development of Pegylated Liposomal Vincristine Using Novel Sulfobutyl Ether Cyclodextrin Gradient: Is Improved Drug Retention Sufficient to Surpass DSPE-PEG-Induced Drug Leakage?, Journal of Pharmaceutical Sciences, vol. 100 No. 7, pp. 2835-2848.

Gupta, B., et al., Development of Bioactive PEGylated Nanostructured Platforms for Sequential Delivery of Doxorubicin and Imatinib to Overcome Drug Resistance in Metastatic Tumors, ACS Appl. Mater. Interfaces, vol. 9 No. 11, pp. 9280-9290.

(Continued)

*Primary Examiner* — Nannette Holloman
(74) *Attorney, Agent, or Firm* — Fox Rothschild LLP

(57) ABSTRACT

Disclosed herein are liposomal pharmaceutical compositions encapsulating one or more anticancer agents and methods of using the liposomal pharmaceutical compositions for treating cancers, in which multiple anticancer agents can be administered to a cancer patient in a synergistic molar ratio through liposome delivery particles. Methods of preparing the liposomes encapsulating multiple anticancer agents and the pharmaceutical compositions thereof are also disclosed.

22 Claims, 14 Drawing Sheets

(56) References Cited

OTHER PUBLICATIONS

Mamot, C., et al., Liposome-based approaches to overcome anti-cancer drug resistance, Drug Resist. Updates 2003, 6, 271-279.

Markman, J. L., et al., Nanomedicine therapeutic approaches to overcome cancer drug resistance, Adv. Drug Delivery Rev. 2013, 65, 1866-1879.

Maurel J., et al., Imatinib Plus Low-Dose Doxorubicin in Patients with Advanced Gastrointestinal Stromal Tumors Refractory to High-Dose Imatinib, Cancer. 2010, 116(15):3692-3701.

Mayer, L., et al., CPX-351: a nanoscale liposomal co-formulation of daunorubicin and cytarabine with unique biodistribution and tumor cell uptake properties, International Journal of Nanomedicine 2019:14, 3819-3830.

Michaelson, M.D., et al., Phase 2 Trial of Sunitinib and Gemcitabine in Patients with Sarcomatoid and/or Poor-Risk Metastatic Renal Cell Carcinoma, Cancer, 2015, 121(19):3435-43.

Peng, Y., Study on Folate Receptor-Targeted Imatinib Liposomes and Doxorubicin-Imatinib Liposome Complex, Full Text Database of Chinese Doctoral Dissertations in Science and Technology (Medical and Health Science Edition), vol. 07, pp. E079-16.

Shi., Y., et al., Mechanisms and management of doxorubicin cardiotoxicity (2011). Herz 36: 296-305.

Sims, J. T., et al., Imatinib Reverses Doxorubicin Resistance by Affecting Activation of STAT3-Dependent NFkB and HSP27/p38/AKT Pathways and by Inhibiting ABCB1, PLOS One 2013, 8, e55509.

International Search Report and Written Opinion for International Application No. PCT/US21/31142, filed May 6, 2021, mailed Sep. 8, 2021.

A     Pegylated liposome

B     DSPG liposome

A: Doxorubicin Hydrochloride

B: Imatinib Mesylate

C: Sunitinib Malate

D: Gemcitabine Hydrochloride

LIPOSOME FORMULATIONS FOR TREATMENT OF CANCERS AND DRUG RESISTANCE OF CANCERS

CROSS-REFERENCE TO RELATED APPLICATIONS

This application is a U.S. national phase application of International Application No. PCT/US2021/031142, filed on May 6, 2021, which claims priority under 35 U.S.C. § 119(e) to U.S. Provisional Patent Application No. 63/020,845, filed on May 6, 2020, the disclosures of which are incorporated herein by reference in their entirety.

FIELD OF THE INVENTION

The present invention relates to liposome-based pharmaceutical formulations, methods of encapsulating two or more active pharmaceutical ingredients (APIs), in particular anticancer agents, in the liposome core compartment, and methods of using the pharmaceutical formulations for the treatment of cancers, especially various drug-resistant cancers.

BACKGROUND OF THE INVENTION

Resistance to cancer chemotherapy is a common problem especially in the metastatic stage after patients typically have had exposure to multiple lines of prior therapies. Due to the development of drug resistance, patients can experience a rapid disease progression during or shortly after the completion of treatment. This resistance results in a limit number of treatment choices. Therefore, to minimize the impact of drug resistance, concurrent combined use of two or more anticancer drugs with unrelated mechanisms of action and differing modes of drug resistance has been attempted. The rationale for employing combination drug therapy is synergistic drug interaction. First, when multiple drugs with different molecular targets are applied, the cancer adaptation process such as cancer cell mutations can be delayed. Second, when multiple drugs target the same cellular pathway, they could function synergistically for higher therapeutic efficacy and higher target selectivity. Currently available combination regimens for multiple cancers in clinical studies are very much limited to administrating a physical mixture of two or more anticancer agents. The common clinically used combination regimens in clinical studies can be generally classified based on their mechanisms of action, including: (1) combination of nonspecific small molecule chemotherapeutic agents, (2) combination of target-specific receptor agents and chemotherapeutic agents, and (3) combination of target-specific receptor agents.

For the combination of chemotherapeutic agents with target-specific receptor agents, the chemotherapeutic agents lack cancer cell-specific targeting ability and also affect the fast-dividing normal cells of the body. Therefore, the major adverse effects from these chemotherapeutic agents are nonspecific toxicities including anemia, nausea, vomiting, and hair loss. The target-specific receptor agents (or target-cancer inhibitors) are advantageous to chemotherapy in their ability to actively target-specific receptors. Conventional chemotherapy does not discriminate effectively between tumor cells and rapidly dividing normal cells thus leading to nonspecific adverse effects. In contrast, target-specific anticancer therapies interfere with molecular targets that have an important role in tumor growth or progression distinct from normal cells. In addition, some of these agents act as inhibitors to multiple drug resistance (MDR) related proteins, thereby increasing the response rate. Overall targeted therapies provide a broader therapeutic window with less toxicity and higher response rate compared to conventional chemotherapy. Targeted therapies are often used in combination with chemotherapy and/or radiation to produce additive or even synergistic effects with a unique mechanism of action as compared to traditional cytotoxic therapy.

During the past years, combination chemotherapy has been widely exploited for enhanced cancer treatment in clinic. However, the traditional cocktail administration of combination regimens often suffers from varying pharmacokinetics among different drugs. In the common preclinical and clinical practices, the combined drug therapy was administrated singularly with various amounts and/or at different dosing schedules without pharmaceutical preparations designed to control delivery or half-lives of the drugs. These administration methods have various drawbacks that limit the therapeutic use of the combined drug treatment. Typically, the components of such regimens are first developed individually, without consideration of the many issues that may arise when they are used in combination, such as on-target antagonism and potentiation of adverse events. Although beneficial therapeutic effectiveness from combination treatment is promising when considering the theoretically nonoverlapping mechanisms of action of each anticancer drug, the above common combination in clinical cancer treatment is far from perfect, typically with moderate enhanced efficacy and additive toxicity. Therefore, novel approaches are investigated by incorporating nanotechnology with combination anticancer treatment. This promising hypothesis is that by delivering two or more drugs simultaneously using a carrier-mediated drug delivery system, the combination system can generate synergistic anticancer effects, reduce individual drug related toxicity, control release, and unify the pharmacokinetics of each drug. Popular investigated carriers for multiple drug delivery such as liposomes, dendrimers, polymeric nanoparticles, and water-soluble polymer-drug conjugates have been conducted in recently years. (Markman, J. L., et al., Adv. Drug Delivery Rev. 2013, 65, 1866-1879.)

In recent years, the lipid-based nanocarriers have demonstrated excellent outcomes by overcoming P-gp mediated efflux, sequestering drugs at tumor sites via enhanced permeability and retention (EPR), and escaping endosomal clearance once internalized. For example, CPX-351 (Vyxeos) is a dual-drug liposomal encapsulation of cytarabine and daunorubicin that was rationally designed to improve efficacy over the traditional 7+3 cytarabine/daunorubicin chemotherapy regimen for patients with acute myeloid leukemia (AML) (Lawrence D Mayer, et al., International Journal of Nanomedicine 2019:14, 3819-3830). To fulfill effective delivery of multiple drugs, some drugs have been attempted to be encapsulated in the liposome delivery vehicle, which is designed to shield them from mechanisms that would otherwise result in their clearance from the bloodstream. However, innovative combined anticancer drug liposome formulation development is still much needed to improve drug delivery specificity, enhance the drug therapeutic index, and thereby reduce the drug-related adverse effects.

SUMMARY OF THE INVENTION

The invention relates to methods of administering effective amounts of chemotherapeutic agent and protein kinase inhibitor (e.g., doxorubicin, daunorubicin, idarubicin, vinorelbine, irinotecan, topotecan, or gemcitabine with imatinib, sunitinib, nintedanib, ponatinib, afatinib, ruxolitinib, or others) drug combinations using liposomal delivery system, in which at least one chemotherapeutic agent and one protein kinase inhibitor drug are encapsulated. These compositions allow the two or more agents to be delivered to the disease site in a coordinated fashion, thereby ensuring that the agents will be present at the disease site at a desired ratio. This result would be achieved whether the agents are co-encapsulated in a lipid-based delivery vehicle or are encapsulated in a separate lipid-based delivery vehicle administered such that desired ratios are maintained at the disease site. The pharmacokinetics (PK) of the composition are controlled by the lipid-based delivery vehicle themselves such that coordinated delivery is achieved (provided that the PK of the delivery systems are comparable).

In one aspect, the present disclosure provides a pharmaceutical composition comprising liposomes suspended in a liquid medium, wherein the liquid medium comprises water and a pH buffer agent; wherein the liposome comprises an interior compartment surrounded by an outer lipid bilayer membrane, wherein the interior compartment comprises a protein kinase inhibitor, or preferably a combination of a hydrophilic chemotherapeutic agent and a protein kinase inhibitor, in an aqueous medium; wherein the lipid bilayer membrane comprises a hydrophilic inner surface forming the interior compartment, a lipophilic bilayer, and a hydrophilic outer surface in contact with the liquid medium of the composition; and wherein the hydrophilic chemotherapeutic agent and protein kinase inhibitor can be released from the liposomess in a synergistic mode.

In another aspect, the present disclosure provides a pharmaceutical composition according to any embodiments disclosed herein for use in the treatment of a cancer or drug resistance of a cancer in a subject in need of treatment, wherein the cancer is optionally selected from the group consisting of breast cancer, melanoma, gastrointestinal cancer, lung cancer, colorectal cancer, Ewing sarcoma, pancreatic cancer, prostate cancer, bladder cancer, kidney cancer, thyroid cancer, uterine cancer, and gastrointestinal stromal tumors, wherein the chemotherapeutic agent and protein kinase inhibitor can be delivered by the liposome with a synergistic cytotoxic or cytostatic effect on cancer cells.

In another aspect, the present disclosure provides a method of treating a cancer or drug resistance of a cancer, comprising administering to a subject in need of treatment a therapeutically effective amount of a pharmaceutical composition according to any embodiments disclosed herein.

In another aspect, the present disclosure provides a method of preparing a liposomal pharmaceutical composition (e.g., according to any one of claims 1 to 11), wherein the liposome is made by a process comprising the steps of:

In another aspect, the present invention provides liposomes as disclosed in any embodiments examples herein and/or prepared by a method according to any embodiments or examples disclosed herein.

In another aspect, the present invention provides a treatment kit comprising a container and a plurality of the drug-loaded liposomes according to any embodiments disclosed herein in the container, wherein the drug-loaded liposomes are or can be suspended in a sterile diluent solution ready for administration to a subject in need of treatment.

Thus, in some embodiments, the invention provides a liposome composition for parenteral administration comprising at least one chemotherapeutic agent and one protein kinase inhibitor (sometimes preferably a tyrosine kinase inhibitor) encapsulated in the liposomes at therapeutically effective ratios, especially those that are non-antagonistic. The therapeutically effective non-antagonistic ratio of the agents is determined by assessing the biological activity or effects of the agents on relevant cell culture and tumor homogenates from individual patient biopsies, over a range of concentrations. Also, frequently, combination is provided comprising imatinib or sunitinib (or another protein kinase inhibitors) and an anthracycline comprising doxorubicin, daunorubicin, idarubicin, or among other known chemotherapeutic agents. Any method which results in determination of a ratio of agents which maintains a desired therapeutic effect may be used.

The composition comprises at least one chemotherapeutic agent and one protein kinase inhibitor in a molar ratio of the chemotherapeutic agent to the protein kinase inhibitor agent which exhibits a desired biologic effect to relevant cells in culture and tumor homogenates. Preferably, the ratio is that at which the agents are non-antagonistic.

In some embodiments, the invention is directed to a method to deliver a therapeutically effective amount of an chemotherapeutic agent/protein kinase inhibitor combination (e.g., doxorubicin and imatinib or sunitinib) to a desired target by administering the compositions of the invention.

The invention is also directed to a method to deliver a therapeutically effective amount of the combination of a chemotherapeutic agent and a protein kinase inhibitor by administering a chemotherapeutic agent stably associated with a first delivery vehicle and a protein kinase inhibitor stably associated with a second delivery vehicle. The first and second delivery vehicles may be contained in separate vials, the contents of the vials being administered to a patient simultaneously or sequentially. In one embodiment, the ratio of the chemotherapeutic agent and the protein kinase inhibitor is non-antagonistic.

In some embodiments, the cancer is selected from the group consisting of breast cancer, melanoma, gastrointestinal cancer, lung cancer, colorectal cancer, Ewing sarcoma, pancreatic cancer, prostate cancer, bladder cancer, kidney cancer, thyroid cancer, uterine cancer, and gastrointestinal stromal tumors.

In some embodiments, sometimes preferably, the breast cancer is triple negative breast cancer, and wherein the lung cancer is caused by either a high level of phosphorylation of a wild-type EGFR or a mutation within an EGFR amino acid sequence.

In some embodiments, the invention is directed to a method to prepare a therapeutic composition comprising liposomes containing a ratio of at least one chemotherapeutic agent and one protein kinase inhibitor which provides a desired therapeutic effect. The method comprises: (a) providing a panel of at least one chemotherapeutic agent and one protein kinase inhibitor, wherein the panel comprises at least one, but preferably a multiplicity of ratios of said drugs; (b) testing the ability of the members of the panel to exert a biological effect on a relevant cell culture or tumor homogenate over a range of concentrations; (c) selecting a member of the panel wherein the ratio provides a desired therapeutic effect on the cell culture tumor homogenate over a suitable range of concentrations; and (d) stably associating the ratio of drugs represented by the successful member of the panel into lipid-based drug delivery vehicles. In preferred embodiments, the abovementioned desired therapeutic effect is non-antagonistic.

As further described below, in a preferred embodiment, in designing an appropriate combination in accordance with the method described above, the non-antagonistic ratios are selected as those that have a combination index (CI)≤1.1

(equal or smaller than 1.1). In further embodiments, suitable liposomal formulations are designed such that they stably incorporate an effective amount of a chemotherapeutic agent and a protein kinase inhibitor combination and allow for the sustained release of both drugs in vivo. Preferred formulations contain mPEG-DSPE or at least one negatively charged lipid, such as phosphatidylglycerol.

Liposomes can be prepared with active drug loading and/or passive drug loading from natural phospholipids and synthetic analogues such as the electrical charge zwitterionic phosphatidylcholines. Minor proportions of anionic phospholipids, such as phosphatidylglycerols, can be added to generate a net negative surface charge for colloid stabilization. Various trapping agents can be used based on the physical properties of co-loaded drugs (e.g., ammonium sulfate, transition metal ions and ammonium or substituted ammonium salt of the following: polyanionized sulfated cyclodextrin, sulfobutyl ether cyclodextrin, polyanionized sulfated sugar, polyphosphate, and the like).

Other aspects or advantages of the disclosure will be better appreciated in view of the following detailed description, examples, and claims.

BRIEF DESCRIPTION OF THE DRAWINGS

FIG. 17 illustrates the in-vitro screening of doxorubicin (DOX) and sunitinib (SUN) for synergy in SK-MEL-28 melanoma cells. A: Combination index (CI) is plotted as a function of cell growth inhibition (i.e., fraction affected, Fa) on SK-MEL-28 melanoma cells in response to the combination treatment by doxorubicin and sunitinib at various mole ratios: 1:5 (square), 1:1 (triangle) and 5:1 (circle). CI values of <0.9, 0.9-1.1, and >1.1 indicate synergy, additivity, and antagonism, respectively. B: In-vitro evaluation of CI from SK-MEL-28 melanoma cells plotted at $ED_{75}$ (black column, Fa=0.75) and $ED_{90}$ (blank columns, Fa=0.90) as a function of different doxorubicin to sunitinib molar drug ratios, i.e., 1:5, 1:1 and 5:1.

Figure 18:
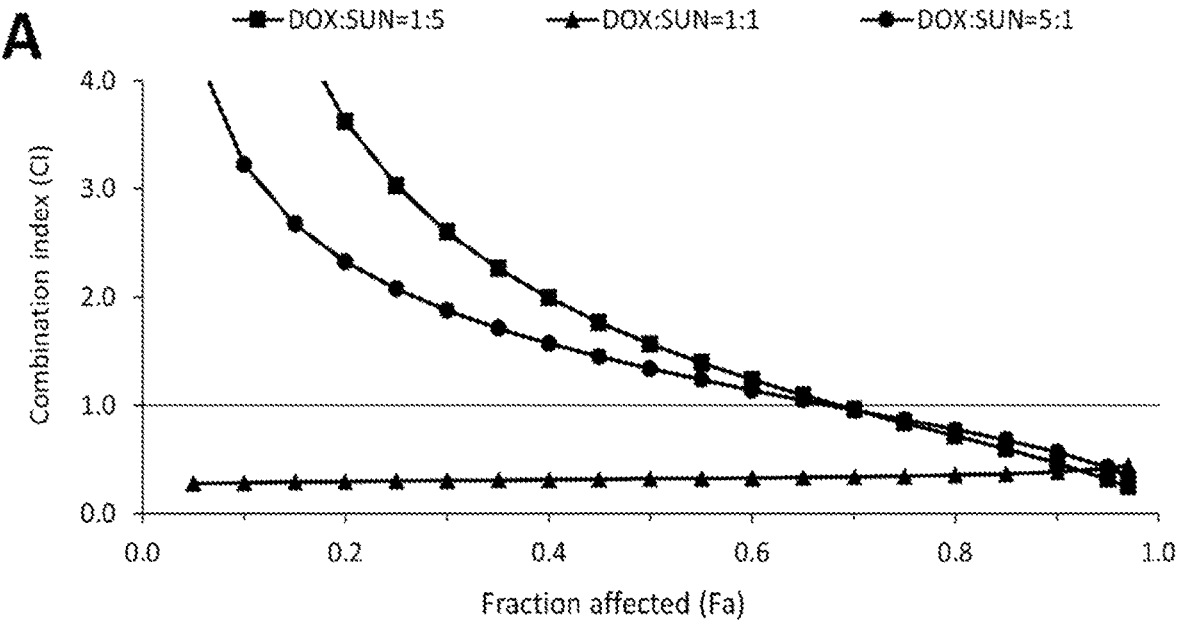
Figure 18:
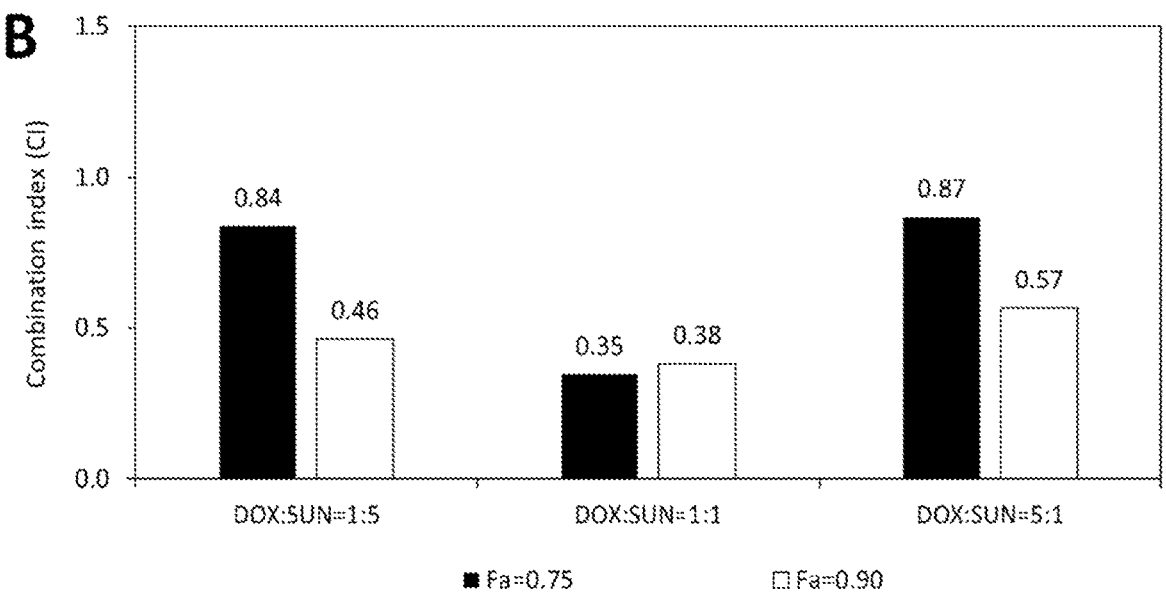

FIG. 18 illustrates the in-vitro screening of doxorubicin (DOX) and sunitinib (SUN) for synergy in BT-549 triple-negative breast cancer cells. A: Combination index (CI) is plotted as a function of cell growth inhibition (i.e., fraction affected, Fa) on BT-549 cells in response to the combination treatment by doxorubicin (DOX) and sunitinib (SUN) at various mole ratios: 1:5 (square), 1:1 (triangle) and 5:1 (circle). CI values of <0.9, 0.9-1.1, and >1.1 indicate synergy, additivity, and antagonism, respectively. B: In-vitro evaluation of CI from BT-549 breast cancer cells plotted at $ED_{75}$ (black column, Fa=0.75) and $ED_{90}$ (blank columns, Fa=0.90) as a function of different doxorubicin to sunitinib molar drug ratios, i.e., 1:5, 1:1 and 5:1.

Figure 19:
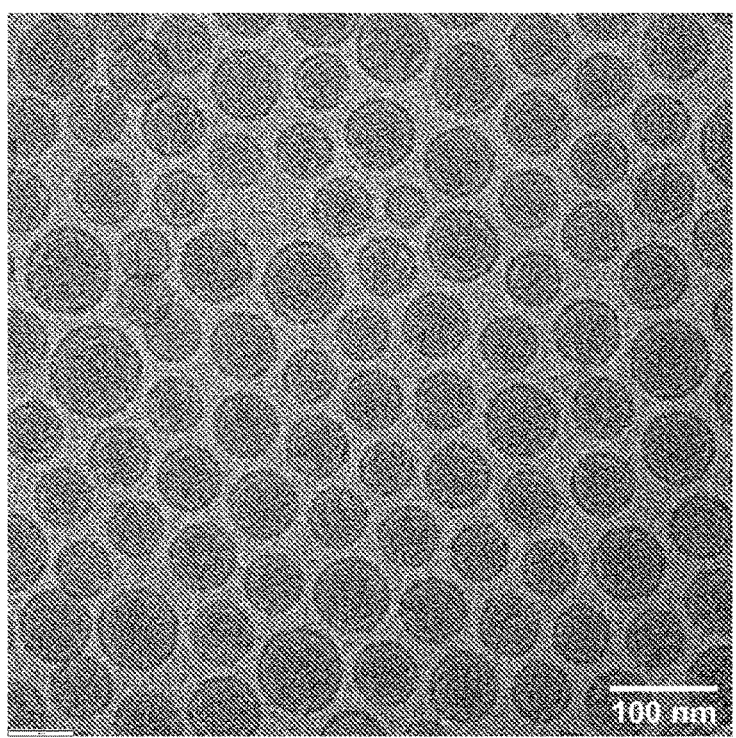

FIG. 19 shows a cryo-transmission electron microscopy (Cryo-TEM) image of liposome product of the combined doxorubicin and imatinib (DOX:IMT molar ratio of 1:5) with TEA-SBE-β-CD as the trapping agent.

Figure 20:
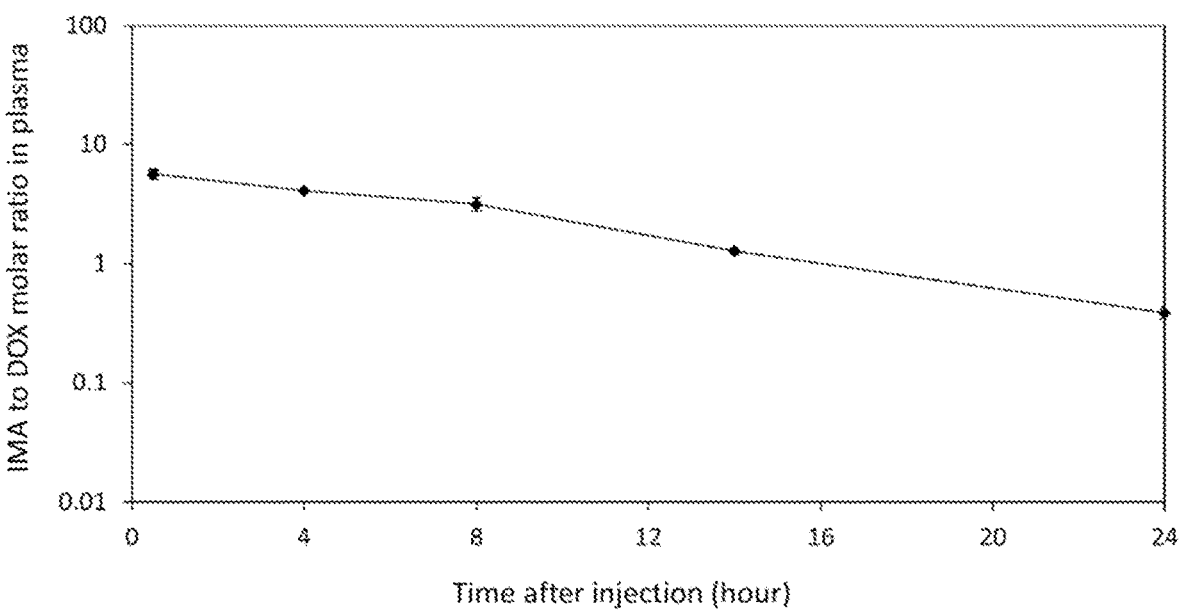

FIG. 20 illustrates the pharmacokinetic studies on liposome product of the combined doxorubicin and imatinib (DOX:IMT molar ratio of 1:5). DOX/IMT-L liposome was administrated at 6.0 (DOX)/27.3(IMT) mg/kg dose to CD-1 male mice (n=3 per time point) upon intravenous injection. The drug product contains TEA-SBE-β-CD as the intraliposomal trapping agent. Circulating plasma imatinib to doxorubicin molar ratios at each time point was calculated from absolute plasma concentrations.

Figure 21:
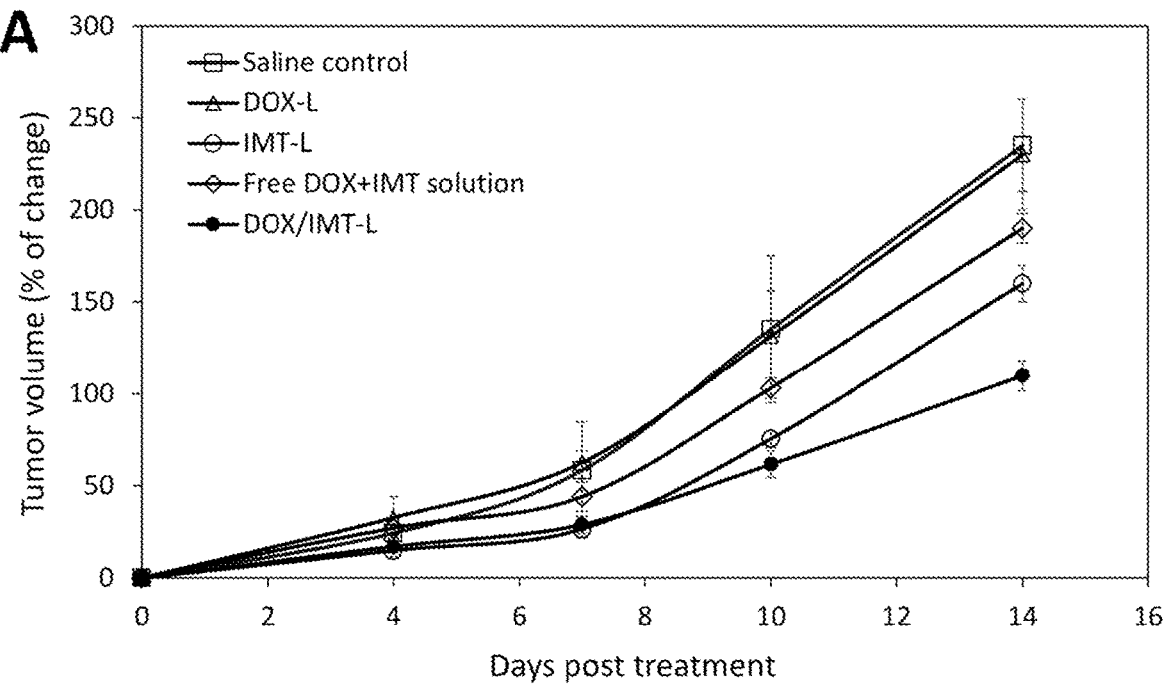
Figure 21:
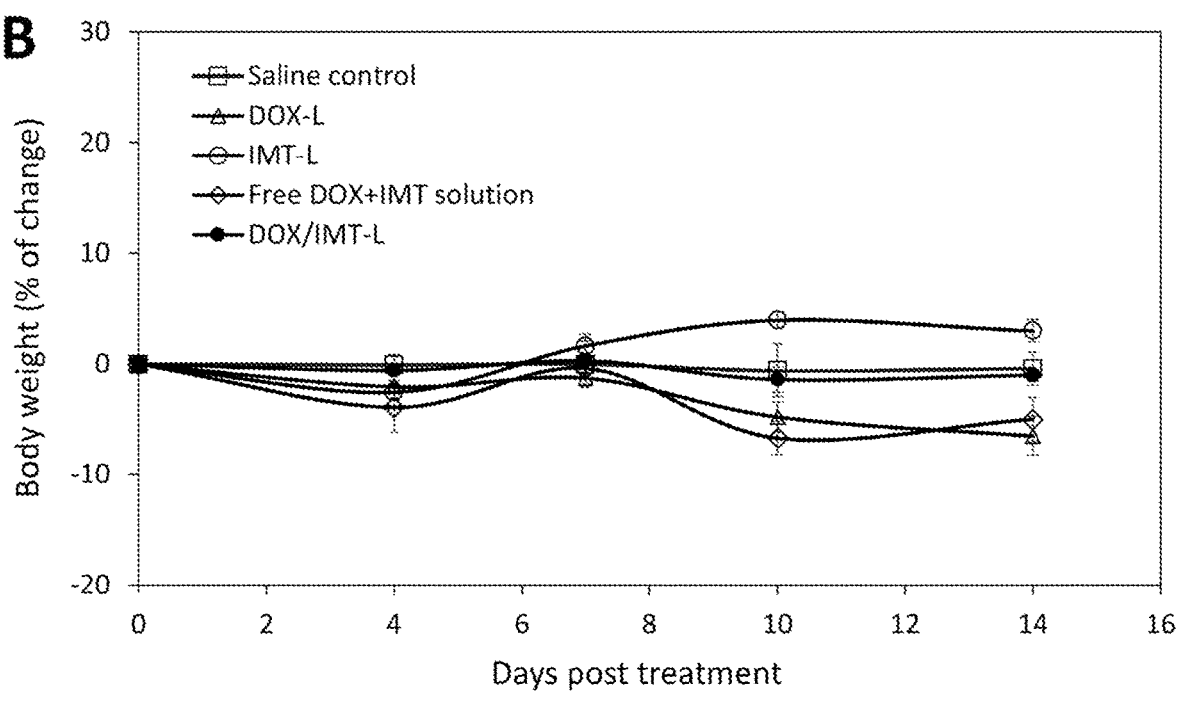

FIG. 21 illustrates the in-vivo efficacy of doxorubicin (DOX) and imatinib (IMT) co-delivered by liposomes against solid tumor model based on SK-MEL-28 melanoma cancer. A, percentage (%) of change on tumor volume and B, percentage (%) of change on body weight. The percentage shown in plot A and B were calculated by normalizing the tumor volume or body weight, respectively at a certain time point to that obtained at time 0. Tumor bearing female BALB/c nude mice (three per group) were treated intravenously every week for a total of two weeks. Information on each treatment group is described as follows: Saline (blank square); Liposomal doxorubicin, DOX-L (6 mg/kg, blank triangle); IMT-L (27.3 mg/kg, blank circle); Free doxorubicin/imatinib cocktail (6 DOX/27.3 IMT mg/kg respectively, blank diamond) and Liposomal doxorubicin/imatinib combination drug product, DOX/IMT-L (6 DOX/27.3 IMT mg/kg respectively, solid circle). For all liposomal drug products, TEA-SBE-(3-CD was used as the intraliposomal trapping agent.

DETAILED DESCRIPTION OF THE INVENTION

In the present invention, we have identified particular delivery vehicle formulations required to accommodate a combination of at least one chemotherapeutic cytotoxic agent (e.g., doxorubicin, daunorubicin, idarubicin, epirubicin and their derivatives, gemcitabine, vinorelbine, or the like) and at least one protein kinase inhibitor (e.g., imatinib, sunitinib, nintedanib, afatinib, ponatinib, ruxolitinib, or the like), which result in superior drug retention and sustained drug release of each agent. This has further demonstrated that synergistic ratios of these drugs, when encapsulated in liposomes, can be successfully maintained in the blood compartment extended period resulting in enhanced efficacy compared to the combined individual single conventional drug dosage form to treat related cancers and cancer drug resistances.

Among the nanoparticle delivery systems, liposomes are one of the most widely used pharmaceutical carriers with several unique characteristics including (1) prolonged drug circulation half-life mediated by the carrier, (2) reduced nonspecific uptake, (3) increased accumulation at the tumor site through the passive enhanced permeation and retention (EPR) effect and/or active targeting by incorporation of targeting ligands, (4) predominantly endocytotic uptake with the potential to bypass mechanisms of multidrug resistance, and (5) ability to tailor the relative ratios of each agent based on its pharmacological disposition, (6) a single delivery system carrying multiple drugs (hydrophilic and hydrophobic drugs) in the same platform can lead to synchronized and controlled pharmacokinetics of each drug, resulting in improved drug efficacy, single formulation with improved solubility and bioavailability (see, e.g., Mamot, C., et al., Drug Resist. Updates 2003, 6, 271-279).

The invention provides compositions comprising liposomes encapsulating at least one chemotherapeutic cancer drug and one protein kinase inhibitor, wherein the chemotherapeutic cancer drug and the protein kinase inhibitor are present at chemotherapeutic drug: protein kinase inhibitor (e.g., doxorubicin:imatinib or doxorubicin:sunitinib) molar ratios (doxorubicin only, doxorubicin:imatinib or doxorubicin:sunitinib being about 30:1 to about 1:30, and imatinib or sunitinib only) that exhibit a desired cytotoxic, cytostatic or biologic effect to relevant cells or tumor homogenates. Preferably, liposomal compositions provided herein will include liposomes encapsulating at least one chemotherapeutic drug and at least one protein kinase inhibitor in a molar ratio of the chemotherapeutic agent to protein kinase inhibitor that exhibits a non-antagonistic effect to relevant cells or tumor homogenates.

In one aspect, the present disclosure provides a pharmaceutical composition comprising liposomes suspended in a liquid medium, wherein the liquid medium comprises water and a pH buffer agent; wherein the liposome comprises an interior compartment surrounded by an outer lipid bilayer membrane, wherein the interior compartment comprises a protein kinase inhibitor (sometimes preferably a tyrosine kinase inhibitor), or a combination of a hydrophilic chemotherapeutic agent and a protein kinase inhibitor (sometimes preferably a tyrosine kinase inhibitor), in an aqueous medium; wherein the lipid bilayer membrane comprises a hydrophilic inner surface forming the interior compartment, a lipophilic bilayer, and a hydrophilic outer surface in contact with the liquid medium of the composition; and wherein the hydrophilic chemotherapeutic agent and protein kinase inhibitor can be released from the liposomess in a synergistic mode.

In some embodiments, in the pharmaceutical composition, the lipid bilayer membrane of the liposomes comprises (a) at least 10 mol % of a phospholipid selected from the group consisting of phosphatidylcholine (e.g., HSPC, DSPC, DPPC, DMPC), phosphatidylglycerol (e.g., DSPG), phosphatidylinositol, glyceroglycolipids, sphingoglycolipids (e.g., sphingomyelin), and combinations thereof; (b) 0-60 mol % cholesterol, or a derivative thereof; and (c)

optionally a charged phospholipid derivatized to polyethylene glycol (e.g., mPEG-2000-DSPE).

In some embodiments, in the pharmaceutical composition, the one or more lipids are independently selected from the group consisting of HSPC, DSPC, DPPC, DMPC, DSPG, mPEG-DSPE-2000, and cholesterol.

In some embodiments, in the pharmaceutical composition, the liquid medium further comprises one or more of the following: water-miscible organic solvent(s), osmotic agent (s), control release excipient.

In some embodiments, in the pharmaceutical composition, the aqueous interior compartment of the liposomes further comprises a trapping agent.

In some embodiments, in the pharmaceutical composition, the trapping agent is selected from the group consisting of ammonium sulfate, ammonium or substituted ammonium salts of polyanionized sulfobutyl ether cyclodextrin (e.g., TEA-SBE-α-cyclodextrin, TEA-SBE cyclodextrin, TEA-SBE-γ-cyclodextrin, Tris-SBE-α-cyclodextrin, Tris-SBE-β-cyclodextrin and Tris-SBE-γ-cyclodextrin); ammonium or substituted ammonium salts of polyanionized sulfated carbohydrates (e.g., TEA-SOS and Tris-SOS); ammonium or substituted ammonium salt of polyphosphate (e.g., triethyl-ammonium inositol hexaphosphate and tris(hydroxymethyl) aminomethane inositol hexaphosphate); transition metal salts (e.g., salts of copper, zinc, manganese, nickel, cobalt, or the like, with halide, sulfate and gluconate); quaternary ammonium compounds (e.g., benzalkonium chloride, benzethonium chloride, cetrimonium bromide, stearyl dimethylbenzyl ammonium chloride), polyoxyethylene (i.e., polyethylene glycols), and coconut amine.

In some embodiments, in the pharmaceutical composition, the outer surface of the lipid bilayer membrane of the liposomes comprises a surface negative charged lipid (e.g. DSPG) or a surface-modifying agent containing polyethylene glycol (e.g., mPEG-2000-DSPE), wherein the molar ratio of the total lipid to the protein kinase inhibitor, or the total amount of the hydrophilic chemotherapeutic agent and protein kinase inhibitor combined when both present, is at least equivalent (1:1).

In some embodiments, in the pharmaceutical composition, the chemotherapeutic agent is selected from the group consisting of doxorubicin, cyclophosphamide, carboplatin, paclitaxel, daunorubicin, epirubicin, 5-fluorouracil, gemcitabine, eribulin, ixabepilone, methotrexate, mutamycin, mitoxantrone, vinorelbine, docetaxel, thiotepa, bleomycin, vincristine, dacarbazine, capecitabine, prednisone, camptothecin, topotecan, irinotecan, BCNU, carmustine, cis-platin, lenalidomide, and pemetrexed.

In some embodiments, in the pharmaceutical composition, the protein kinase inhibitor is selected from the group consisting of imatinib, sunitinib, afatinib, nintedanib, ponatinib, ruxolitinib, crizotinib, ibrutinib, acalabrutinib, abemaciclib, aflibercept, alectinib, avapritinib, axitinib, bosutinib, cabozantinib, capmatinib, ceritinib, cobimetinib, crizotinib, dabrafenib, dacomitinib, dasatinib, encorafenib, entrectinib, erdafitinib, erlotinib, everolimus, fedratinib, fostamatinib, gefitinib, gilteritinib, ibrutinib, lapatinib, larotrectinib, lenvatinib, lorlatinib, nintedanib, neratinib, nilotinib, netarsudil, osimertinib, pacritinib, pazopanib, pexidartinib, pemigatinib, palbociclib, ponatinib, pexidartinib, pralsetinib, quizartinib, regorafenib, ribociclib, ripretinib, selpercatinib, selumetinib, sorafenib, temsirolimus, tofacitinib, trametinib, tucatinib, upadacitinib, vandetanib, vemurafenib, zanubrutinib, and ziv-aflibercept.

In some embodiments, in the pharmaceutical composition, the interior compartment of the liposome comprise an anticancer agent or combination selected from the group consisting of the following:

(a) imatinib encapsulated alone;

(b) doxorubicin and imatinib co-encapsulated;

(c) sunitinib encapsulated alone;

(d) doxorubicin and sunitinib co-encapsulated;

(e) gemcitabine encapsulated alone;

(f) gemcitabine and sunitinib co-encapsulated;

(g) doxorubicin and imatinib in about 30:1 to about 1:30 molar ratio;

(h) doxorubicin and sunitinib in about 30:1 to about 1:30 molar ratio; and (i) gemcitabine and sunitinib in about 30:1 to about 1:30 molar ratio.

In some embodiments, in the pharmaceutical composition, the liposomes have a mean particle size between 4.5 nm to 450 nm, preferably between 25 nm and 300 nm, and more preferably between 50 nm to 200 nm.

In some embodiments, in the pharmaceutical composition, the chemotherapeutic agent and protein kinase inhibitor can be released sequentially in a synergistic mode upon administration.

In some embodiments, in the pharmaceutical composition, the molar ratio of the two co-encapsulated agents (i.e., the chemotherapeutic agent and protein kinase inhibitor) is such that when said ratio is provided to cancer cells relevant to said cancer in an in-vitro assay over the concentration range at which the fraction of affected cells is about 0.20 to 0.80, synergy is exhibited over at least 20% of said range.

In some embodiments, in the pharmaceutical composition, the liposome encapsulated with a chemotherapeutic agent and a protein kinase inhibitor, maintains for at least one hour of the said synergistic molar drug ratio in blood after in-vivo administration.

In another aspect, the present disclosure provides a pharmaceutical composition according to any embodiments disclosed herein for use in the treatment of a cancer or drug resistance of cancer in a subject in need of treatment, wherein the cancer is optionally selected from the group consisting of breast cancer, melanoma, gastrointestinal cancer, lung cancer, colorectal cancer, Ewing sarcoma, pancreatic cancer, prostate cancer, bladder cancer, kidney cancer, thyroid cancer, uterine cancer, and gastrointestinal stromal tumors, wherein the chemotherapeutic agent and protein kinase inhibitor can be delivered by the liposome with a synergistic cytotoxic or cytostatic effect on cancer cells.

In another aspect, the present disclosure provides a method of treating a cancer or drug resistance of a cancer, comprising administering to a subject in need of treatment a therapeutically effective amount of a pharmaceutical composition according to any embodiments disclosed herein.

In some embodiments, the cancer is selected from the group consisting of breast cancer, melanoma, gastrointestinal cancer, lung cancer, colorectal cancer, Ewing sarcoma, pancreatic cancer, prostate cancer, bladder cancer, kidney cancer, thyroid cancer, uterine cancer, and gastrointestinal stromal tumors.

In some embodiments, the breast cancer is triple negative breast cancer, and wherein the lung cancer is caused by either a high level of phosphorylation of a wild-type EGFR or a mutation within an EGFR amino acid sequence.

In another aspect, the present disclosure provides a method of preparing a liposomal pharmaceutical composition (e.g., according to any one of claims 1 to 11), wherein the liposome is made by a process comprising the steps of:

(a) forming multilamellar liposome vesicles in a solution comprising water, lipid(s), and trapping agent(s);

(b) extruding the multilamellar liposome vesicles multiple times at an elevated temperature (e.g., in the range of 40-75° C.) through polycarbonate membranes (e.g., with a size of 50 nm or 100 nm) to form unilamellar liposomes;

(c) substantially removing the trapping agent(s) that are outside of the liposomes by diafiltration or size exclusion chromatography, or other buffer exchanging methods; and (d) heating the unloaded liposomes at an elevated temperature (e.g., 40-75° C.) in an aqueous solution comprising one or more active pharmaceutical ingredients (APIs), thereby forming drug encapsulated liposomes.

In some embodiments, the lipid is selected from the group consisting of: (a) at least 10 mol % of a phospholipid selected from the group consisting of phosphatidylcholine (e.g., HSPC, DSPC, DPPC, DMPC), phosphatidylglycerol (e.g., DSPG), phosphatidylinositol, glyceroglycolipids, sphingoglycolipids (e.g., sphingomyelin), and combinations thereof; (b) 0-60 mol % cholesterol, or a derivative thereof; and (c) optionally a charged phospholipid derivatized to polyethylene glycol (e.g. mPEG-2000-DSPE).

In some embodiments, the trapping agent is selected from the group consisting of ammonium sulfate; ammonium or substituted ammonium salts of polyanionized sulfobutyl ether cyclodextrin (e.g., TEA-SBE-α-cyclodextrin, TEA-SBE-β-cyclodextrin, TEA-SBE-γ-cyclodextrin, Tris-SBE-α-cyclodextrin, Tris-SBE-β-cyclodextrin and Tris-SBE-γ-cyclodextrin); and ammonium or substituted ammonium salt of polyanionized sulfated carbohydrates (e.g., TEA-SOS and Tris-SOS); ammonium or substituted ammonium salts of polyphosphate (e.g. triethylammonium inositol hexaphosphate and tris(hydroxymethyl) aminomethane inositol hexaphosphate); transition metal salts (e.g., salts of copper, zinc, manganese, nickel, cobalt, or the like, with halide, sulfate, or gluconate); quaternary ammonium compounds (e.g., benzalkonium chloride, benzethonium chloride, cetrimonium bromide, stearyl dimethylbenzyl ammonium chloride), polyoxyethylene (i.e., polyethylene glycols), and coconut amine.

In some embodiments, the method comprises a process selected from: active loading, passive loading, and combination thereof; wherein the active or passive loading is selected from the group consisting:

(a) pH gradient-based active loading method, which encapsulates the APIs based on a transmembrane pH gradient, wherein the pH value of the interior aqueous compartment of the liposome is lower than that outside the liposome;

(b) transition metal-based active loading method, which encapsulates the APIs by utilizing transition metal ions to drive the uptake of APIs into liposomes via complexation;

(c) passive loading method, which encapsulates the APIs during the liposome formation; and (d) passive loading method, which involves passive equilibration after the formation of liposomes.

In some embodiments, the pH gradient is formed by a concentration gradient of an ammonium ion or a concentration gradient of an organic compound having an ammonium derivative or substituted ammonium capable of being protonated.

In some embodiments, the API is a protein kinase inhibitor (sometimes preferably a tyrosine kinase inhibitor) or a combination of a chemotherapeutic agent and a protein kinase inhibitor (sometimes preferably a tyrosine kinase inhibitor).

In some embodiments, the chemotherapeutic agent is selected from the group consisting of doxorubicin, cyclophosphamide, carboplatin, paclitaxel, daunorubicin, epirubicin, 5-fluorouracil, gemcitabine, eribulin, ixabepilone, methotrexate, mitomycins, mitoxantrone, vinorelbine, docetaxel, thiotepa, bleomycin, vincristine, dacarbazine, capecitabine, prednisone, camptothecin, topotecan, irinotecan, carmustine, cis-platin, BCNU, lenalidomide, and pemetrexed.

In some embodiments, the protein kinase inhibitor is selected from the group consisting of imatinib, sunitinib, afatinib, nintedanib, ponatinib, ruxolitinib, crizotinib, ibrutinib, acalabrutinib, abemaciclib, aflibercept, alectinib, avapritinib, axitinib, bosutinib, cabozantinib, capmatinib, ceritinib, cobimetinib, crizotinib, dabrafenib, dacomitinib, dasatinib, encorafenib, entrectinib, erdafitinib, erlotinib, everolimus, fedratinib, fostamatinib, gefitinib, gilteritinib, ibrutinib, lapatinib, larotrectinib, lenvatinib, lorlatinib, nintedanib, neratinib, nilotinib, netarsudil, osimertinib, pacritinib, pazopanib, pexidartinib, pemigatinib, palbociclib, ponatinib, pexidartinib, pralsetinib, quizartinib, regorafenib, ribociclib, ripretinib, selpercatinib, selumetinib, sorafenib, temsirolimus, tofacitinib, trametinib, tucatinib, upadacitinib, vandetanib, vemurafenib, zanubrutinib, ziv-aflibercept, and combinations thereof.

In some embodiments, the liposomes have a mean particle size in the range of between 4.5 nm to 450 nm, preferably between 25 nm and 300 nm, and more preferably between 50 nm to 200 nm.

In another aspect, the present invention provides a plurality of drug-loaded liposomes as disclosed in any embodiments examples herein and/or prepared by a method according to any embodiments or examples disclosed herein.

In another aspect, the present invention provides a treatment kit comprising a container and a plurality of the drug-loaded liposomes according to any embodiments disclosed herein in the container, wherein the drug-loaded liposomes are or can be suspended in a sterile diluent solution ready for administration to a subject in need of treatment.

In further embodiments of the invention, the above described lipid-based delivery vehicles comprise a third or fourth agent, for example, any therapeutic, diagnostic or cosmetic agent.

In some embodiments of the invention, liposomes comprising one or more phospholipids are provided. In some embodiments, the phospholipids are selected from the group consisting of mPEG-2000-DSPE, DPPC, DMPC, DSPC, HSPC, DSPE, DSPG, and the like. Wherein, the phospholipid is not less than 10 mol % of the total lipids, and the negative charged lipid is mPEG-2000 DSPE or DSPG as the liposomal stabilizing lipid.

In some embodiments of the invention, liposomes comprising a sterol are provided. In some embodiments, the sterol is cholesterol with around 0-60% mole of the total lipids.

In some embodiments of the invention, liposomes comprising a trapping agent for active loading in the liposome core compartment are provided. In some embodiments, the trapping agent is selected from the group consisting of ammonium sulfate, transition metals and ammonium or substituted ammonium salt of the following: polyanionized sulfated cyclodextrin, sulfobutyl ether cyclodextrin, polyanionized sulfated sugar, polyphosphate, and the like.

The lipid-based delivery vehicles of the present invention may be used not only in parenteral administration, but also in topical, nasal, subcutaneous, intraperitoneal, intramuscular, aerosol or oral delivery or by the application of the delivery vehicle onto or into a natural or synthetic implantable device at or near the target site for therapeutic purposes or medical imaging and the like. Preferably, the lipid-based delivery vehicles of the invention are used in parenteral administration, most preferably, intravenous administration.

As those skilled in the art would understand, all the drug-loaded liposomes and pharmaceutical compositions prepared therefrom must be made under sterile conditions required of any materials and processes used in order for use in the administration to a subject in need of treatment. Thus, while the disclosure is not so limited, all the liposomes and pharmaceutical compositions disclosed or claimed herein and intended for treatment of a subject are sterile.

The preferred embodiments herein described are not intended to be exhaustive or to limit the scope of the invention to the precise forms disclosed. They are chosen and described to best explain the principles of the invention and its application and practical use to allow others skilled in the art to comprehend its teachings.

1. Composition

A. Therapeutic Agents a. Protein Kinase Inhibitors i. Tyrosine Kinase Inhibitors (TKIs)

Any compounds that inhibit the tyrosine kinase pathway may be used in the present invention. Preferred compounds described in the studies are listed below:

Imatinib targets multiple BCR-Abl and PDGFR α/β receptors.

Sunitinib targets PDGFR α/β and VEGR family receptors.

Afatinib targets EGFR family receptors.

Nintedanib targets PDGFR α/β and VEGFR family receptors.

Ponatinib targets BCR-Abl and Src family receptors.

Ruxolitinib targets JAK family receptors.

Crizotinib targets ALK and c-Met receptors.

Ibrutinib targets BTK receptors.

Other TKIs include the following: acalabrutinib, alectinib, alecensa, avapritinib, axitinib, bosutinib, cabozantinib, dacomitinib, dasatinib, entrectinib, erlotinib, gilteritinib, icotinib, lapatinib, midostaurin, neratinib, nilotinib, pacritinib, pazopanib, pexidartinib, quizartinib, regorafenib, sorafenib, vandetanib, zanubrutinib, aflibercept, etc.

ii. Other Types of Protein Kinase Inhibitors

Protein kinase inhibitors that inhibit other kinase pathways are included as follows: Abemaciclib, capmatinib, larotrectinib, lorlatinib, netarsudil, pemigatinib, ribociclib, ceritinib, cobimetinib, dabrafenib, encorafenib, erdafitinib, everolimus, fedratinib, fostamatinib, gefitinib, lenvatinib, osimertinib, palbociclib, pralsetinib, ripretinib, selpercatinib, selumetinib, temsirolimus, trametinib, tucatinib, upadacitinib, vandetanib, vemurafenib.

Many protein kinases are associated with human cancer initiation and progression. The recent development of protein kinase inhibitors for the treatment of diverse types of cancer has proven successful in clinical therapy. Among the protein kinase inhibitors, protein tyrosine kinase (PTK) is one of the major signaling enzymes in the process of cell signal transduction, which catalyzes the transfer of ATP-γ-phosphate to the tyrosine residues of the substrate protein, making it phosphorylated, regulating cell growth, differentiation, death and a series of physiological and biochemical processes. Abnormal expression of PTK usually leads to cell proliferation disorders, and is closely related to tumor invasion, metastasis, and tumor angiogenesis. At present, a variety of PTKs have been used as targets in the screening of anticancer drugs. PTK inhibitors compete with ATP for the ATP binding site of PTK and reduce tyrosine kinase phosphorylation, thereby inhibiting cancer cell proliferation. Thus, PTK inhibitors have made great progress in the treatment of cancer, but the resulting acquired resistance is still inevitable, restricting the treatment of cancer.

Preferred PTK inhibitors are described in the studies below.

Imatinib (IMT) is a TKI inhibitor with highly potent and specific inhibitory activity against BCR-ABL fusion gene, the platelet-derived growth factor receptor (PDGFR), and the c-KIT receptor. The mesylate salt of imatinib, which is marketed by Novartis as Gleevec®, was approved in 2001 by FDA for the treatment of Philadelphia chromosome-positive chronic myeloid leukemia (Ph+ CML), myelodysplastic/myeloproliferative diseases associated with PDGFR gene rearrangements, aggressive systemic mastocytosis, hypereosinophilic syndrome, chronic eosinophilic leukemia, dermatofibrosarcoma protuberans, and malignant gastrointestinal stromal tumors.

Another preferred TKI inhibitor, sunitinib (SUN), is a multi-targeted tyrosine kinase inhibitor that inhibits PDGFR (A and B), VEGFR1, VEGFR2, FLT3R, c-Kit, and RET-mediated signaling. In 2017, FDA approved sunitinib malate as SUTENT® by Pfizer as an adjuvant therapy for the treatment of adult patients with high risk of recurrent renal cell carcinoma (RCC) following nephrectomy, gastrointestinal stromal tumor (GIST) after disease progression on or intolerance to imatinib mesylate, advanced renal cell carcinoma. Progressive, well-differentiated pancreatic neuroendocrine tumors (pNET) in patients with unresectable locally advanced or metastatic disease.

b. Chemotherapeutic Agents

Any chemotherapeutic agents for cancer treatment may be used in the present invention. Preferred compounds described in the studies are listed below:Doxorubicin, cyclophosphamide, carboplatin, paclitaxel, daunorubicin, epirubicin, 5-fluorouracil, gemcitabine, eribulin, ixabepilone, methotrexate, mitomycins, mitoxantrone, vinorelbine, docetaxel, thiotepa, bleomycin, vincristine, dacarbazine, capecitabine, prednisone, camptothecin, topotecan, irinotecan, carmustine, cis-platin, lenalidomide, pemetrexed.

Preferred chemotherapeutic compounds are described in the studies below.

Doxorubicin is commonly used in the treatment of a wide range of cancers, including some leukemias and Hodgkin's lymphoma, as well as cancers of the bladder, breast, stomach, lung, ovaries, thyroid, soft tissue sarcoma, multiple myeloma, and others.

Doxorubicin is an anthracycline antibiotic, closely related to the natural product daunomycin. Like all anthracyclines, it works by intercalating DNA. Doxorubicin interacts with DNA by intercalation and inhibition of macromolecular biosynthesis. This inhibits the progression of the enzyme topoisomerase II, which relaxes supercoils in DNA for transcription. Doxorubicin stabilizes the topoisomerase II complex after it has broken the DNA chain for replication, preventing the DNA double helix from being resealed and thereby stopping the process of replication. The planar aromatic chromophore portion of the molecule intercalates between two base pairs of the DNA, while the six-membered daunosamine sugar sits in the minor groove and interacts with flanking base pairs immediately adjacent to the intercalation site, as evidenced by several crystal structures.

Other anthracycline DNA intercalators include daunorubicin, arugamycin, epirubicin (an epimer of doxorubicin and differs only in the orientation of the C-4 hydroxyl group on the sugar), idarubicin (an analog of daunorubicin, It lacks the C-4 methoxy group), and valrubicin (N-trifluoroacetyl, 1-4-valerate derivative of doxorubicin).

For many decades, chemotherapy has played a vital role in the auxiliary treatment of cancer and gained extensive development. However, the emergence of drug resistance and tumor recurrence is often associated with the cancer chemotherapy, mainly due to pathway overlap, cross-talk, and neutralization response that commonly occur with cancer monotherapy. As an example, the chemotherapeutic anthracycline drug doxorubicin (DOX) has been used to treat various cancers, such as breast cancer, ovarian cancer, and triple negative (ER2, PR 2, Her-22) breast cancer; however, resistance still arises in many cases (Cobleigh MA (2011). Semin Oncol., 38, Suppl 2: S11-16). For other cancers, such as melanoma, doxorubicin is not routinely utilized due to intrinsic resistance. Thus, although doxorubicin is a highly effective chemotherapeutic agent, its use is very limited due to the resistance as well as due to its narrow therapeutic window (e.g. cardiac toxicity) (Shi., Y, et al. (2011). Herz 36: 296-305).

For the cancer and cancer drug resistance treatment, the investigation with combined regimes of doxorubicin and other cancer drugs has been conducted frequently in clinical studies. The combination of doxorubicin and a tyrosine kinase inhibitor, imatinib, has been reported to effectively reverse intrinsic and acquired resistances associated with doxorubicin by inhibiting ABC transporter function (Sims, J. T., et al. PLOS One 2013, 8, e55509). Maurel et al. (2010) conducted a Phase I-II study of doxorubicin plus imatinib in patients with gastrointestinal sarcoma tumors refractory. It was concluded that the low-dose chemo-biotherapy combination of doxorubicin and imatinib shows promising activity in heavily pretreated gastrointestinal sarcoma tumor patients, especially in those with WT KIT phenotype, and appears as a reasonable and safe option for patients not responding to high-dose imatinib therapy (Maurel J, et al., Cancer. 2010, 116(15):3692-3701).

Another preferred compound, gemcitabine, is a nucleoside analog that exhibits antitumor activity. Gemcitabine HCl is known to be effective in treating pancreatic cancer and lung cancer. In general, gemcitabine prevents cells from making DNA and RNA by interfering with the synthesis of nucleic acids. This action stops the growth of cancer cells, causing the cell death. Michaelson et al. (2015) reported a Phase 2 trial of gemcitabine and sunitinib in patients with sarcomatoid and/or poor-risk metastatic renal cell carcinoma. It was concluded that the antiangiogenic therapy and cytotoxic chemotherapy are an active and well-tolerated combination for patients with aggressive RCC. The combination may be more efficacious than either therapy alone. (Michaelson, M. D., et al., Cancer, 2015, 121(19):3435-43).

Other classes of chemotherapeutic compounds include anti-tumor drugs such as irinotecan, vinorelbine, gemcitabine, topotecan, vincristine, or the like, can also be used in the present invention.

B. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; solid forms suitable for use to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, buffer, and isotonic agents, for example, sugars, HUES buffer, or sodium chloride, etc.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, HEPES buffers, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

2. Controlled Release Formulations

The parenteral formulations described herein can be formulated for controlled release including immediate release, delayed release, extended release, pulsatile release, and combinations thereof.

For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into nano- and microparticles which provide controlled release of the drug(s). Release of the drug(s) is controlled by diffusion of the drug(s) out of the nano- and microparticles and/or degradation of the polymer particles by hydrolysis and/or enzymatic degradation. Suitable polymers include lipids and other natural or synthetic lipid derivatives.

Proteins which are water insoluble, such as zein, can also be used as materials for the formation of drug containing nano- and microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing nano- and microparticles can be achieved through known pharmaceutical formulation techniques. In the case of formulation in phospholipid or phospholipid-like materials, the carrier material is typically heated above its melting temperature and the drug is added to form a mixture comprising drug particles suspended in the carrier material, drug dissolved in the carrier material, or a mixture thereof. Nano- and microparticles can be subsequently formulated through several methods including, but not limited to, the processes of congealing, extrusion, spray chilling or aqueous dispersion. In a preferred process, lipid is heated above its melting temperature, rehydrated in aqueous solution, extruded, and drug loaded. These processes are known in the art.

3. Determining Non-Antagonistic Combined Drug Ratios In-Vitro

In a further aspect of the invention, the chemotherapeutic agents and protein kinase inhibitors will be encapsulated into liposomes at synergistic or additive (i.e. non-antagonistic) ratios. Determination of ratios of agents that display synergistic or additive combination effects may be carried out using various algorithms, based on the types of experimental, preferred the Chou-Talalay median-effect method in this invention (Chou, T. C., J. Theor. Biol. (1976) 39:253-276).

The underlying experimental data are generally determined in-vitro using cells in culture. Preferably, the combination index (CI) is plotted as a function of the fraction of cells affected (Fa), as explained above, a surrogate parameter for concentration range. Preferred combinations of agents are those that display synergy or additivity over a substantial range of Fa values. Combinations of agents are selected if non-antagonistic over at least about 5% of the concentration range wherein greater than 1% of the cells are affected, i.e., an Fa range greater than 0.01. Preferably, a larger portion of overall concentration exhibits a favorable CI; for example, 5% of a Fa range of 0.2-1.0. More preferably about 10% of this range exhibits a favorable CI. Even more preferably, about 20% of the Fa range, preferably over about 50% and most preferably over at least about 70% of the Fa range of 0.2 to 1.0 are utilized in the compositions. Combinations that display synergy over a substantial range of Fa values may be re-evaluated at a variety of agent ratios to define the optimal ratio to enhance the strength of the non-antagonistic interaction and increase the Fa range over which synergy is observed.

While it would be desirable to have synergy over the entire range of concentrations over which cells are affected, it has been observed that in many instances, the results are considerably more reliable in an Fa range of 0.2-0.8 when using a spectrophotometric method such as the MTT assay. Thus, although the synergy exhibited by combinations of the invention is set forth to exist within the broad range of 0.01 or greater, it is preferable that the synergy be established in the Fa range of 0.2-0.8. Other more sensitive assays, however, can be used to evaluate synergy at Fa values greater than 0.8, for example, bioluminescence or clonogenecity assays.

The optimal combination ratio may be further used as a single pharmaceutical unit to determine synergistic or additive interactions with a third agent. In addition, a three-agent combination may be used as a unit to determine non-antagonistic interactions with a fourth agent, and so on.

As set forth above, the in-vitro studies on cell cultures will be conducted with "relevant" cells. The choice of cells will depend on the intended therapeutic use of the agent. Only one relevant cell line or cell culture type needs exhibit the required non-antagonistic effect in order to provide a basis for the compositions to come within the scope of the invention.

For example, in one preferred embodiment of the invention, the combination of agents is intended for anticancer therapy. In a frequent embodiment, the combination of agents is intended for multiple cancers, such as leukemia or lymphoma therapy, breast cancer, triple negative breast cancer, gastrointestinal cancer, and lung cancer. Appropriate choices will then be made of the cells to be tested and the nature of the test. In particular, tumor cell lines are suitable subjects and measurement of cell death or cell stasis is an appropriate end point. As will further be discussed below, in the context of attempting to find suitable non-antagonistic combinations for other indications, other target cells and criteria other than cytotoxicity or cell stasis could be employed.

For determinations involving antitumor agents, cell lines may be obtained from standard cell line repositories (NCI or ATCC for example), from academic institutions or other organizations including commercial sources. Preferred cell lines would include one or more selected from cell lines identified by the Developmental Therapeutics Program of the NCI/NIH. The tumor cell line screen used by this program currently identifies about 60 different tumor cell lines representing leukemia, melanoma, and cancers of the lung, colon, brain, ovary, breast, prostate, stomach, and kidney, etc. The required non-antagonistic effect over a desired concentration range need be shown only on a single cell type; however, it is preferred that at least two cell lines exhibit this effect, more preferably three cell lines, more preferably five cell lines, and more preferably 10 cell lines. The cell lines may be established tumor cell lines or primary cultures obtained from patient samples. The cell lines may be from any species but the preferred source will be mammalian and in particular human. The cell lines may be genetically altered by selection under various laboratory conditions.

In one preferred embodiment, the given effect (Fa) refers to cell death or cell stasis after application of a cytotoxic agent to a cell culture. Cell death or viability may be measured by MTT assay in this invention. Non-antagonistic ratios of two or more agents can be determined for disease indications other than cancer and this information can be used to prepare therapeutic formulations of two or more drugs for the treatment of these diseases. With respect to in-vitro assays, many measurable endpoints can be selected from which to define drug synergy, provided those endpoints are therapeutically relevant for the specific disease. As set forth above, the in-vitro studies on cell cultures will be conducted with "relevant" cells. The choice of cells will depend on the intended therapeutic use of the agent. In-vitro studies on individual patient biopsies or whole tumors can be conducted with "tumor homogenate." generated from homogenization of the tumor sample(s) into single cells. In one preferred embodiment, the given effect (Fa) refers to cell death or cell stasis after application of a cytotoxic agent to a "relevant" cell culture. Cell death or viability may be measured using a number of methods known in the art.

4. Preparation of Lipid-Based Delivery Vehicles

Preferred lipid carriers for use in this invention are liposomes. Suitable liposomes for use in this invention include large unilamellar vesicles (LUVs), multilamellar vesicles (MLVs), small unilamellar vesicles (SUVs) and interdigitating fusion liposomes. Liposomes for use in this invention may be prepared to contain a phosphatidylcholine lipid or phospholipid-like material, such as distearylphosphatidylcholine (DSPC) or hydrogenated soy phosphatidylcholine (HSPC).

Liposomes of the invention may also contain a sterol, such as cholesterol. Liposomes may also contain therapeutic lipids, which examples include ether lipids, phosphatidic acid, phosphonates, ceramide and ceramide analogs, sphingosine and sphingosine analogs and serine-containing lipids.

Liposomes may also be prepared with surface stabilizing hydrophilic polymer-lipid conjugates, such as polyethylene glycol-DSPE, to enhance circulation longevity. The incorporation of negatively charged lipids such as phosphatidylglycerol (PG) and phosphatidylinositol (PI) may also be added to liposome formulations to increase the circulation longevity of the carrier. These lipids may be employed to replace hydrophilic polymer-lipid conjugates as surface stabilizing agents. Preferred embodiments of this invention may make use of liposomes containing phosphatidylglycerol (PG) or phosphatidylinositol (PI) to prevent aggregation thereby increasing the blood residence time of the carrier.

In one embodiment, liposome compositions in accordance with this invention are preferably used to treat cancer. Delivery of encapsulated drugs to a tumor site is achieved by administration of liposomes of the invention. Preferably liposomes have a mean diameter of particle size less than 300 nm. Most preferably liposomes have a mean diameter of particle size less than 200 nm. Tumor vasculature is generally leakier than normal vasculature due to fenestrations or gaps in the endothelia. This allows delivery vehicles of 200 nm or less in diameter to penetrate the discontinuous endothelial cell layer and underlying basement membrane surrounding the vessels supplying blood to a tumor. Selective accumulation of the delivery vehicles into tumor sites following extravasation leads to enhanced anticancer drug delivery and therapeutic effectiveness.

Various methods may be utilized to encapsulate active agents in liposomes. "Encapsulation" includes covalent or non-covalent association of an agent with the lipid-based delivery vehicle. For example, this can be by interaction of the agent with the outer layer or layers of the liposome or entrapment of an agent within the liposome, equilibrium being achieved between different portions of the liposome. Thus, encapsulation of an agent can be by association of the agent by interaction with the bilayer of the liposomes through covalent or non-covalent interaction with the lipid components or entrapment in the aqueous interior of the liposome, or in equilibrium between the internal aqueous phase and the bilayer. "Loading" refers to the act of encapsulating one or more agents into a delivery vehicle.

Encapsulation of the desired combination can be achieved either through encapsulation in separate delivery vehicles or within the same delivery vehicle. Where encapsulation into separate liposomes is desired, the lipid composition of each liposome may be quite different to allow for coordinated pharmacokinetics. By altering the vehicle composition, release rates of encapsulated drugs can be matched to allow desired ratios of the drugs to be delivered to the tumor site. Means of altering release rates include increasing the acyl chain length of vesicle forming lipids to improve drug retention, controlling the exchange of surface grafted hydrophilic polymers such as mPEG-DSPE out of the liposome membrane and incorporating membrane-rigidifying agents such as sterols or sphingomyelin into the membrane. It should be apparent to those skilled in the art that if a first and second drug are desired to be administered at a specific drug ratio and if the second drug is retained poorly within the liposome composition of the first drug (e.g., DMPC/Chol), that improved pharmacokinetics may be achieved by encapsulating the second drug in a liposome composition with lipids of increased acyl chain length (e.g., DSPC/Chol). When encapsulated in separate liposomes, it should be readily accepted that ratios of both drugs that have been determined on a patient-specific basis to provide optimal therapeutic activity can be generated for individual patients by combining the appropriate amounts of each liposome encapsulated drug prior to administration. Alternatively, two or more agents may be encapsulated within the same liposome.

Techniques for encapsulation are dependent on the nature of the therapeutic agents and delivery vehicles. For example, therapeutic agents may be loaded into liposomes using both passive and active loading methods. Passive methods of encapsulating active agents in liposomes involve encapsulating the agent during the preparation of the liposomes. This technique results in the formation of multilamellar vesicles (MLVs) that can be converted to large unilamellar vesicles (LUVs) or small unilamellar vesicles (SUVs) upon extrusion. In addition, another suitable method of passive encapsulation involves passive equilibration after the formation of liposomes. This process involves incubating preformed liposomes under altered or non-ambient (based on temperature, pressure, etc.) conditions and adding a therapeutic agent (e.g., chemotherapeutic agent and/or protein kinase inhibitor) to the exterior of the liposomes. The therapeutic agent then equilibrates into the interior of the liposomes, across the liposomal membrane. The liposomes are then returned to ambient conditions and unencapsulated therapeutic agent, if present, is removed via dialysis or another suitable method.

Active loading methods of drug encapsulation include the pH gradient loading approach and active transition metal-loading technique. Loading method based on the transmembrane pH gradient utilizes ammonium or substituted ammonium salt of monoanions or polyanions as the trapping agent which is pre-loaded into the liposome prior to the encapsulation of therapeutic agent. Those trapping agents establish the transmembrane pH gradient and also may form precipitation, aggregation or gelation with the therapeutic agent which serve as the driving force for the active loading of the agents into the liposome. Regarding the pH gradient, it is generally accepted that the pH value difference between the internal and external environment of the liposome is at least greater than one unit. Other methods employed to establish and maintain a pH gradient across a liposome involve the use of an ionophore that can insert into the liposome membrane and transportation across membranes in exchange for protons. Wherein, the active transition metal loading technique utilizing transition metals to drive the uptake of the agents into liposomes via complexation or coordination.

Suitable trapping agents may be anionic, cationic, amphoteric or nonionic active agents include, but are not limited to those containing carboxylate, polyphosphate, sulfonate including long chain alkyl sulfonates and alkyl aryl sulfonates and sulfate. Cationic trapping agents include quaternary ammonium compounds such as benzalkonium chloride, benzethonium chloride, cetrimonium bromide, stearyl dimethylbenzyl ammonium chloride, polyoxyethylene and coconut amine, and the like.

More specific examples of trapping agents include ammonium sulfate, transition metals and ammonium or substituted ammonium salt of the following: polyanionized sulfated cyclodextrin, sulfobutyl ether cyclodextrin, polyanionized sulfated sugar, polyphosphates, and the like.

Specifically, trapping agents include ammonium or substituted ammonium salt of the following polyanionized sulfated sugars: sucrose octasulfate, chondroitin sulfate, dermatan sulfate, keratan sulfate, heparan sulfate and sulfated hyaluronic acid, fucoidan, galactan, carrageenan, rhamnan sulfate, galactofucan, mannoglucuronofucan, arabinogalactans sulfate, mannan sulfate, sulfated heterorhamnan and xylomannan sulfate, and the like.

Specifically, trapping agents include ammonium or substituted ammonium salt of the following forms of sulfobutylether cyclodextrin: sulfobutylether-$\alpha$-cyclodextrin, sulfobutylether-$\beta$-cyclodextrin, and sulfobutylether-$\gamma$-cyclodextrin.

Specifically, trapping agents include ammonium or substituted ammonium salt of the following polyphosphate: phytic acid, triphosphoric acid, polyphosphoric acid and cyclic trimetaphosphate.

Specifically, the counter ion to the above polyanions includes ammonium and substituted ammonium which further includes the protonated form of the following: triethylamine, triethanolamine, tris(hydroxymethyl)aminomethane or tromethamine, diethanolamine, ethylenediamine, tributylamine, 1,4-diazabicyclo[2.2.2]octane, diethylethanolamine, diethanolethylamine, ethanolamine and morpholine.

Transition metal ions-based trapping agents include the salt form of the following: ions of copper, zinc, manganese, nickel and cobalt. The counter ion to the metal includes sulfate, chloride, gluconate, bromide and hydroxide.

More specifically, trapping agents used for drug loading in liposome include the following: ammonium sulfate, triethylammonium sucrose octasulfate (TEA-SOS), triethylammonium sulfobutyl ether beta-cyclodextrin (TEA-SBE-$\beta$-CD); tris(hydroxymethyl)aminomethane salt of sulfobutyl ether-beta-cyclodextrin (Tris-SBE-$\beta$-CD), triethylammonium salt of phytic acid or inositol hexaphosphate (TEA-IP6), copper gluconate, copper sulfate, copper chloride and zinc sulfate.

Passive and active drug loading methods of entrapment may also be coupled in order to prepare a liposome formulation containing more than one encapsulated agent.

5. Administering Compositions of the Invention In-Vivo

As mentioned above, the delivery vehicle compositions of the present invention may be administered to warm-blooded animals, including humans as well as to domestic avian species. For treatment of human ailments, a qualified physician will determine how the compositions of the present invention should be utilized with respect to dose, schedule and route of administration using established protocols. Such applications may also utilize dose escalation should agents encapsulated in delivery vehicle compositions of the present invention exhibit reduced toxicity to healthy tissues of the subject.

Preferably, the pharmaceutical compositions of the present invention are administered parenterally, i.e., intraarterially, intravenously, intraperitoneally, subcutaneously, or intramuscularly. More preferably, the pharmaceutical compositions are administered intravenously or intraperitoneally by a bolus or infusion injection.

In other methods, the pharmaceutical or cosmetic preparations of the present invention can be contacted with the target tissue by direct application of the preparation to the tissue. The application may be made by topical, "open" or "closed" procedures. By "topical", it is meant the direct application of the multi-drug preparation to a tissue exposed to the environment, such as the skin, oropharynx, external auditory canal, and the like. "Open" procedures are those procedures that include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed' procedures are invasive procedures in which the internal target tissues are not directly visualized, but accessed via inserting instruments through small wounds in the skin. For example, the preparations may be administered to the peritoneum by needle lavage. Alternatively, the preparations may be administered through endoscopic devices.

Pharmaceutical compositions comprising delivery vehicles of the invention are prepared according to standard techniques and may comprise water, buffered water, 0.9% saline, 0.3% glycine, 5% dextrose, iso-osmotic sucrose solutions and the like, including glycoproteins for enhanced stability, such as albumin, lipoprotein, globulin, and the like. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and the like. Additionally, the delivery vehicle suspension may include lipid-protective agents which protect lipids against free-radical and lipid peroxidative damages on storage. Lipophilic free-radical quenchers, such as alpha-tocopherol and water-soluble iron specific chelators, such as ferrioxamine, are suitable.

The concentration of delivery vehicles in the pharmaceutical formulations can vary widely, such as from less than about 0.05%, usually at or at least about 2-5% to as much as 10 to 30% by weight and will be selected primarily by fluid volumes, viscosities, and the like, in accordance with the particular mode of administration selected. For example, the concentration may be increased to lower the fluid load associated with treatment. Alternatively, delivery vehicles composed of irritating lipids may be diluted to low concentrations to lessen inflammation at the site of administration. For diagnosis, the amount of delivery vehicles administered will depend upon the particular label used, the disease state being diagnosed and the judgment of the clinician.

Preferably, the pharmaceutical compositions of the present invention are administered intravenously. Dosage for the delivery vehicle formulations will depend on the ratio of drug to lipid and the administrating physician's opinion based on age, weight, and condition of the patient.

In addition to pharmaceutical compositions, suitable formulations for veterinary use may be prepared and administered in a manner suitable to the subject. Preferred veterinary subjects include mammalian species, for example, non-human primates, dogs, cats, cattle, horses, sheep, and domesticated fowl. Subjects may also include laboratory animals, for example, in particular, rats, rabbits, mice, and guinea pigs.

6. Package Kit

The therapeutic agents in the invention compositions may be formulated separately in individual compositions wherein each therapeutic agent is stably associated with appropriate delivery vehicles. These compositions can be administered separately to subjects as long as the pharmacokinetics of the delivery vehicles are coordinated so that the ratio of therapeutic agents administered is maintained at the target for treatment. Thus, it is useful to construct kits which include, in separate containers, a first composition comprising delivery vehicles stably associated with at least a first therapeutic agent and, in a second container, a second composition comprising delivery vehicles stably associated with at least one second therapeutic agent. The containers can then be packaged into the package kit.

The kit will also include instructions as to the mode of administration of the compositions to a subject, at least including a description of the ratio of amounts of each composition to be administered. Alternatively, or in addition, the kit is constructed so that the amounts of compositions in each container is pre-measured so that the contents of one container in combination with the contents of the other represent the correct ratio. Alternatively, or in addition, the containers may be marked with a measuring scale permitting dispensation of appropriate amounts according to the scales visible. The containers may themselves be useable in administration; for example, the kit might contain the appropriate amounts of each composition in separate syringes. Formulations which comprise the pre-formulated correct ratio of therapeutic agents may also be packaged in this way so that the formulation is administered directly from a syringe prepackaged in the kit.

Definitions

Unless defined otherwise, all terms of art, notations and other scientific terms or terminology used herein have the same meaning as is commonly understood by one of ordinary skill in the art to which this invention belongs. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a," "an," and "the" include plural reference, and vice versa, any plural forms include singular reference, unless the context clearly dictates otherwise.

The term "about" or "approximately", unless otherwise defined, generally includes up to plus or minus 10% of the indicated number. For example, "about 10%" may indicate a range of 9% to 11%, and "about 20" may mean from 18 to 22. Sometimes preferably, "about" includes up to plus or minus 5% of the indicated value. Alternatively, "about" includes up to plus or minus 5% of the indicated value. When "about" is used before a range, it is applicable to both the lower end and the upper end of the range.

The term "substantially" as herein used means "for the most part" or "essentially", as would be understood by a person of ordinary skill in the art, and if measurable quantitatively, refers to at least 90%, preferably at least 95%, more preferably at least 98%.

The terms "comprising," "having," "including," and "containing," or the like, are to be construed as open-ended terms (i.e., meaning "including, but not limited to,") unless otherwise noted.

As used herein, the term "synergistic effect" means an interaction between two or more drugs that causes the total effect of the drugs to be greater than the sum of the individual effects of each drug.

By "synergistic ratio" is meant the molar ratio of two or more drugs used in combination at which a synergistic effect can be obtained.

As used herein, the term "synergistic cytotoxic effect" refers an interaction between two or more drugs that causes the total effect of the drugs to be greater than the sum of the individual effects of each drug. This total effect results in cell kill and eventual tumor shrinkage.

As used herein, the term "synergistic cytostatic effect" refers an interaction between two or more drugs that causes the total effect of the drugs to be greater than the sum of the individual effects of each drug. This total effect results in tumor growth inhibition without direct cell killing.

The term "additive effect" means the combined effect produced by the action of two or more drugs, being equal to the sum of their separate effects.

By "additive ratio" is meant the molar ratio of the two or more drugs used in combination at which an additive effect can be obtained.

The term "non-antagonistic ratio" refers to both synergistic ratio and additive ratio.

As used herein, the term "antagonistic effect" means a therapeutic response to exposure to two or more drugs that is less than would be expected if the known effects of the individual drugs were added together.

The term "antagonistic ratio" as used herein refers to molar ratio of two or more drugs used in combination at which an antagonistic effect can be obtained.

The term "combination index" refers to a parameter that is used to determine the degree of drug interaction. Combination Index (CI) can be calculated based on the median-effect analysis algorithm as described by Chou and Talalay (Adv. Enzyme Reg. (1984), 22:27-55). A CI value<0.9 indicates synergistic drug interactions; a value $0.9 \leq CI \leq 1.1$ reflects additive effect and a $CI > 1.1$ indicates antagonistic effect.

The term "fraction affected" refers to the faction of cells that is affected by a particular drug dose on their growth in an in vitro assay. Fraction affected is used to calculated combination index as described by Chou and Talalay (Adv. Enzyme Reg. (1984), 22:27-55).

By "relevant" cells refer to at least one cell culture or cell line which is appropriate for testing the desired biological effect. As these agents are used as antineoplastic agents, "relevant" cells are those of cell lines identified by the Developmental Therapeutics Program (DTP) of the National Cancer Institute (NCI)/National Institutes of Health (NIH) as useful in their anticancer drug discovery program. Currently the DTP screen utilizes 60 different human tumor cell lines. The desired activity on at least one of such cell lines would need to be demonstrated.

By "tumor homogenate" refers to cells generated from the homogenization of patient biopsies or tumors. Extraction of whole tumors or tumor biopsies can be achieved through standard medical techniques by a qualified physician and homogenization of the tissue into single cells can be carried out in the laboratory using a number of methods well-known in the art.

The term "trapping agent" as used herein refers to a chemical compound that is presented within the aqueous compartment of the liposome and is used to entrap and retain one or more drugs within the same location within the liposome.

The term "liposome" refers to a spherical-shaped vesicle that is composed of one or more phospholipid bilayers, which closely resembles the structure of cell membranes.

The phrase "unilamellar vesicles" as used herein refers to spherical vesicles comprised of one lipid bilayer membrane which defines a single closed aqueous compartment. The bilayer membrane is composed of two layers of lipids: an inner layer and an outer layer. Lipid molecules in the outer layer are oriented with their hydrophilic head portions towards the external aqueous environment and their hydrophobic tails pointed downward toward the interior of the liposome. The inner layer of the lipid lays directly beneath the outer layer, the lipids are oriented with their heads facing the aqueous interior of the liposome and their tails towards the tails of the outer layer of lipid.

The phrase "multilamellar vesicles" as used herein refers to liposomes that are composed of more than one lipid bilayer membrane, which membranes define more than one closed aqueous compartment. The membranes are concentrically arranged so that the different membranes are separated by aqueous compartments, much like an onion.

By "chemotherapeutic agent" is meant a drug substance that is useful for the treatment of cancer. A chemotherapeutic agent is also known as cytotoxic agent, the effect which results in cell kill and eventual tumor shrinkage. A chemotherapeutic agent may be administered with a curative intent or to prolong life or to palliate symptoms. A chemotherapeutic agent may be administered in conjunction with other cancer treatments such as radiation therapy or surgery.

By "protein kinase inhibitors" is meant a large group of unique and potent antineoplastic agents which specifically target protein kinases that are altered in cancer cells and that account for some of their abnormal growth. The effect of protein kinase inhibitors is usually cytostatic, which means tumor growth is inhibited without direct cell killing. Therefore, protein kinase inhibitors are less toxic and in the right patient population, protein kinase inhibitors are more potent than conventional chemotherapeutic agents.

By "release" is meant that the drug encapsulated in a liposome passes through the lipid membrane constituting the liposome and then exits to the outside of the liposome.

The term "encapsulation" as used herein, refers to encircling an internal phase typically resulting in an interior cavity separated from an external media. The components of the internal phase/interior cavity are thus "encapsulated" as described herein. As described herein, the encircled, or encapsulated, internal phase is an aqueous phase. The amount of therapeutic drug that is loaded into the interior cavity of the liposome and therefore unavailable to the external media until the liposome is triggered from release would be considered as "encapsulated" within the liposome.

The phrase "co-encapsulation" and "co-encapsulated" as used herein, refers to the situation where two or more therapeutic agents are encapsulated within the liposome.

The term "passive loading" as used herein, refers to a drug loading technique used in liposome drug product preparation. In one scenario, passive loading can be achieved by encapsulating the therapeutic agent during the liposome formation. In another scenario, passive loading involves passive drug equilibration after the formation of liposomes. In both cases above, the therapeutic agent is loaded within the aqueous compartment of the liposome.

The phrase "active loading" as used herein refers to a drug loading technique used in liposome drug product preparation. The commonly used active loading methods in the art include the transmembrane pH gradient loading technique and transition metal loading technique. The former one utilizes an ammonium or a substituted ammonium salt of monoanion or polyanions as the trapping agent which is pre-loaded into the liposome prior to the encapsulation of therapeutic agent. Based on the equilibrium as determined by the pH gradient, the therapeutic agent can "actively" diffuse into the aqueous compartment of the liposome, interact with the pre-loaded trapping agent through the formation of precipitation, aggregation, or gelation, which serves as another driving force to encapsulate the therapeutic agent inside the liposome. The transition metal-based loading technique utilizes transition metals to drive the uptake of the agents into liposomes via complexation or coordination. Overall, a much higher encapsulation efficiency of the therapeutic agent can be achieved (e.g., >90%) by using the active loading technique as compared to that obtained from the passive loading technique.

The term "mean particle size" refers to the average diameter of the liposome. This can be measured by instrument based on dynamic light scattering.

The term "substituted ammonium" means that the hydrogen atoms in the ammonium ion are substituted with one or more alkyl group or some other organic group to form a substituted ammonium ion.

The term "triple negative breast cancer" refers to a type of breast cancer from which the cancer cells do not have estrogen or progesterone receptors, and also do not make too much of the protein called human epidermal growth factor receptor 2 (HER2). Namely, the cells test "negative" on all three tests of the above receptors.

The term "drug-resistant cancer" refers to the type of cancer that show resistance to the given therapeutic agents. Drug resistance occurs when cancer cells don't respond to a drug that is usually able to kill or weaken them. Drug resistance may be present before treatment is given (intrinsic resistance) or may occur during or after treatment with the drug (acquired resistance). In cancer treatment, there are many things that may cause resistance to anticancer drugs. For example, DNA changes or other genetic changes may change the way the drug gets into the cancer cells or the way the drug is broken down within the cancer cells. Drug resistance can lead to cancer treatment not working or to the cancer coming back.

The term "effective amount" refers to the amount necessary or sufficient to realize a desired biologic or therapeutic effect.

The term "therapeutically effective amount" means an amount effective to deliver a therapeutically effective amount of an amount of active agent needed to delay the onset of, inhibit the progression of, or halt altogether the particular disease, disorder or condition being treated, or to otherwise provide the desired effect on the subject to be treated. As one of ordinary skill in the art would understand, a therapeutically effective amount varies with the patient's age, condition, and gender, as well as the nature and extent of the disease, disorder or condition in the patient, and the dosage may be adjusted by the individual physician (or veterinarian).

The term "pharmaceutically acceptable" describes a material that is not biologically or otherwise undesirable, i.e. without causing an unacceptable level of undesirable biological effects or interacting in a deleterious manner The terms "treating" and "treatment", or the like, refer to reversing, alleviating, inhibiting, or slowing the progress of the disease, disorder, or condition to which such terms apply, or one or more symptoms of such disease, disorder, or condition.

The term "subject" or "patient" used herein refers to a human patient or a mammalian animal, such as cat, dog, cow, horse, monkey, or the like.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

The Following Abbreviations are Used:

APIs: active pharmaceutical ingredients
DOX: doxorubicin
IMT: imatinib
SUN: sunitinib
GEM: gemcitabine
DOX-L: liposome encapsulated with doxorubicin
IMT-L: liposome encapsulated with imatinib
SUN-L: liposome encapsulated with sunitinib
GEM-L: liposome encapsulated with gemcitabine
DOX/IMT-L: liposome encapsulated with doxorubicin and imatinib
DOX/SUN-L: liposome encapsulated with doxorubicin and sunitinib
GEM/SUN-L: liposome encapsulated with gemcitabine and sunitinib
mPEG-2000-DSPE, Sodium salt: N-(Carbonyl-methoxy-polyethylenglycol-2000)-1,2-distearoyl-sn-glycero-3-phosphoethanolamine Sodium
DSPC: 1,2-distearoyl-sn-glycero-3-phosphocholine
DMPC: 1,2-dimyristoyl-sn-glycero-3-phosphocholine
DPPC: 1,2-dipalmitoyl-sn-glycero-3-phosphocholine
DSPG: 1,2-Distearoyl-sn-glycero-3-phosphoglycerol
HSPC: L-α-phosphatidylcholine, hydrogenated
PG: phosphatidylglycerol
Chol: cholesterol
SUV: small unilamellar vesicle
LUV: large unilamellar vesicle MLV: multilamellar vesicle
MTT: 3-(4,5-dimethylthiazol-2-yl)-2,5-diphenyl-2-H tetrazolium bromide
TEA: triethylamine
TEA-SOS: triethylammonium sucrose octasulfate
TEA-SBE-β-CD: triethylammonium sulfobutylether-β-cyclodextrin
Tris-SBE-β-CD: tris(hydroxymethyl) aminomethane sulfobutylether-β-cyclodextrin
SBE-β-CD: sulfobutylether-β-cyclodextrin
EDTA: ethylenediaminetetraacetic acid
HEPES: N-2-hydroxyethyl-piperazine-N-2-ethanesulfonic acid
$ED_{75}$ and $ED_{90}$: effective dose required to affect 75 and 90% of the cells in cell culture
CI: combination index
Fa: fraction affected
MS: HEPES buffered saline (20 mM HEPES, 150 mM NaCl, pH 7.4)
SHE: 300 mM sucrose, 20 mM HEPES, 30 mM EDTA

EXPERIMENTAL METHODS

Materials

Doxorubicin hydrochloride (DOX), imatinib mesylate (IMT), and sunitinib malate (SUN), ammonium sulfate, sucrose octasulfate (SOS) sodium and SBE-β-cyclodextrin sodium salt, were purchased from Sigma-Aldrich Co. (St Louis, MO, USA). Hydrogenated Soy Phosphatidylcholine (HSPC), 1,2-distearoyl-sn-glycero-3-phosphocholine (DSPC), Distearoylphosphatidylglycerol (DSPG), N-(Carbonyl-methoxypolyethylenglycol-2000)-1,2-distearoyl-sn-glycero-3-phosphoethanolamine (mPEG-2000-DSPE, Na-salt), and cholesterol were purchased from Lipoid GmbH. Other reagents were obtained as follows ammonium sulfate, 3-(4,5-dimethylthiazol-2-yl)-2,5-diphenyl-tetrazolium bromide (MTT), and coumarin-6 from Sigma-Aldrich Co. (St Louis, MO, USA). All other chemicals used during the study were reagent-grade and were used with no further purification.

Cancer Cell Lines

Human breast adenocarcinoma cell line (e.g., MDA-MB-231), Ewing sarcoma cell line with a type 2 EWS-FLI-1 fusion (e.g., SK-ES-1), a type 1 EWS-FLI-1 fusion cell line (e.g., A-673), melanoma cancer cell lines that show intrinsic resistance to doxorubicin (e.g., SK-MEL-28), triple-negative breast cancer cell lines that show intrinsic resistance to doxorubicin cell line (e.g., BT-549), breast cancer cell lines (e.g., MCF-7), non-small cell lung cancer (NSCLC) cell lines (e.g., A-549), GIST with KIT mutation: heterozygous exon 11, V560-Y579 deletion cell lines (e.g., GIST-T1), and colorectal adenocarcinoma cell lines (e.g., HT-29) were obtained from the Cell Bank in the USA.

Development of DOX-Resistant MDA-MB-231 and MCF-7 Cell Lines

Doxorubicin resistant cell lines of MDA-MB-231 and MCF-7 were developed in house. The resistant variants were generated by repeatedly culturing MDA-MB-231 and MCF-7 cells in the presence of 0.2 µmol/L DOX. These cells that proliferated well in the presence of doxorubicin after several passages qualified as DOX-resistant MDA-MB-231 and MCF-7 cells, which were named as MDA-MB-231(R) and MCF-7(R) cell lines, respectively. Both MDA-MB-231 (R) and MCF-7(R) cell lines were characterized against non-DOX treated MDA-MB-231 and MCF-7 cell lines.

Liposome Preparation

The general solo and combined drug liposome preparation methods are described below.

Active pH gradient drug loading method: For example, the coloaded doxorubicin/imatinib (DOX/IMT-L) and doxorubicin/sunitinib liposome (DOX/SUN-L) were prepared by hydration/extrusion, dialysis, and remote pH gradient loading. Briefly, mPEG-2000-DSPE or DSPG, cholesterol, and DSPC or HSPC were dissolved in organic solvents and hydrate in the selected aqueous trapping agent solution (e.g., ammonium sulfate, TEA-SOS, TEA-SBE-β-CD aqueous solution, polyphosphate ions, others) at about 50-70° C. The organic phase was slowly injected into the aqueous phase, and vigorously stirred for approximately 30 minutes to allow for emulsification. The emulsion was subjected to extrusion with multiple 50-100 nm membranes at about 50-70° C. to obtain desired liposome particle size and particle size distribution and cooled in an ice bath to yield unloaded liposome. The external trapping agent outside liposome was washed away by diffusion across a dialysis membrane. The unloaded liposome suspension was diluted by sucrose buffer and heated to about 50-70° C. Add the combined drug, such as doxorubicin/imatinib or doxorubicin/sunitinib, into the warm unloaded liposome suspension and heated for 45 minutes to obtain coloaded combo-drug DOX/IMT liposome (DOX/IMT-L) or DOX/SUN liposome (DOX/SUN-L), respectively. For the preparation of each individual drug DOX-L, IMT-L, and SUN-L liposomes, the above procedures were reproduced precluding the addition of mixed drug regimen DOX/IMT or DOX/SUN, respectively.

Active transition metal ion drug loading method: For example, the coloaded doxorubicin/imatinib (DOX/IMT-L) and doxorubicin/sunitinib liposome (DOX/SUN-L) were prepared by hydration/extrusion, dialysis, and remote active loading with transition metal ion copper gluconate. Briefly, mPEG-2000-DSPE or DSPG, cholesterol, and DSPC or HSPC were dissolved in organic solvents and hydrate in the selected aqueous trapping agent solution consisting of 100 mM Cu (gluconate), 220 mM triethanolamine (TEA), pH 7.4, at about 50-70° C. The organic phase was slowly injected into the aqueous phase, and vigorously stirred for approximately 30 minutes to allow for emulsification. The emulsion was subjected to extrusion with multiple 50-100 nm membranes at about 50-70° C. to get the desired liposome particle size and particle size distribution and cooled in an ice bath to yield unloaded liposome. The external trapping agent outside liposome was washed away by diffusion across a dialysis membrane. The unloaded liposome suspension was diluted by sucrose buffer and heated to about 50-70° C. Add the premixed combined drug substances, such as doxorubicin/imatinib or doxorubicin/sunitinib, into the warm unloaded liposome suspension and heated for 45 minutes to obtain coloaded combo-drug DOX/IMT liposome (DOX/IMT-L) or DOX/SUN liposome (DOX/SUN-L), respectively. For the preparation of each individual drug, DOX-L, IMT-L, and SUN-L liposomes, the above procedures were reproduced precluding the addition of mixed drug regimen DOX/IMT or DOX/SUN, respectively.

Characterization of Liposomes

Particle Size and Zeta ζ-Potential: Dynamic Light Scattering (DLS) was used to record the hydrodynamic particle size, polydispersity index (PDI), and zeta ζ-potential of combined drug liposome and individual drug liposome using a Nano-S90 ZetaSizer (Malvern Instruments, UK). All experiments were performed in triplicate, at a scattering angle of 90° and a temperature of 25° C. Each sample was adequately diluted with distilled water prior to measurement, and three measurements were performed for each sample.

Morphological Characterization: Cryo-Transmission electron microscopy (Cryo-TEM) was employed to examine the size and morphology of the coloaded liposome. A drop of the formulation was deposited onto a copper grid coated with a carbon film, and the particles were subjected to negative staining by 2% (w/v) phosphotungstic acid. The sample was then appropriately dried under mild to moderate infrared radiation and observed under an H7600 transmission electron microscope (Hitachi, Tokyo, Japan).

Drug Loading and Encapsulation: Drug content (Assay) and encapsulation efficiency (EE %) of the liposomes were determined by dissolving a known quantity of loaded liposome in Triton-100 aqueous solution and quantifying each encapsulated drug by HPLC-UV analysis. Drug encapsulation efficiency was measured after liposome suspension elute through a Sephadex G-50 spin column. Then, drug loading efficiency were determined using HPLC-UV analysis. Encapsulation efficiency percentage (EE %) was calculated as percentage of total drug content minus the free drug content, then divided the total amount drug content.

In-Vitro Drug Release Study

For example, in-vitro release of DOX and/or IMT from DOX/IMT-L, DOX-L, and IMT-L were evaluated at pH 6.8 by dialysis. A sample of liposomes under current study (~1-2 mL) was placed in a dialysis bag (molecular weight cutoff 50 kDa), which was pre-hydrated overnight in phosphate-buffered saline (PBS) at pH 6.8. The dialysis bag was clipped at both ends, dipped in a 200 mL dissolution vessel of with 150 mL PBS (pH 6.8) at 200 rpm stirring and a temperature in a range of 37-48° C. Aliquots (~1 mL) of the release media were sampled at predetermined time intervals and replaced with equal volumes of fresh media. The DOX and IMT content in each sample was determined by HPLC-UV method.

In-vitro Cytotoxicity Study

Optimization of the Drug Combination. For example, effects of varying the molar ratio of DOX and IMT in DOX/IMT-L on the proliferation of MDA-MB-231(R) or MCF-7(R) cells were studied to determine the optimal combination ratio for the drugs in liposome. For this purpose, DOX/IMT-L containing DOX and IMT in molar ratios of 1:1, 1:5, and 1:10 were prepared along with DOX-L and IMT-L. MDA-MB-231(R) and MCF-7(R) cells were seeded separately in 96-well plates ($1 \times 10^4$ cells per well) in high-glucose DMEM supplemented with 10% FBS and incubated overnight at 37° C. The medium was removed from each well, and the above formulations were added in appropriate dilutions so that the final concentration of DOX/IMT-L as a total drug concentration in each well was uniform at 0.5 μg/mL. The viable cells in each well after 48 hours of incubation were determined as per protocol described for the MTT Assay below. DOX/IMT-L coloaded with DOX and IMT in the so-determined optimal molar combinations were utilized for further studies.

MTT Assay

The cell seeded plate was incubated for 24 hours at 37° C. and 5% $CO_2$ in a standard cell culture incubator before drug treatment. The following day, drug dilutions on either solo drug or drug combinations at defined molar drug ratios were prepared using respective cell culture media. The previous cell culture media in the 96-well plate was then replaced by fresh media containing the drugs. After another 24 hours of incubation, cell viability was assessed by the MTT assay following the manufacture's protocols. Relative percent survival was determined by subtracting absorbance values obtained by media-only wells from drug treated wells and then normalizing to the no-drug control wells (cell only control). The fraction of cells affected (Fa), or cell growth inhibition (%) at each drug concentration was subsequently calculated for each well. The effect of drug combinations was then calculated and processed by a software CompuSyn for drug synergy analysis. The program employs the median-effect analysis algorithm, which produces the Combination Index (CI) value as a quantitative indicator of the degree of synergy. Based on this analysis method, a CI<0.9 indicates synergy, a $0.9 \leq CI \leq 1.1$ reflects additive effect and a CI>1.1 indicates antagonism. CI plots are typically illustrated with CI representing the y-axis versus the proportion of cells affected, or fraction affected (Fa), on the x-axis.

In-Vivo Antitumor Study

Development of SK-MEL-28 Xenograft Models. Six-week-old female mice (BALB/c Nude) were inoculated subcutaneously at the right flank of the mice with $10 \times 10^6$ SK-MEL-28 tumor cells for tumor development. The inoculated tumor was then allowed to grow for about five weeks prior to initiation of the treatment. Mice were organized into appropriate treatment groups consisting of saline control and drug treated groups including (1) PEGylated DOX-L (2) PEGylated IMT-L (3) DOX/IMT premixed free drug cocktail solution (DOX:IMT molar ratio of 1:5) and (4) PEGylated DOX/IMT-L (DOX:IMT molar ratio of 1:5). Mice were injected intravenously with the required volume of sample to administer the targeted dose (6 mg/kg DOX, 27.3 mg/kg IMT) to the animals based on the weight of each individual mice each week for two-five weeks. The tumor volume and mice weight are measured and monitored.

Drug Administration and Data Collection

For example, five of the above six groups of xenograft mice were subjected to intravenous (i.v.) administration of saline solution (control), PEGylated DOX-L, free premixed DOX/IMT cocktail, PEGylated DOX-L, PEGylated IMT-L, and PEGylated DOX/IMT-L in the tail vein. Each formulation, in a dose equivalent to 6 mg DOX/kg and 27.3 mg IMT/kg mouse body weight, was administered each week for two-five weeks. Tumor dimensions and body weights of the mice were evaluated at predetermined times. Respective tumor volumes were calculated based on the formula: volume=½×(longest dimension)×(shortest dimension).

Statistical Analysis

Statistical differences between the combined drug liposome treated group and other treatment groups during MTT assay and in-vivo antitumor study were determined by one-way ANOVA combined with Dunnett's test at the significance level of p<0.05. All observations were expressed as mean±SD (n=3).

EXAMPLES

Figure 1:
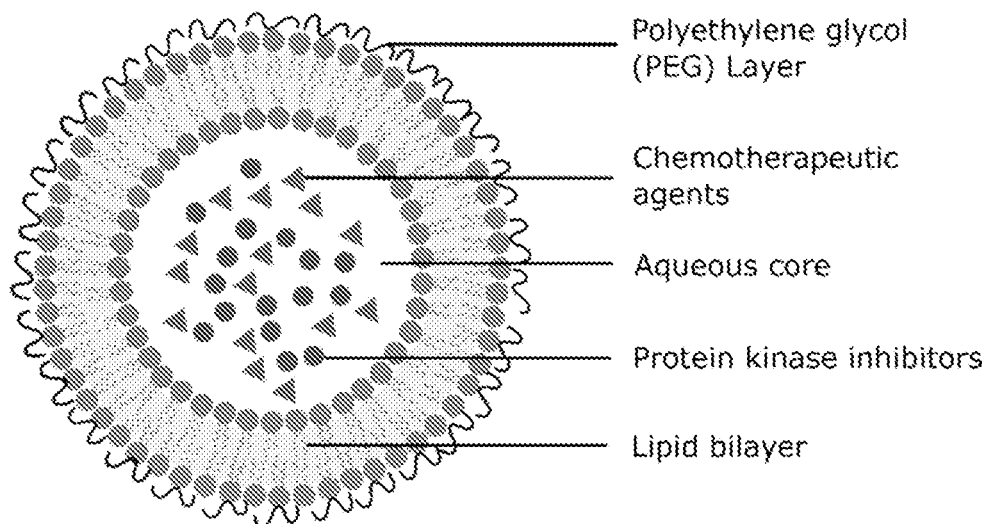
FIG. 1 illustrates the examples of combined anti-cancer drug coloaded PEGylated liposome (A) and DSPG Liposome (B). In the PEGylated liposomes, mPEG-2000-DSPE was used to provide the steric stabilization to the vesicles. On the other hand, in the DSPG liposomes, negatively charged DSPG was employed to stabilize the liposome through electrostatic repulsion. Both of the chemotherapeutic drug and protein kinase inhibitor are coloaded in the aqueous core compartment of the liposomes.
Figure 1:
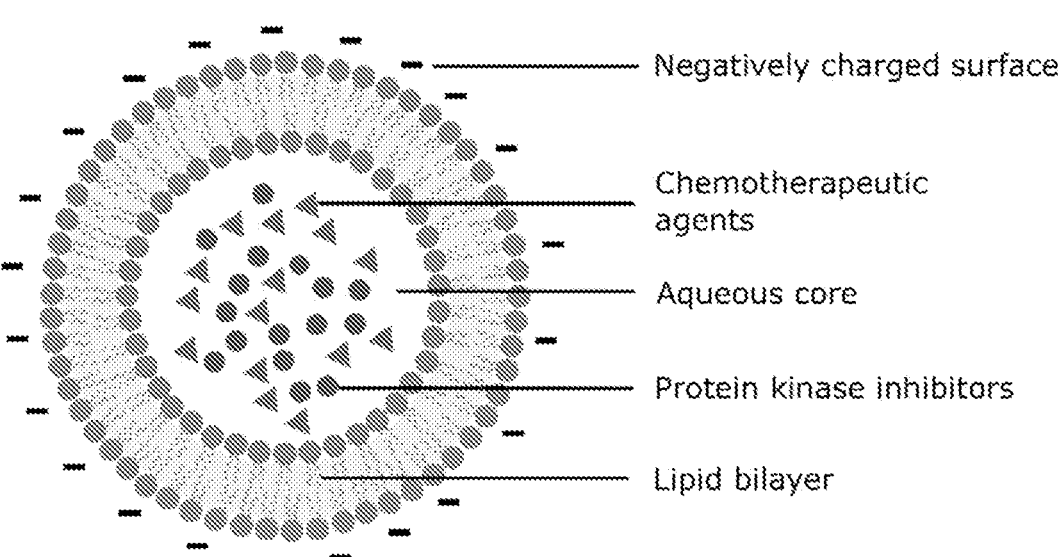
Figure 2:
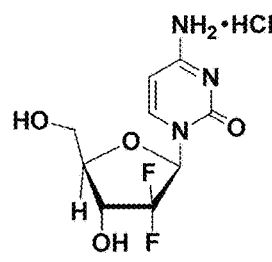
FIG. 2 lists the chemical structures of (A) Doxorubicin hydrochloride (DOX), (B) Imatinib mesylate (IMT), (C) Sunitinib malate (SUN), and (D) Gemcitabine hydrochloride (GEM).

The examples of scheme of the dual drug loaded liposome with chemotherapeutic agent and protein kinase inhibitor are shown in FIGS. 1A and 1B. The chemical structures of the preferred compounds doxorubicin hydrochloride, imatinib mesylate, sunitinib malate, and gemcitabine hydrochloride are shown in FIG. 2 (A, B, C, D).

Example 1

Method of DOX/IMT Liposome Preparation

The liposomes DOX-L, IMT-L, and DOX/IMT-L were prepared by combining emulsification, extrusion, dialysis, and active remote loading as described in Experimental Methods section. The preliminary experiments were conducted to identify and optimize the major factors in formulation and production process conditions (such as lipid selection, composition of liposome, drug to lipid ratio, trapping agent, process conditions, etc.) that affect liposome particle size, particle size distribution, encapsulation efficiency, liposome stability, drug release profile, and other physicochemical properties of liposome.

Example 2

Figure 3:
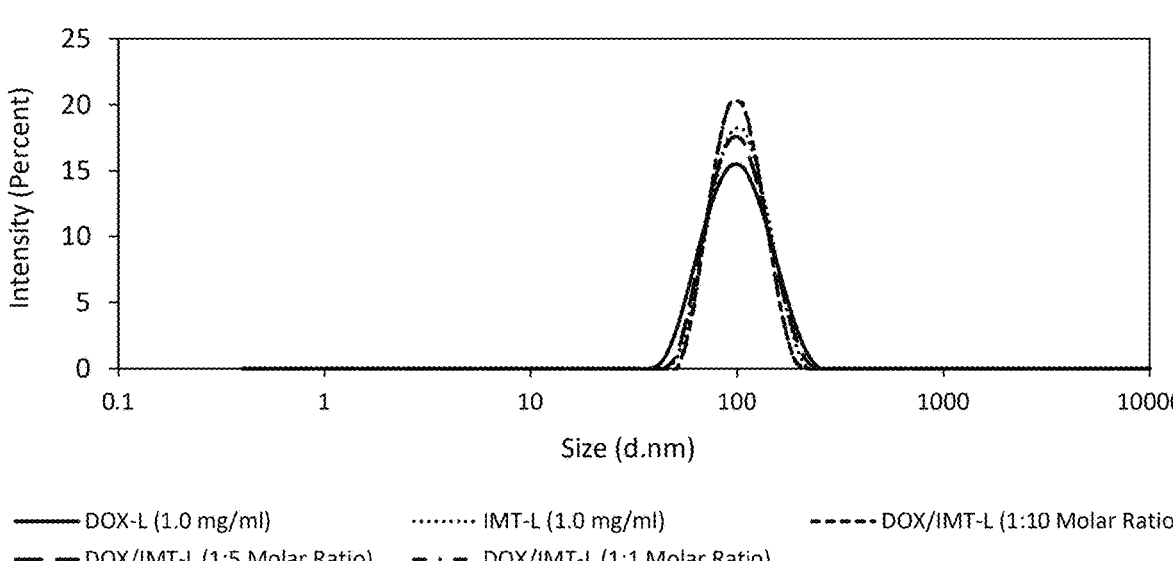
FIG. 3 illustrates the particle size distribution (Intensity %) of PEGylated DOX-L, IMT-L, and DOX/IMT-L at 1:10, 1:5, and 1:1 molar ratios with $(NH_4)_2SO_4$ as trapping agent.
Figure 4:
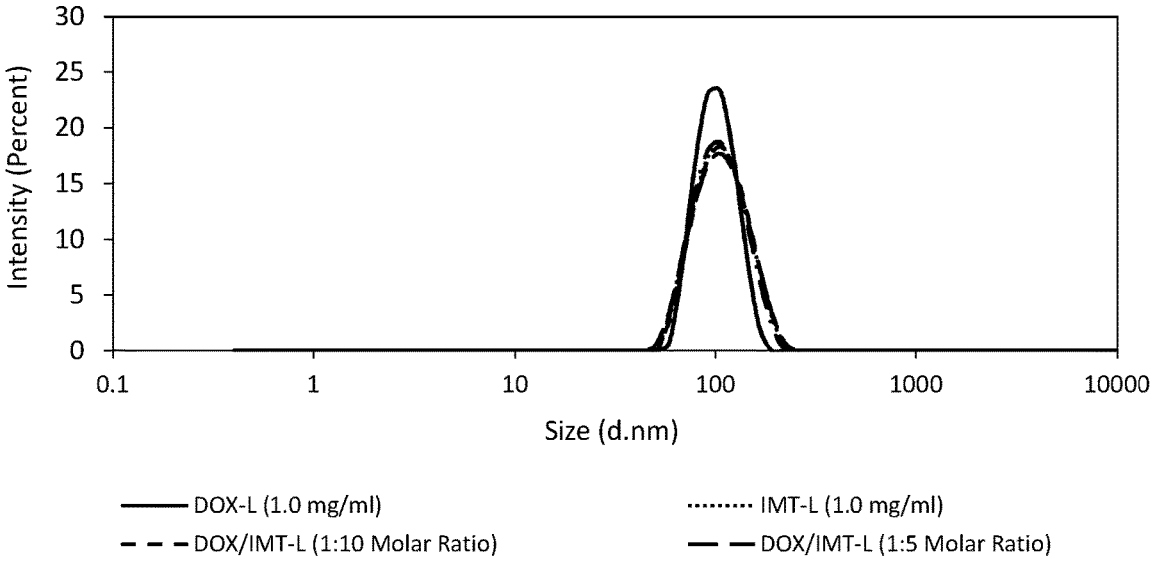
FIG. 4 illustrates the particle size distribution (Intensity %) of DSPG DOX-L, IMT-L, and DOX/IMT-L at 1:10 and 1:5 molar ratios with TEA-SBE-β-CD as trapping agent.

Physicochemical Characterization of DOX/IMT-L with $(NH_4)_2SO_4$ as Trapping Agent Physicochemical characterization was performed with the DOX-L, IMT-L, DOX/IMT-L nanoparticles. Liposomes containing doxorubicin and imatinib were generated using DSPC/mPEG-2000-DSPE/Cholesterol (PEGylated liposome) or DSPG/DSPC/Cholesterol (DSPG liposome) with pH remote loading trapping agent ammonium sulfate $(NH_4)_2SO_4$ to actively load doxorubicin and/or imatinib to form DOX-L, IMT-L, and DOX/IMT-L liposomes. The final PEGylated DOX-L, IMT-L, DOX/IMT-L liposomes showed the following parameters: mean particle size ~100 nm, PDI<0.100 (see FIG. 3), encapsulation efficiency %>95.0%, and surface ζ-Potential<−25 mV (see Table 1). In addition, the final DSPG DOX-L, IMT-L, DOX/IMT-L liposomes showed the following parameters: mean particle size ~100 nm, PDI<0.100 (see FIG. 4), encapsulation efficiency %>95.0%, and surface ζ-Potential<−30 mV. The comparison of PEGylated liposome and DSPG liposome showed in Table 2 demonstrated similar mean particle sizes and encapsulation efficiency for both liposome compositions. The nanocarrier liposome with particle sizes <200 nm ideally exhibits preferential accumulation at tumor sites due to leaky tumoral vasculature, which along with prolonged circulation of the nanoparticle system forms the core of passive tumor targeting by EPR. PEGylation of the current liposome platforms afforded the required prolonged circulation by avoiding reticuloendothelial clearance. Furthermore, capability of the liposome nanocarriers to accommodate a high payload ensured delivery of ample amounts of the drug to the tumor site. The moderate surface charge from DSPG also exhibited by the nanocarriers conferred suitable physical and physiological stability of the system in circulation.

Figure 5:
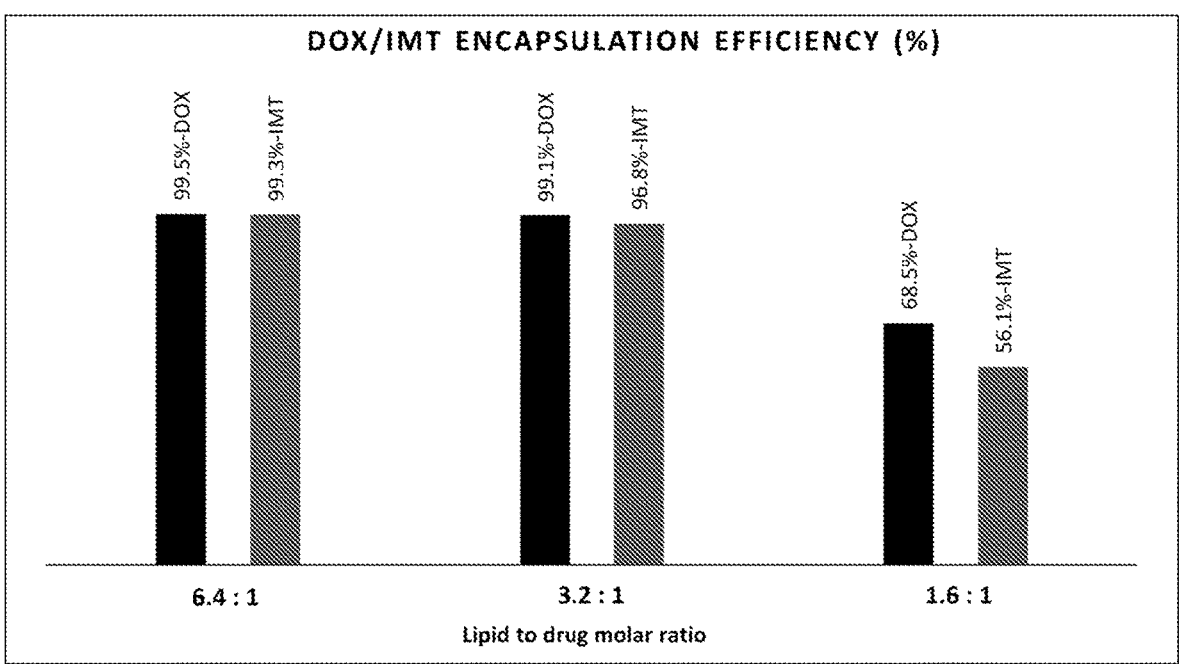
FIG. 5 illustrates the effect of lipid to drug molar ratio on encapsulation efficiency (EE %) of PEGylated DOX-L and IMT-L with $(NH_4)_2SO_4$ as trapping agent.

The effect of total drug to total lipid ratio on drug loading capacity and encapsulation efficiency is shown in FIG. 5. With ammonium sulfate trapping agent at the fixed lipid concentration (8 mg/mL), the drug loading capacity and encapsulation efficiency % are >95% when the total lipid to total drug ratio in the range 6.4:1 to 3.2:1 (molar ratio). However, the encapsulation efficiency dropped to 50-70% around at 1.6:1 total lipid to total drug ratio (molar ratio).

Figure 6:
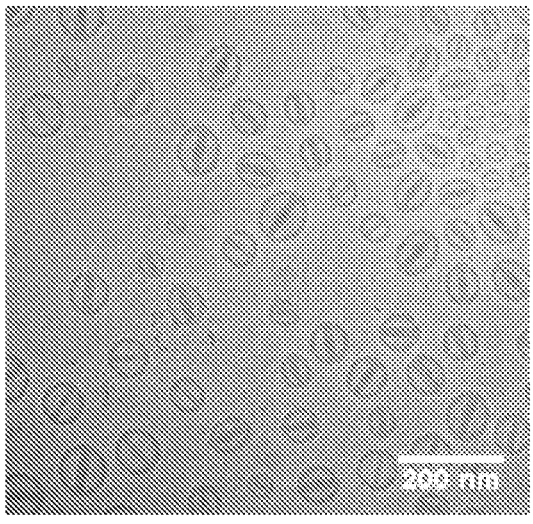
FIG. 6 shows a Cryo-Transmission Electron Microscopy (Cryo-TEM) image of DOX/IMT-L with $(NH_4)_2SO_4$ as trapping agent.

For the DOX/IMT-L liposome (6.4:1 total lipid to total drug molar ratio) with ammonium sulfate trapping agent, the TEM images revealed that the liposome nanoparticles were spherical with a dense core (precipitates of DOX and IMT) and sizes of ~100 nm (FIG. 6). Those results confirmed that the drugs were well co-encapsulated in the aqueous core compartment of the liposome in an amorphous or molecularly dispersed state.

TABLE 1

Effect on Mean Particle Size/Particle Size Distribution (PDI) and Zeta
($\zeta$) Potential (surface charge), and Encapsulation
Efficiency (EE %) of PEGylated DOX-L, IMT-L, and DOX/IMT-L with
$(NH_4)_2SO_4$ Used as the Trapping Agent

| Sample Name | Drug Content | Mean Particle | Particle Size Distribution | $\zeta$-Potential | EE % | |
|---|---|---|---|---|---|---|
| (DOX/IMT molar ratio) | (mg/mL) | Size (nm) | (PDI) | (mv) | DOX | IMT |
| DOX-L | 1.0 | 94.39 | 0.079 | −24.9 | 99.1 | — |
| IMT-L | 1.0 | 98.17 | 0.087 | −27.4 | — | 99.5 |
| DOX/IMT-L 1:10 | 0.09 (DOX) 0.91 (IMT) | 103.1 | 0.08 | −26.5 | 96.0 | 99.2 |
| DOX/IMT-L 1:5 | 0.17 (DOX) 0.84 (IMT) | 101.7 | 0.081 | −29.9 | 97.5 | 99.4 |
| DOX/IMT-L 1:1 | 0.5 (DOX) 0.5 (IMT) | 99.98 | 0.063 | −27.8 | 98.8 | 99.6 |

TABLE 2

Effect of PEGylated and DSPG Liposome on Particle Size/Particle Size Distribution
(PDI), Zeta Potential, and Encapsulation Efficiency % (EE %) on DOX/IMT Liposomes.

| Sample Name | Mean Particle Size (nm)/PDI | | $\zeta$-Potential (mv) | | EE % | |
|---|---|---|---|---|---|---|
| | mPEG-2000-DSPE | DSPG | mPEG-2000-DSPE | DSPG | mPEG-2000-DSPE | DSPG |
| DOX-L (1 mg/mL) | 94.39/0.08 | 101.4/0.076 | −24.9 | −30.4 | 99.1 (DOX) | 99.2 (DOX) |
| IMT-L (1 mg/mL) | 98.17/0.09 | 100.2/0.086 | −27.4 | −30.1 | 99.5 (IMT) | 99.5 (IMT) |
| DOX/IMT-L 0.5 mg/mL (DOX) 0.5 mg/mL (IMT) | 99.98/0.06 | 100.8/0.073 | −27.8 | −30.2 | 98.8 (DOX) 99.6 (IMT) | 99.1 (DOX) 99.4 (IMT) |

Example 3

Figure 7:
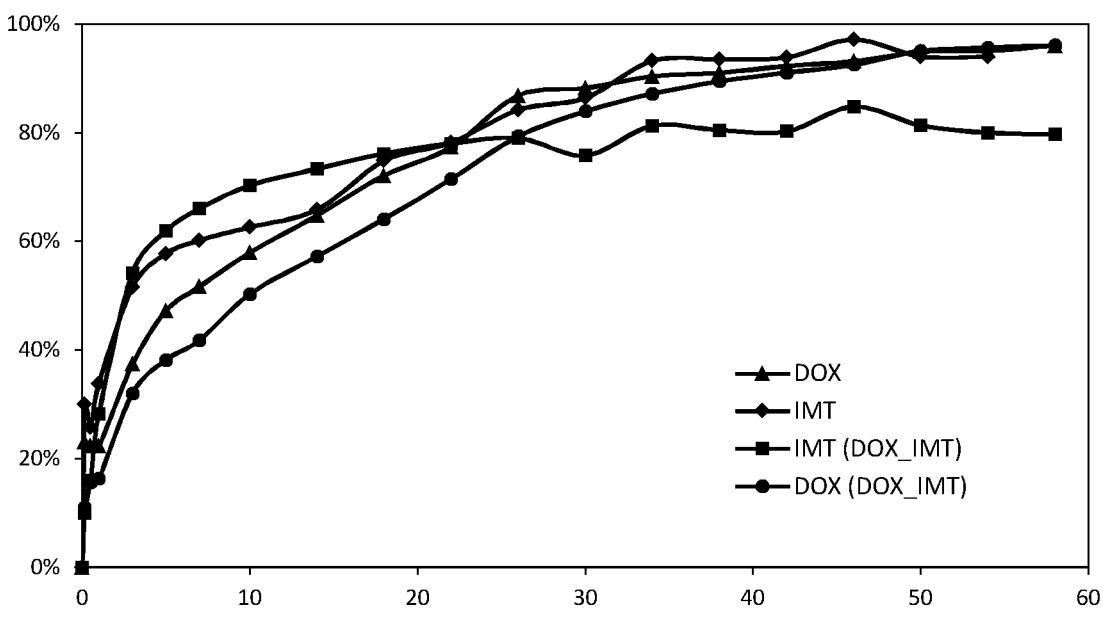
FIG. 7 illustrates the comparison of in-vitro dissolution drug release profiles of doxorubicin and imatinib from solo drug loaded PEGylated DOX-IMT-L liposome with (NH4)2SO4 liposomes, i.e., DOX-L (triangle) and IMT-L (diamond) and combo PEGylated DOX-IMT liposome (DOX: circle and IMT:square) at 1:1 molar ratio of DOX:IMT in accelerated condition (54° C.). (NH4)2SO4 was used as the trapping agent in all liposomes above.

In-Vitro Release and Stability Studies of DOX/IMT-L with $(NH_{42}SO_4$ as Trapping Agent Drug release studies for PEGylated DOX/IMT-L, along with the DOX-L and IMT-L, were performed at pH 6.8 (PBS) at accelerated condition by diffusion. As shown in FIG. 7, the sustained releases of DOX and IMT were achieved from the PEGylated DOX/IMT-L. The drug DOX and IMT were released around 40 and 60% at 5-hour time point, respectively. A similar release trend was observed for the single drug-loaded PEGylated DOX-L and IMT-L liposome nanoparticles. In addition, the drug release from the above PEGylated liposome formulations followed similar trends, characterized by a pattern of sustained release with evident lack of initial burst release, this indicated the low free drug content outside DOX/IMT-L liposome sample, which confirmed to the encapsulation efficiency results.

Physical stability of the PEGylated DOX/IMT-L liposome was assessed by recording the changes in mean particle size and particle size distribution (PDI) and encapsulation efficiency (EE %) over a period of 45 days upon storage at 4° C. (long-term storage condition) and 25° C. (accelerated condition). An aliquot of the sample was taken at initial, 1, 4, 7, 15, 30, and 45 days of storage and mean particle size, PDI, and EE % were determined by DLS characterization and HPLC analysis, respectively. The results shown in Table 3 indicated that the DOX/IMT-L liposome nanoparticles with $(NH_4)_2SO_4$ trapping agent are stable for 45 days at storage condition 4° C. and 25° C.

TABLE 3

Physical Stability of PEGylated DOX/IMT Liposome
$(NH_4)_2SO_4$ Trapping Agent at Storage Conditions 4°
C. (long-term storage) and 25° C. (accelerated)

| | Storage at 4° C. | | | Storage at 25° C. | | |
|---|---|---|---|---|---|---|
| (Day) | Mean Particle Size (nm) | PDI | EE % | Mean Particle Size (nm) | PDI | EE % |
| 1 | 98.3 | 0.08 | 99.5 | 98.3 | 0.06 | 99.5 |
| 3 | 98.2 | 0.07 | 99.6 | 98.1 | 0.07 | 99.3 |
| 7 | 101.1 | 0.09 | 99.8 | 98.4 | 0.08 | 99.6 |
| 15 | 99.7 | 0.08 | 99.7 | 98.7 | 0.08 | 99.3 |
| 30 | 99.2 | 0.09 | 99.5 | 98.4 | 0.08 | 99.5 |
| 45 | 99.6 | 0.07 | 99.5 | 98.1 | 0.07 | 99.7 |

Example 4

Effect of Trapping Agent on Encapsulation Efficiency and Drug Release

Figure 8:
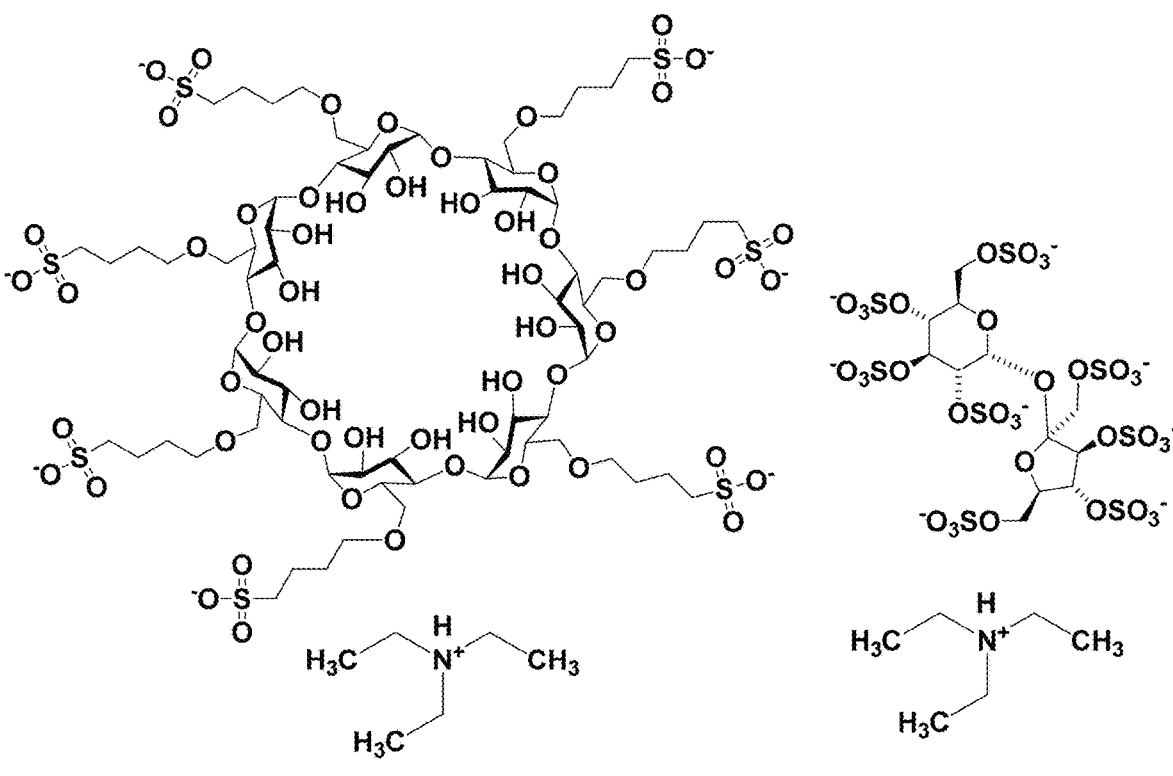
FIG. 8 illustrates the chemical structures of trapping agents TEA-SBE-β-CD (left) and TEA-SOS (right).

As described in the active pH gradient drug loading method of liposome preparation, the trapping agent is critical to the payload, encapsulation efficiency, liposome shape, and drug release properties. For many years, ammonium sulfate has been used as a common well known trapping agent. In this invention, two novel liposome trapping agents, TEA-SOS and TEA-SBE-β-CD, are used and their structures are shown in FIG. 8.

Preparation of TEA-SOS and TEA-SBE-β-CD: Sucrose Octasulfate sodium and SBE-β-cyclodextrin sodium were purchased from Sigma-Aldrich, US. About 10 grams of Sucrose octasulfate sodium or SBE-β-cyclodextrin sodium was dissolved in about 20 mL of deionized water to give a final concentration of about 3 N of the sulfate groups. The solution was passed through a separation column packed with about 150 mL of the cation exchange resin beads. The column was pre-equilibrated with about 3 M HCl, and then washed with deionized water to neutral pH. About 20 mL of the sodium SOS or sodium SBE-β-cyclodextrin solution was applied on the column and eluted with deionized $H_2O$.

Preparation of DOX/IMT-L with TEA-SOS and TEA-SBE-β-CD: The DOX-L, IMT-L, and DOX/IMT-L were prepared by combining emulsification, extrusion, dialysis, and active remote loading as described in Experimental Methods. The comparison of the various trapping agents on encapsulation efficiency and drug release profile of DOX/IMT-L are shown in Table 4. All three trapping agents has excellent encapsulation efficiency (>99.0%) and do not have much influence on the drug encapsulation efficiency and particle size/particle size distribution when DOX/IMT molar ratios at 1:1; 1:5; 1:10 (total drug content is 2 mg/mL). However, the drug release profiles of DOX/IMT-L showed significant influence with all three trapping agents. The trapping agent TEA-SBE-β-CD significantly slowed down drug release comparing to $(NH_4)_2SO_4$ and TEA-SOS. This implies that this slow drug release is a function of the solubility of the drug in the release medium along with the stronger interaction between both DOX and IMT with the TEA-SBE-β-CD.

TABLE 4

Effect of Trapping Agents $(NH_4)_2SO_4$, TEA-SBE-β-CD, and TEA-SOS on Encapsulation Efficiency (EE %) of PEGylated DOX/IMT-L Liposomes.

| Sample Name Molar Ratio | Content of DOX/IMT (mg/mL) | EE % (DOX/IMT) $(NH_4)_2SO_4$ | EE % (DOX/IMT) (TEA-SBE-β-CD) | EE % (DOX/IMT) (TEA-SOS) |
|---|---|---|---|---|
| DOX/IMT-1:10 | 0.17/1.84 | 99.2/99.4 | 96.0/99.2 | 97.2/99.1 |
| DOX/IMT-1:5 | 0.31/1.68 | 99.2/99.4 | 97.5/99.4 | 97.5/99.3 |
| DOX/IMT-1:1 | 0.92/1.03 | 99.3/99.5 | 98.8/99.6 | 98.1/99.5 |

Example 5

Method for DOX/SUN-L Liposome Preparation

The DOX-L, SUN-L, and DOX/SUN-L were prepared with ammonium sulfate, TEA-SOS, and TEA-SBE-β-CD by combining emulsification, extrusion, dialysis, and active remote loading (see Experimental Methods). Preliminary experiments were conducted to identify and optimize major factors in the formulation and production process conditions (such as lipids, composition of liposome, drug to lipid ratio, trapping agent, process conditions, etc.) that affect liposome particle size, particle size distribution, encapsulation efficiency, liposome stability, drug release profile, and other physical properties of liposome. In the dissolution drug release studies with SUN-L and DOX/SUN-L liposomes, it was found sunitinib liposome has fast drug release from SUN-L and DOX/SUN-L with trapping agent ammonium sulfate. To achieve sunitinib sustained release with DOX in liposome, two novel liposome trapping agents, TEA-SOS and TEA-SBE-β-CD, are also used for the DOX/SUN liposome preparation.

Example 6

Physicochemical Characterization of DOX/SUN Liposome

Figure 9:
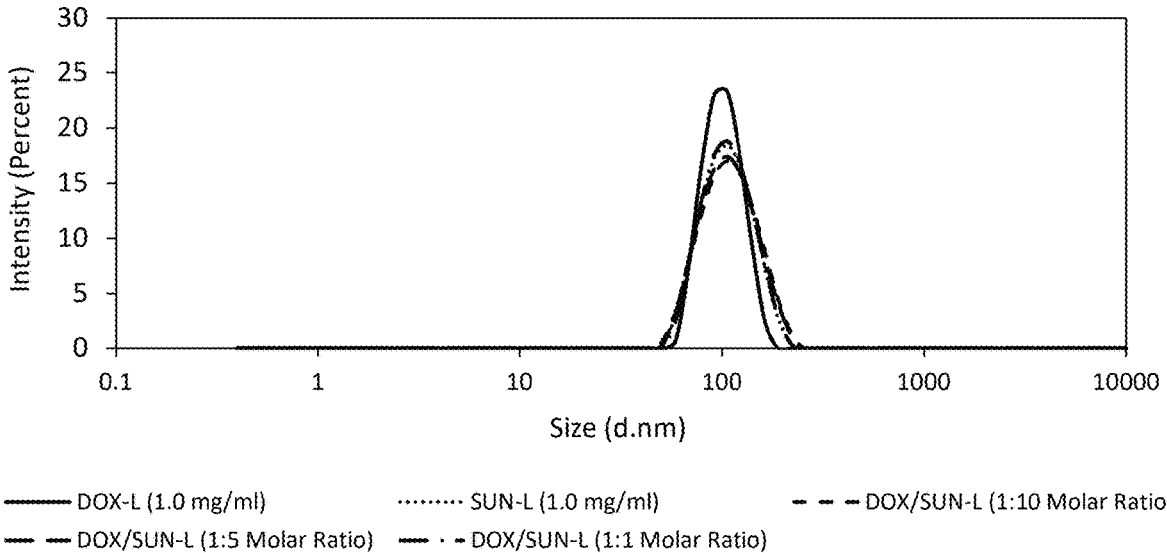
FIG. 9 illustrates the particle size distribution (Intensity %) of DOX-L, SUN-L, and DOX/SUN-L at 1:10, 1:5, and 1:1 molar ratios with TEA-SBE-β-CD as trapping agent.

Physicochemical characterization of DOX-L, SUN-L, DOX/SUN-L were conducted. For example, the liposomes containing doxorubicin and sunitinib were generated using PEGylated and DSPG liposomes containing the trapping agent ammonium sulfate $(NH_4)_2SO_4$ to actively load doxorubicin and/or sunitinib to form DOX-L, SUN-L, and DOX/SUN-L liposomes. The final PEGylated DOX-L, SUN-L, DOX/SUN-L showed the following parameters: mean particle size ~100 nm, PDI <0.100 (see FIG. 9). The comparison of encapsulation efficiency (EE %) with three trapping agents ammonium sulfate, TEA-SBE-β-CD, and TEA-SOS are listed in Table 5. All three trapping agents demonstrated excellent encapsulation efficiency (>95%) with particle sizes around 100 nm.

mixed ammonium sulfate/SBE-β-CD, TEA-SOS, all the SUN-L liposome showed a fairly fast release (>60% release) at 3-hour time point. After 6 hours, sunitinib was completely released (100% release). However, the Sun-L with TEA-SBE-β-CD trapping agent only had ~18% and 30% drug release at 3 and 5-hour time points, respectively. A similar release trend was observed for the coloaded DOX/SUN-L systems with all the trapping agents used for SUN-L. Therefore, the final DOX-L, SUN-L, and DOX/SUN-L were prepared with TEA-SBE-β-CD trapping agent to achieve sustained release for DOX/SUN-L liposomal nanoparticles.

Example 8

Figure 11:
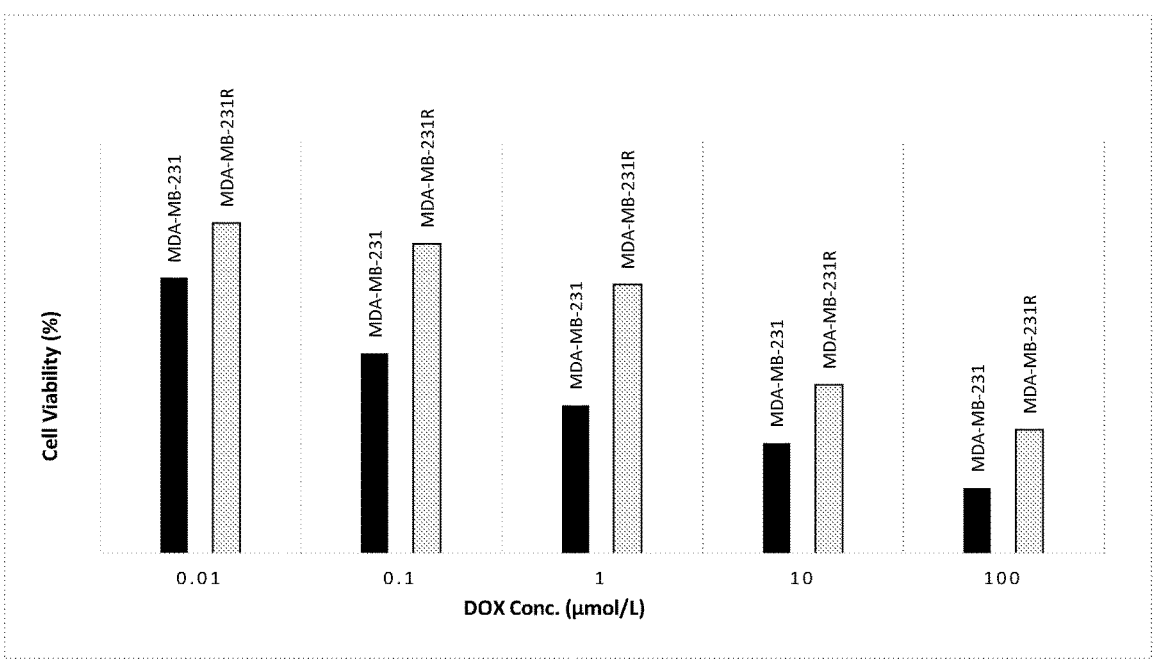
FIG. 11 illustrates the in-vitro cytotoxicity of doxorubicin (DOX) on MDA-MB-231 and MDA-MB-231(R) cells after 48 hours treatment.

Preparation and Characterization of MDA-MB-231 Doxorubicin Resistance Cell Lines Preparation of MDA-MB-231 doxorubicin resistant cell line is described in the Experimental Methods. Characterization of the doxorubicin-resistant variants, MDA-MB-231 (R) cells, was conducted by MTT assay and apoptosis assay analysis. The cell viability for MDA-MB-231(R) after 48-hour DOX treatment was markedly greater at each dose level as compared to MDA-MB-231 (FIG. 11).

Example 9

In-Vitro Doxorubicin and Imatinib Ratio Synergy Studies

For the combined drug, the two or more drugs could exhibit synergistic, additive, or antagonistic interaction. To identify the ratios of doxorubicin and imatinib (DOX/IMT) that are synergistic, various combinations of doxorubicin and imatinib were tested for their cytotoxic effects in-vitro cell line studies. A broad range of drug concentrations to determine the synergy between doxorubicin and imatinib was investigates. Measuring additive, synergistic or antago-

TABLE 5

| Effect of Trapping Agent ($NH_4)_2SO_4$, TEA-SBE-β-CD, and TEA-SOS on Encapsulation Efficiency (EE %) of PEGylated DOX-L, SUN-L, DOX/SUN Liposomes. | | | | |
| --- | --- | --- | --- | --- |
| Sample Name- Molar Ratio | Content of DOX/SUN (mg/mL) | EE % (DOX/SUN) $(NH_4)_2SO_4$ | EE % (DOX/SUN) (TEA-SBE-β-CD) | EE % (DOX/SUN) (TEA-SOS) |
| DOX-L | 1 | 99.7 | 99.5 | 99.1 |
| SUN-L | 1 | 99.5 | 99.3 | 99.3 |
| DOX/SUN-1:10 | 0.18/1.83 | 100/100 | 99.2/99.8 | 99.2/99.4 |
| DOX/SUN-1:5 | 0.33/1.65 | 100/100 | 99.0/99.9 | 99.3/99.1 |
| DOX/SUN-1:1 | 1.01/0.97 | 100/99.6 | 99.3/99.7 | 99.6/99.1 |

Example 7

Drug In-Vitro Release and Stability Study of DOX/SUN-L

Figure 10:
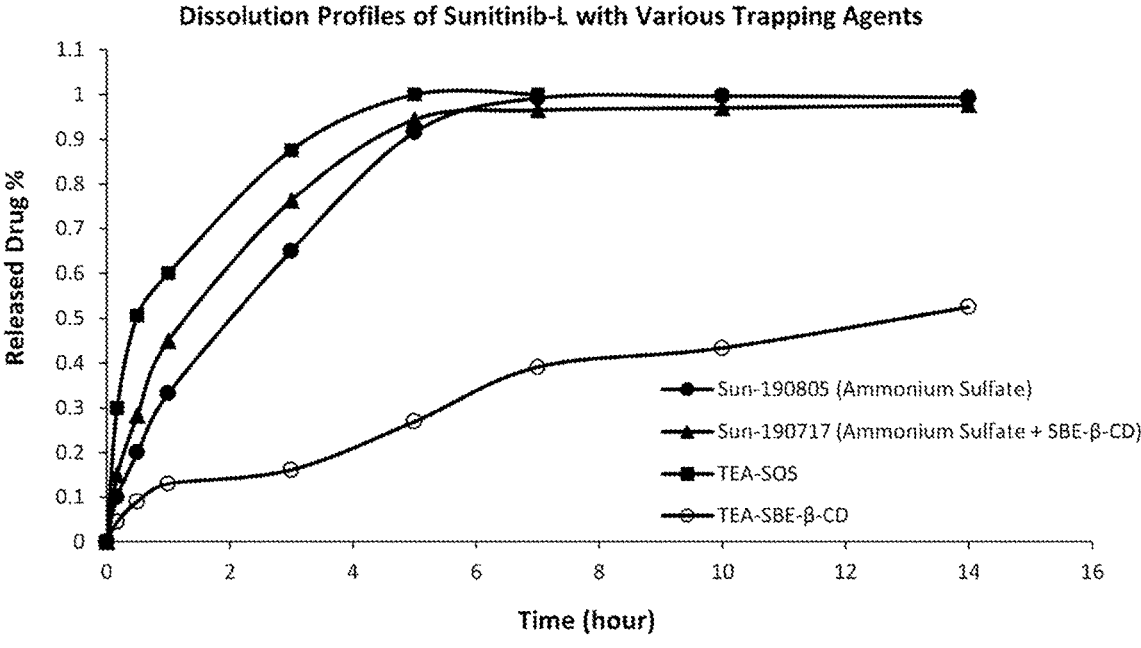
FIG. 10 illustrates the in-vitro drug release profiles of PEGylated SUN-L liposomes with trapping agents $(NH_4)_2SO_4$, TEA-SBE-β-CD, and TEA-SOS at 48° C.
Figure 12:
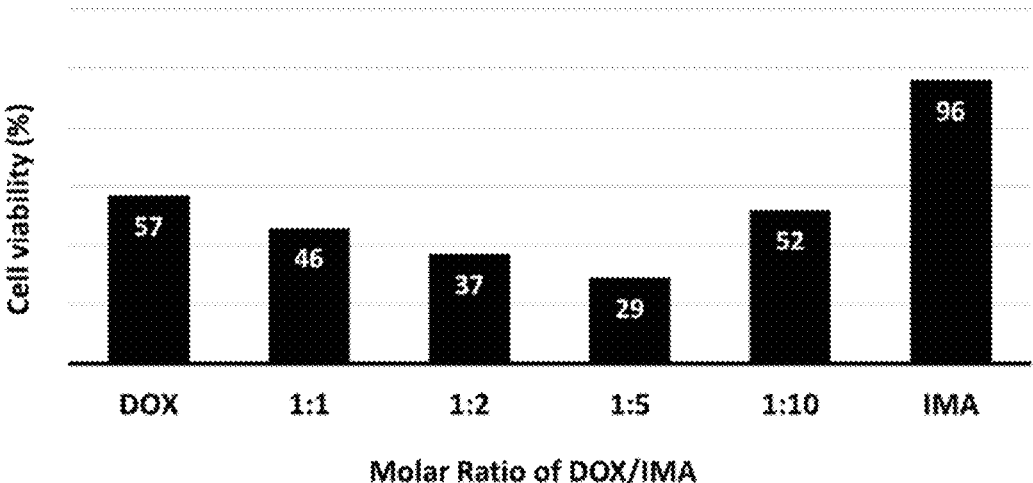
FIG. 12 illustrates the optimization of the molar ratio of DOX and IMT combination with MDA-MB-231(R) cell lines.

Drug release studies of PEGylated DOX-L, SUN-L, DOX/SUN-L with various trapping agents, ammonium sulfate, premixed ammonium sulfate plus TEA-SBE-β-CD, TEA-SOS, TEA-SBE-β-CD, were performed by dialysis at pH 6.8 (PBS) at accelerated condition 48° C. The drug release method is described in Experiment Methods. As shown in FIG. 10, with trapping agents, ammonium sulfate, nistic effects was performed using doxorubicin and imatinib at DOX (only), 1:1, 1:5, 1:10, IMT (only) molar ratios with various cancer cell lines, such as A-673, GIST-882 GIST stromal tumor cells, and MDA-MB-231(R) human breast adenocarcinoma cells. The plot of DOX/IMT molar ratio against the cell viability % demonstrated the synergistic molar ratio for DOX/IMT with MDA-MB-231(R) doxorubicin resistant cell lines is 1:5 (see FIG. 12). The standard tetrazolium-based colorimetric MTT cytotoxicity assay protocol was utilized to determine the readout for the fraction of cells affected.

Example 10

In-Vitro Evaluation of Doxorubicin and Imatinib for Synergy in Cancer Cells

For the combined drug regimes, two or more drugs could exhibit synergistic, additive, or antagonistic interaction depending on the combinational drug ratios. In order to identify the combinational ratios of doxorubicin to imatinib (DOX:IMT) that are synergistic, a broad drug molar ratio range of DOX:IMT were investigated with the related cell lines. Determination on the synergistic, additive, or antagonistic effects between doxorubicin and imatinib were performed using 30:1 to 1:30, preferred 10:1, 5:1, 1:1, 1:5 and 1:10 molar ratios of DOX:IMT with various cancer cell lines, such as SK-MEL-28 (melanoma cancer cells that show intrinsic resistance to doxorubicin), BT-549 (triple-negative breast cancer cells that show intrinsic resistance to doxorubicin), MCF-7 (R) (breast cancer cells that show acquired resistance to doxorubicin), A-673 (Ewing sarcoma cell line with a type 1 EWS-FLI-1 fusion), A-549 (non-small cell lung cancer, NSCLC), GIST-T1(GIST with KIT mutation: heterozygous exon 11, V560-Y579 deletion), and HT-29 (colorectal adenocarcinoma), etc.

Figure 13:
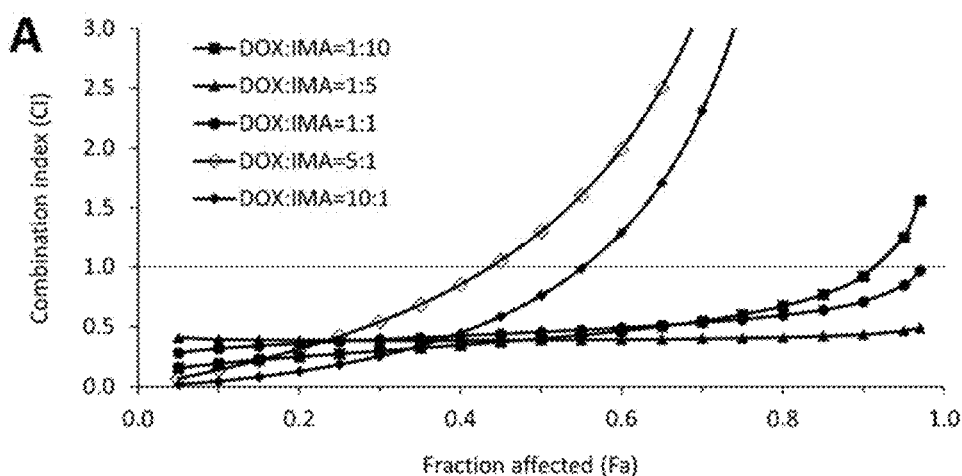
FIG. 13 illustrates the in-vitro screening of doxorubicin (DOX) and imatinib (IMT) for synergy in SK-MEL-28 melanoma cells. A: Combination index (CI) is plotted as a function of cell growth inhibition (i.e., fraction affected, Fa) on SK-MEL-28 melanoma cells in response to the combination treatment by doxorubicin (DOX) and imatinib (IMT) at various mole ratios: 1:10 (solid square), 1:5 (solid triangle), 1:1 (solid circle), 5:1 (blank diamond) and 10:1 (solid diamond). CI values of <0.9, 0.9-1.1, and >1.1 indicate synergy, additivity, and antagonism, respectively. B: In-vitro evaluation of CI from SK-MEL-28 melanoma cells plotted at $ED_{75}$ (black column, Fa=0.75) and $ED_{90}$ (blank columns, Fa=0.90) as a function of different doxorubicin to imatinib molar drug ratios, i.e., 1:10, 1:5, 1:1, 5:1 and 10:1.
Figure 13:
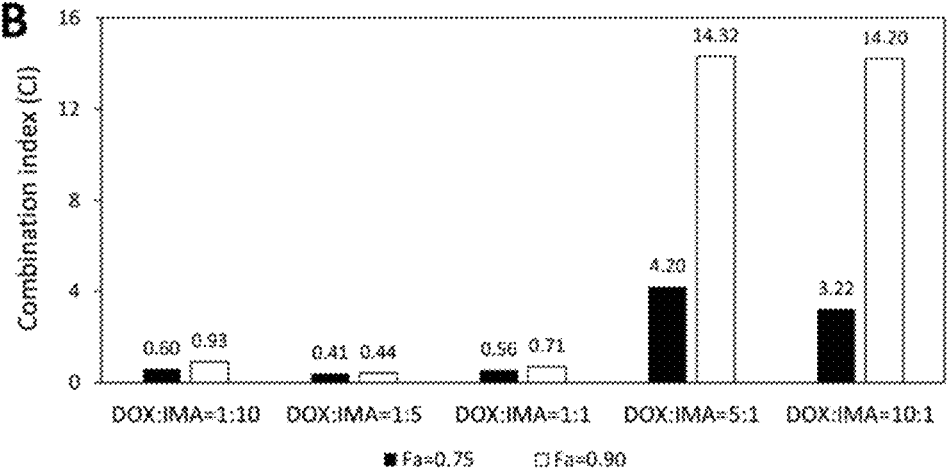

FIG. 13A shows the CI value as a function of cell growth inhibition, i.e., the fraction affected (Fa) on SK-MEL-28 melanoma cell at various DOX to IMT molar ratios. At DOX:IMT ratios of 1:10, 1:5 and 1:1, synergy was observed since CI is much less than 0.9 in a wide range 0.05-0.9 of Fa. These demonstrated that 1:1, 1:5, and 1:10 DOX:IMT ratios are synergistic at concentrations that cause significant tumor cell death. In contrast, antagonistic effect was observed (i.e., CI>1.1) when the Fa is higher than 0.6 with DOX:IMT molar ratios at both 10:1 and 5:1. The dependence of CI on DOX:IMT ratio is also presented in FIG. 13B where CI values at drug concentrations sufficient to cause 75% ($ED_{75}$) and 90% ($ED_{90}$) tumor cell growth inhibition are compared at the different DOX:IMT molar ratios in SK-MEL-28 cells. The strongest synergy effect was observed when the DOX:IMT ratio is at 1:5. Based on above results, a DOX:IMT across a wide range of Fa (between 0.2 to 0.9). However, at the ratio of 1:1, antagonism was observed at all Fa values for the combination of DOX:IMT. For other DOX:IMT ratios, i.e., 1:10, 5:1 and 10:1, no significant synergistic effect was detected, and the effect of the combinations was additive. Based on these results, a DOX:IMT mole ratio of 1:5 was selected as fixed drug ratio to formulate liposome product for the treatment of BT-549 breast cancer.

Figure 15:
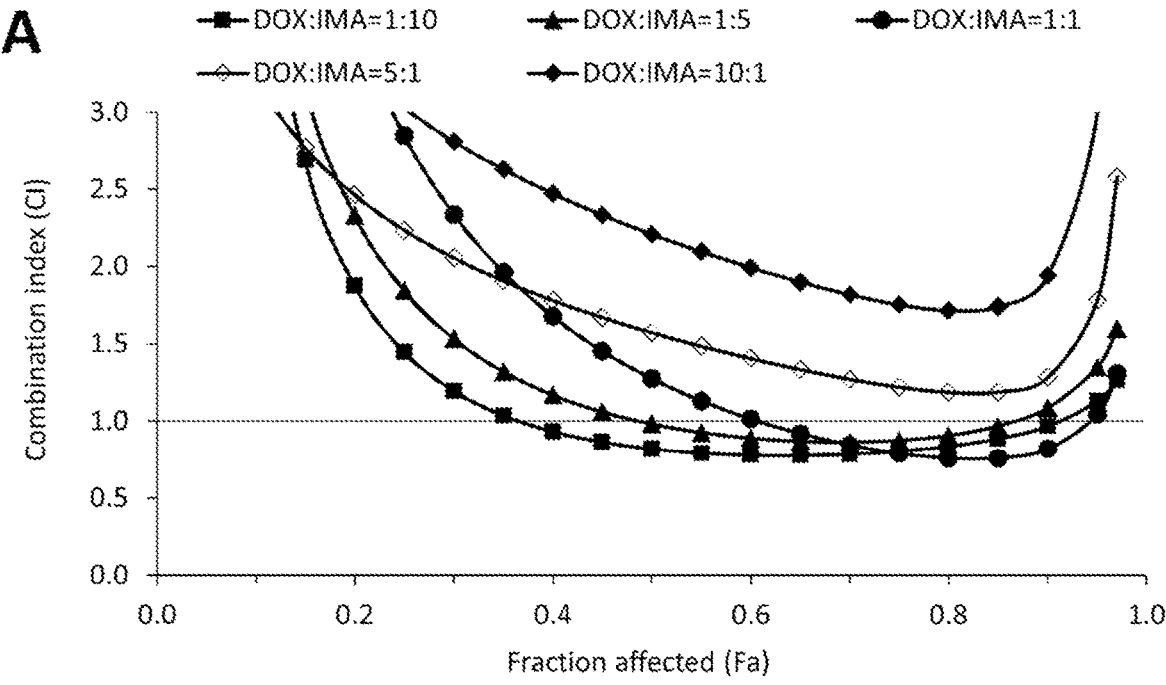
FIG. 15 illustrates the in-vitro screening of doxorubicin (DOX) and imatinib (IMT) for synergy in resistant MCF-7, i.e., MCF-7(R) breast cancer cells. A: Combination index (CI) is plotted as a function of cell growth inhibition (i.e., fraction affected, Fa) on MCF-7(R) cells in response to the combination treatment by doxorubicin and imatinib at various mole ratios: 1:10 (solid square), 1:5 (solid triangle), 1:1 (solid circle), 5:1 (blank diamond) and 10:1 (solid diamond). Resistance of MCF-7 breast cancer cells was generated by continuously culturing the cell in the presence of low concentration of doxorubicin. CI values of <0.9, 0.9-1.1, and >1.1 indicate synergy, additivity, and antagonism, respectively. B: In-vitro evaluation of CI from MCF-7(R) doxorubicin-resistant breast cancer cells plotted at $ED_{75}$ (black column, Fa=0.75) and $ED_{90}$ (blank columns, Fa=0.90) as a function of different doxorubicin to imatinib molar drug ratios, i.e., 1:10, 1:5, 1:1, 5:1 and 10:1.
Figure 15:
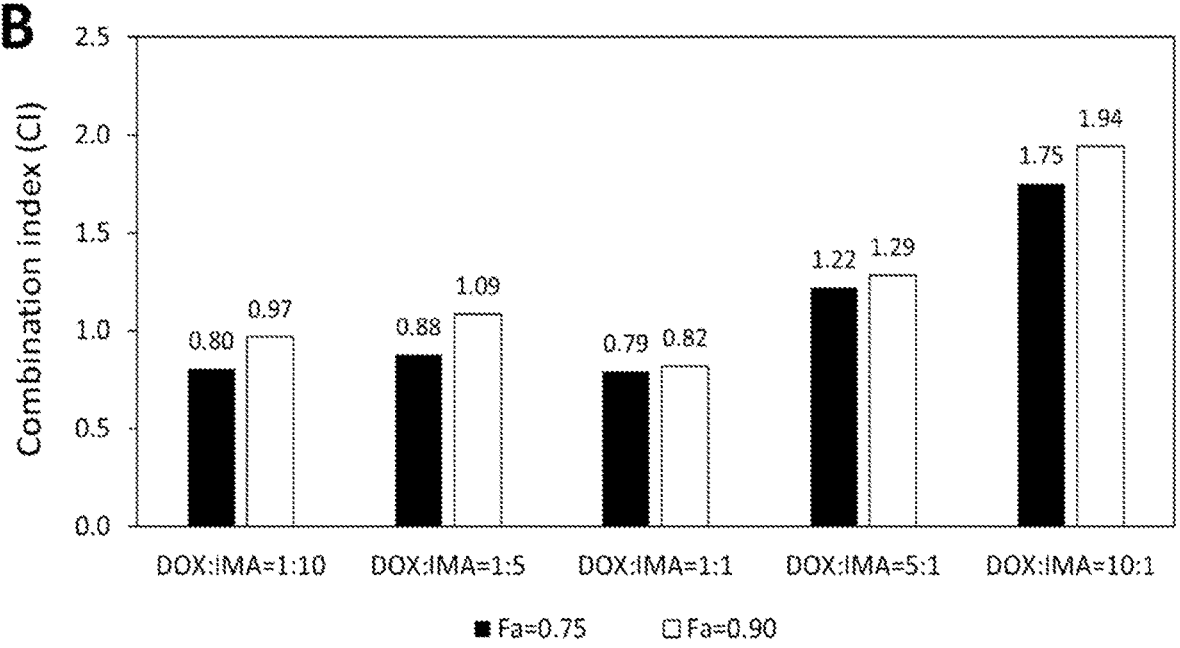

Drug combination effect as reflected by CI values were also evaluated on doxorubicin resistant MCF-7 breast cancer cells, i.e., MCR-7(R) in response to DOX/IMT treatment at various drug molar ratios. The resistant MCF-7 cells were generated by repeatedly culturing the cell in the presence of low concentration of DOX. Cells that proliferated well in the presence of DOX after several passages qualified as DOX resistant MCF-7. As shown in FIGS. 15A and 15B, additive effect was observed at the DOX:IMT ratio of both 1:5 and 5:1. In contrast, a mild synergy was observed at the DOX:IMT ratio of 1:1 at both $ED_{75}$ and $ED_{90}$. Therefore, a DOX:IMT mole ratio of 1:1 was selected as fixed drug ratio to formulate liposome product for the treatment of doxorubicin resistant MCF-7 breast cancer.

Figure 16:
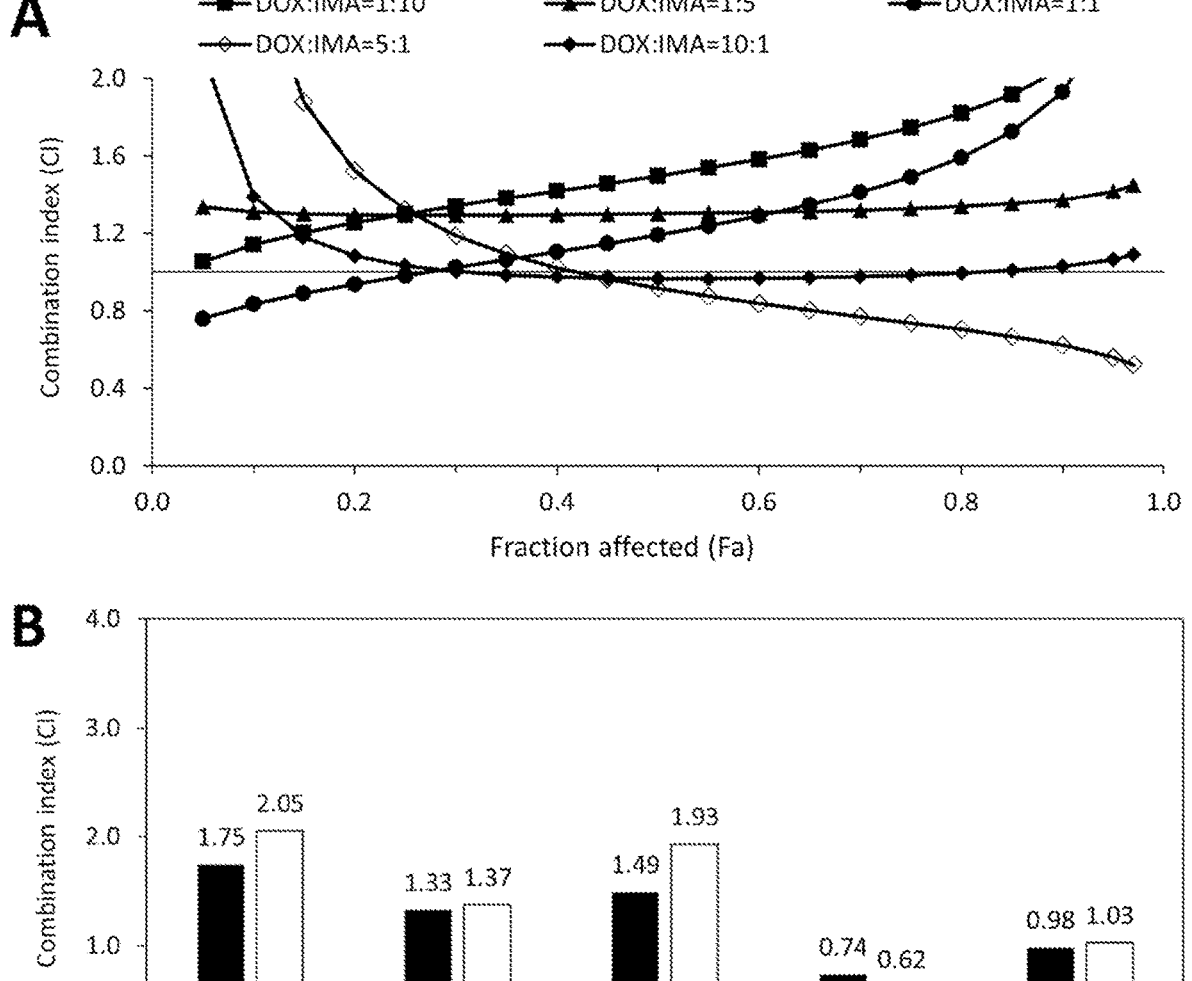
FIG. 16 illustrates the in vitro screening of doxorubicin (DOX) and imatinib (IMT) for synergy in GIST-T1 gastrointestinal stromal tumor cell. A: Combination index (CI) is plotted as a function of cell growth inhibition (i.e., fraction affected, Fa) on GIST-T1 cells in response to the combination treatment by doxorubicin and imatinib at various mole ratios: 1:10 (solid square), 1:5 (solid triangle), 1:1 (solid circle), 5:1 (blank diamond) and 10:1 (solid diamond). CI values of <0.9, 0.9-1.1, and >1.1 indicate synergy, additivity, and antagonism, respectively. B: In-vitro evaluation of CI from GIST-T1 cancer cells plotted at $ED_{75}$ (black column, Fa=0.75) and $ED_{90}$ (blank columns, Fa=0.90) as a function of different doxorubicin to imatinib molar drug ratios, i.e., 1:10, 1:5, 1:1, 5:1 and 10:1.

In addition to the three cell lines mentioned above, the drug combination effect as reflected by CI values on other cancer cell lines were also evaluated. Those cells include A-673 sarcoma, GIST-T1 gastrointestinal stromal, A-549 NSCLC and HT-29 colorectal. CI values at $ED_{75}$ and $ED_{90}$ for all cell lines studied at various DOX/IMT ratios are summarized in Table 6 below. These results indicate the combination effect of DOX/IMT are either additive or antagonistic on A-673, GIST, A-549, and HT-29 cell lines in a broad range of drug ratios and no significant synergistic effect were observed among those cell lines in response to DOX/IMT treatment. As mentioned above, synergistic effect was obtained at 1:5 DOX/IMT molar ratio on both SK-MEL-28 melanoma and BT-549 breast cancer cells. Synergy was also found at 1:1 ratio of DOX/IMT on both MCF-7(R) breast cancer cells and SK-MEL-28 melanoma cells. In addition, a DOX/IMT molar ratio of 5:1 generated synergistic effect on GIST-T1 cancer cells as well (FIGS. 16A and 16B). Drug ratios with synergistic effect are bolded in Table 6.

TABLE 6

CI Values at $ED_{75}$ and $ED_{90}$ of Different DOX:IMT
Molar Ratios in Various Cancer Cell Lines

| | Molar Ratio of DOX:IMT | | | | | | | | | |
| | 10:1 | | 5:1 | | 1:1 | | 1:5 | | 1:10 | |
| Cell Line | $ED_{75}$ | $ED_{90}$ | $ED_{75}$ | $ED_{90}$ | $ED_{75}$ | $ED_{90}$ | $ED_{75}$ | $ED_{90}$ | $ED_{75}$ | $ED_{90}$ |
| --- | --- | --- | --- | --- | --- | --- | --- | --- | --- | --- |
| SK-MEL-28 | 3.22 | 14 | 4.20 | 14 | 0.56 | 0.71 | 0.41 | 0.44 | 0.60 | 0.93 |
| BT-549 | 0.96 | 1.27 | 0.97 | 1.07 | 1.96 | 2.85 | 0.45 | 0.54 | 0.72 | 1.01 |
| MCF-7 (R) | 1.75 | 1.94 | 1.22 | 1.29 | 0.79 | 0.82 | 0.88 | 1.09 | 0.80 | 0.97 |
| A-673 | 1.15 | 0.81 | 1.33 | 0.99 | 1.10 | 3.04 | 0.95 | 1.52 | 1.68 | 2.69 |
| GIST-T1 | 0.98 | 1.03 | 0.74 | 0.62 | 1.49 | 1.94 | 1.33 | 1.37 | 1.75 | 2.05 |
| A-549 | 25 | 758 | 3.78 | 44 | 1.49 | 1.93 | 1.08 | 1.68 | 1.34 | 4.93 |
| HT-29 | n/a | n/a | 40 | 395 | 1.81 | 5.33 | 1.08 | 1.51 | 1.70 | 1.95 | molar ratio of 1:5 was selected as fixed drug ratio to formulate liposome drug product for the treatment of SK-MEL-28 melanoma cancer.

Figure 14:
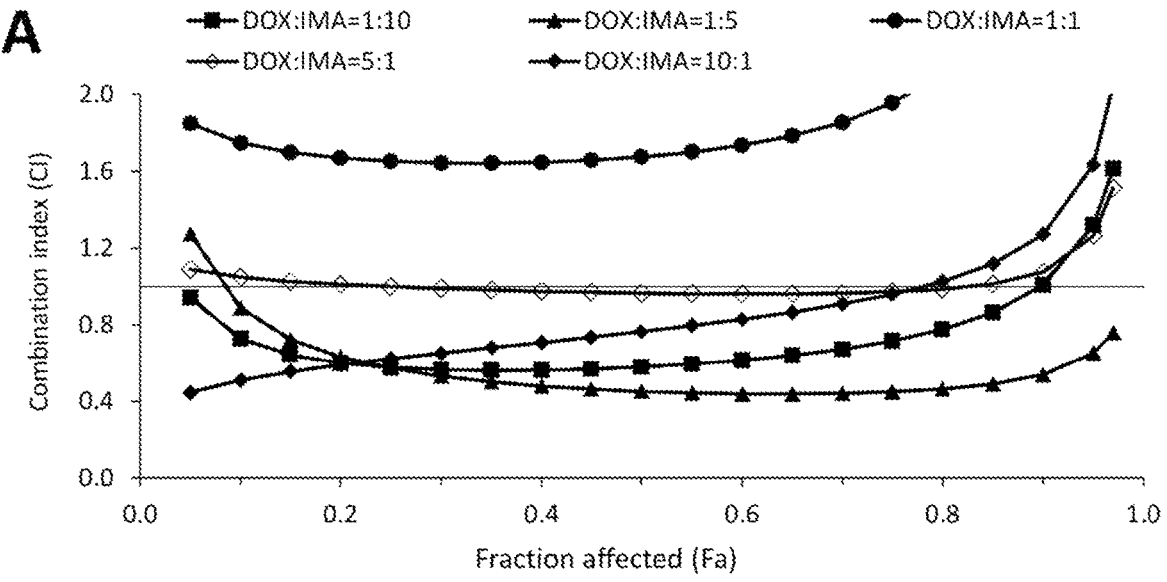
FIG. 14 illustrates the in-vitro screening of doxorubicin (DOX) and imatinib (IMT) for synergy in BT-549 triple-negative breast cancer cells. A: Combination index (CI) is plotted as a function of cell growth inhibition (i.e., fraction affected, Fa) on of BT-549 cells in response to the combination treatment by doxorubicin and imatinib at various mole ratios: 1:10 (solid square), 1:5 (solid triangle), 1:1 (solid circle), 5:1 (blank diamond) and 10:1 (solid diamond). CI values of <0.9, 0.9-1.1, and >1.1 indicate synergy, additivity, and antagonism, respectively. B: In-vitro evaluation of CI from BT-549 breast cancer cells plotted at $ED_{75}$ (black column, Fa=0.75) and $ED_{90}$ (blank columns, Fa=0.90) as a function of different doxorubicin to imatinib molar drug ratios, i.e., 1:10, 1:5, 1:1, 5:1 and 10:1.
Figure 14:
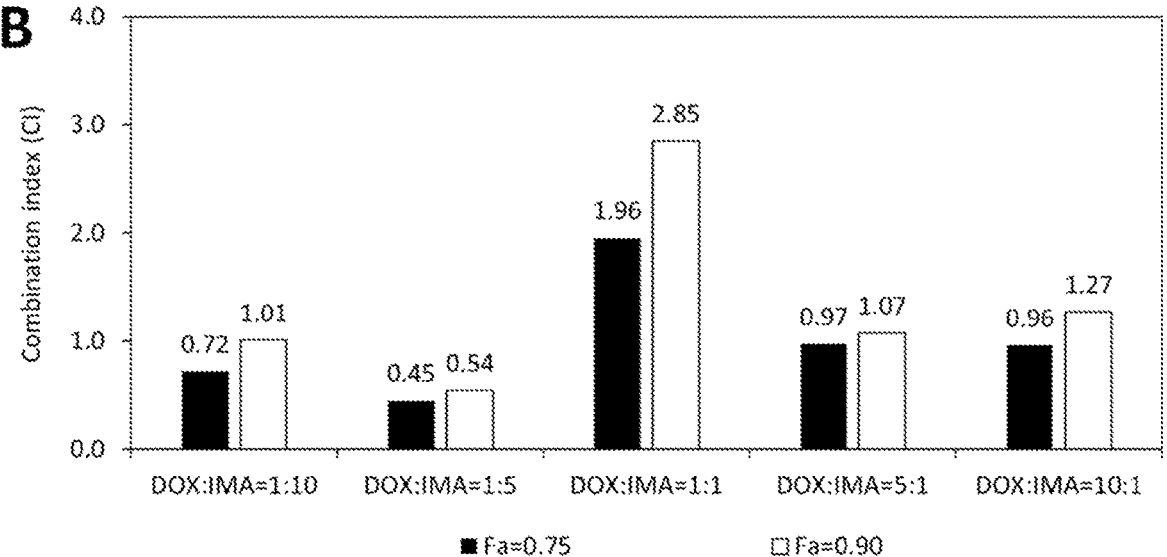

In a similar approach, the effect of DOX:IMT ratios on cell growth inhibition in BT-549 triple negative breast cancer cells were also investigated, and the results were presented in FIGS. 14A and 14B. The data reflects that the combination of DOX:IMT at the ratio of 1:5 is synergistic

Example 11

In-Vitro Evaluation of Doxorubicin and Sunitinib for Synergy in Cancer Cells To identify ratios of doxorubicin to sunitinib (DOX:SUN) that are synergistic, various drug molar ratios of DOX:SUN were investigated with similar procedures described in Example 10. Determination of the additive, synergistic, or antagonistic effects of the drug combinations were performed using 30:1 to 1:30, preferred 10:1, 5:1, 1:1, 1:5, 1:10 molar ratios of DOX:SUN on the following cell lines: SK-MEL-28 (melanoma cancer cells that show intrinsic resistance to doxorubicin) and BT-549 (triple-negative breast cancer cells that show intrinsic resistance to doxorubicin). The standard tetrazolium-based colorimetric MTT cytotoxicity assay method was also utilized to determine the readout for the fraction of cells affected in response to drug treatment.

Figure 17:
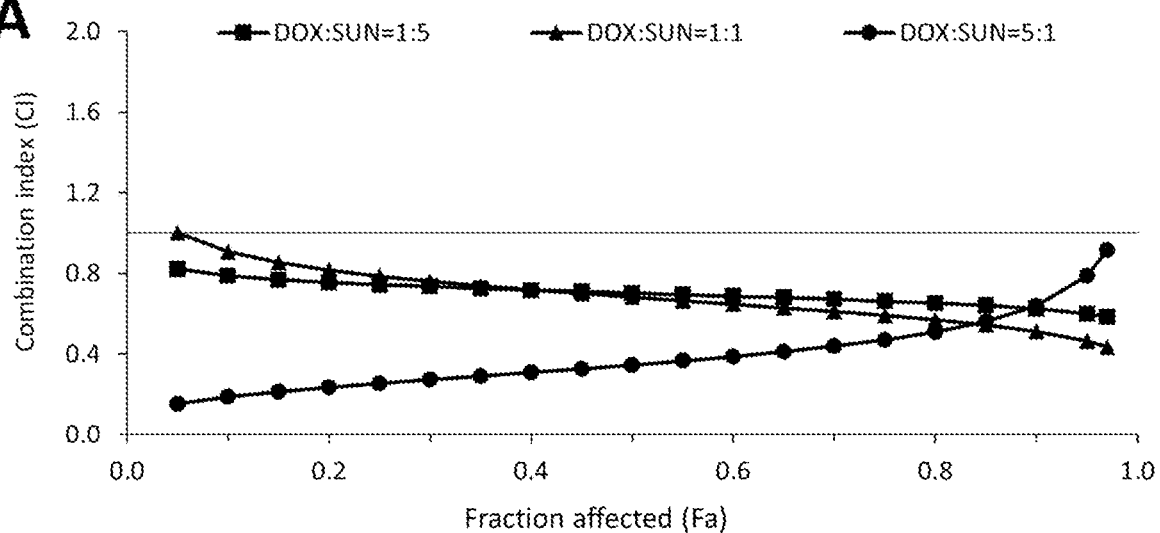
Figure 17:
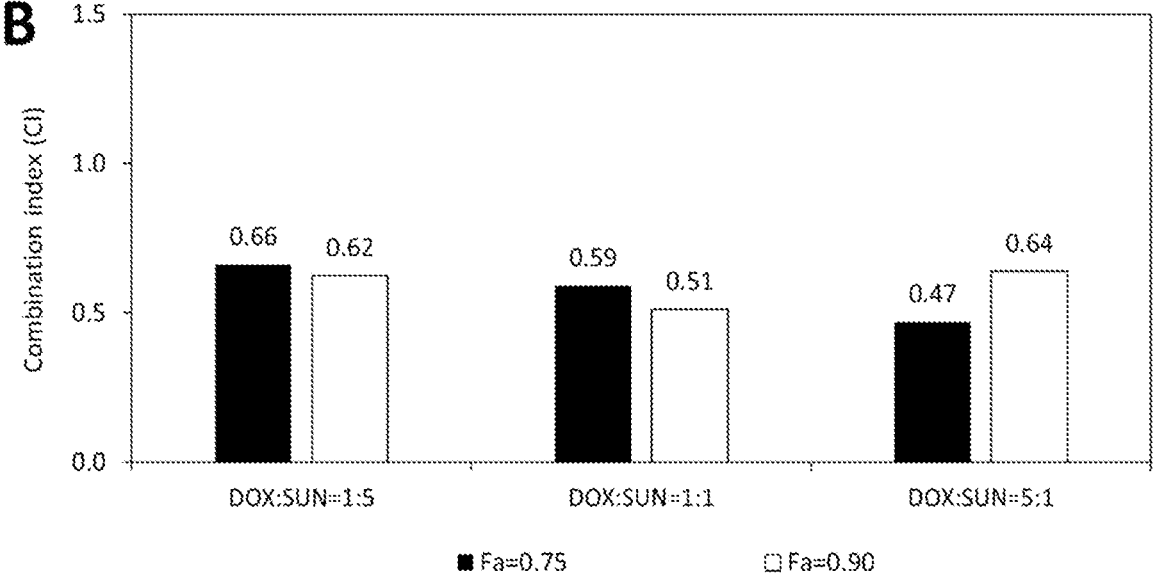

As shown in FIG. 17A, synergistic effect of the combination of DOX and SUN on SK-MEL-28 melanoma cells was found with three tested drug molar ratios 5:1, 1:1, and 1:5 across a broad range of drug concentrations (i.e. $0.10 < Fa < 0.95$). Specifically, strong drug synergy was observed at drug concentrations giving rise to 75% and 90% sulation efficiency (EE %) was investigated on liposomal DOX/IMT combinations at the drug molar ratio of 1:5 using PEGylated liposome (Table 7). Drug encapsulation efficiency was evaluated after liposome elution through a Sephadex G-50 spin column. Then, drug loading efficiency was determined using HPLC-UV analysis. Three different trapping agents were employed for drug remote loading, namely ammonium sulfate, TEA-SBE-β-CD and TEA-SOS. One general trend was observed independently from the type of trapping agent used: when the total lipid to total drug molar ratio is $\geq 3.2:1$, a remarkably high payload EE % ($\geq 95\%$) can be obtained. However, when the total lipid to total drug molar ratio was decreased to $\leq 1.6:1$, a significant reduction on EE % was observed (EE % <80%). Based on above results, the total lipid to total drug molar ratio at 6.4:1 was selected for further liposome composition study.

TABLE 7

Effect of Total Lipid to Total Drug Ratio on Drug Encapsulation Efficiency (%)
DOX:IMT molar drug ratio 1:5 with PEGylated DOX/IMT-L

| Total lipid:Total drug (mole/mole) | EE % (DOX/IMT) $(NH_4)_2SO_4$ | EE % (DOX/IMT) (TEA-SBE-CD) | EE % (DOX/IMT) (TEA-SOS) |
|---|---|---|---|
| 6.4:1 | 99.1/99.5 | 99.5/99.3 | 99.5/99.6 |
| 3.2:1 | 99.2/99.0 | 99.1/96.8 | 99.4/95.0 |
| 1.6:1 | 69.7/63.4 | 68.5/56.1 | 71.9/76.1 |

TEA-SBE-CD: triethylammonium sulfobutyl ether beta-cyclodextrin;
TEA-SOS: triethylammonium sucrose octasulfate tumor growth inhibition ($ED_{75}$ and $ED_{90}$, corresponding to Fa=0.75 and 0.90, respectively) at all three drug ratios (CI<0.70, FIG. 17B). The effect of drug combination on cell growth inhibition was also analyzed on BT-549 breast cancer cells (FIGS. 18A and 18B). In general, drug ratio dependent CI profiles was observed at low and middle drug concentrations (i.e., Fa<0.7). In contrast, at high Fa range (i.e., Fa>0.70), synergic effect of all three drug ratios was obtained. Specifically, a pronounced synergy was seen at DOX:SUN ratio equals 1:1 at both $ED_{75}$ and $ED_{90}$ (CI<0.4, FIG. 18B). Based on the above results, a DOX:SUN ratio of 1:1 was selected for the formulation of a liposome combination drug product for the treatment of both SK-MEL-28 melanoma and BT-549 breast cancer.

Example 12

Effect of Lipid to Drug Ratio on Drug Encapsulation Efficiency

The examples of the liposome preparations with active loading process are described in the Experimental Methods section. The effect of the lipid to drug ratio on drug encap- Example 13

Physicochemical Characterization of Dual Drug Loaded Liposome

Mean particle size of the liposome was analyzed by the dynamic light scattering method. Drug encapsulation efficiency was evaluated using the similar procedure described in Experimental Methods. In-vitro dissolution study was performed at pH 6.8 by dialysis.

Characterization on mean particle size (diameter) and encapsulation efficiency (EE %) of DOX and IMT in PEGylated liposomal DOX/IMT-L using various types of trapping agents was summarized in Table 8. As demonstrated in Table 8, PEGylated DOX-L, IMT-L, DOX/IMT-L liposomes have the mean particle size 90-105 nm and PDI <0.100 with excellent encapsulation efficiency % (~99%) with ammonium sulfate, TEA-SOS, and TEA-SBE-β-CD trapping agents. However, the encapsulation efficiency % of IMT dropped to about 90% and 72% with Tris-SBE-β-CD and copper gluconate trapping agents, respectively. In all above PEGylated liposomes, the compositions were fixed at a total lipid to total drug molar ratio of 6.4:1.

TABLE 8

Comparison of Mean Particle Size (diameter) and Encapsulation Efficiency (EE %) of
Doxorubicin and/or Imatinib in PEGylated DOX/IMT-L with Various Trapping Agents

| Samples (molar ratio) | $(NH_4)_2SO_4$ | | TEA-SOS | | TEA-SBE-CD | | Tris-SBE-CD | | CuGlu/TEOA | |
| | Mean Particle Size (nm) | EE % DOX/IMT | Mean Particle Size (nm) | EE % DOX/IMT | Mean Particle Size (nm) | EE % DOX/IMT | Mean Particle Size (nm) | EE % DOX/IMT | Mean Particle Size (nm) | EE % DOX/IMT |
|---|---|---|---|---|---|---|---|---|---|---|
| DOX-L | 94 | 99.1 | 97 | 99.5 | 102 | 99.1 | — | — | — | — |
| IMT-L | 98 | 99.5 | 103 | 99.6 | 103 | 99.3 | — | — | — | — |

TABLE 8-continued

Comparison of Mean Particle Size (diameter) and Encapsulation Efficiency (EE %) of
Doxorubicin and/or Imatinib in PEGylated DOX/IMT-L with Various Trapping Agents

| | $(NH_4)_2SO_4$ | | TEA-SOS | | TEA-SBE-CD | | Tris-SBE-CD | | CuGlu/TEOA | |
|---|---|---|---|---|---|---|---|---|---|---|
| Samples (molar ratio) | Mean Particle Size (nm) | EE % DOX/IMT | Mean Particle Size (nm) | EE % DOX/IMT | Mean Particle Size (nm) | EE % DOX/IMT | Mean Particle Size (nm) | EE % DOX/IMT | Mean Particle Size (nm) | EE % DOX/IMT |
| DOX/IMT-L (1:10) | 97 | 99.2/99.4 | 103 | 98.7/99.7 | 94 | 99.4/99.1 | — | — | — | — |
| DOX/IMT-L (1:5) | 97 | 99.3/99.5 | 102 | 99.1/99.7 | 95 | 99.6/99.2 | 94 | 97.0/90.0 | 91 | 100/72.0 |
| DOX/IMT-L (1:1) | 97 | 99.3/99.5 | 100 | 99.5/99.8 | 100 | 98.8/99.6 | — | — | — | — |

AS: ammonium sulfate;
TEA-SOS: triethylammonium sucrose octasulfate;
TEA-SBE-CD: triethylammonium sulfobutyl ether beta-cyclodextrin;
Tris-SBE-CD: tris(hydroxymethyl)aminomethane salt of SBE-CD;
CuGlu/TEOA: copper gluconate/triethanolamine For PEGylated DOX/SUN-L liposome, the characterization on mean particle size (diameter) and encapsulation efficiency (EE %) of DOX and SUN using various types of trapping agents was also summarized in Table 9. As shown in Table 9, PEGylated DOX-L, SUN-L, DOX/SUN-L liposomes have the mean particle size ~100 nm and PDI<0.100 with excellent encapsulation efficiency % (~99%) with ammonium sulfate, TEA-SOS, and TEA-SBE-β-CD trapping agents. In all above PEGylated liposomes, the compositions were fixed at a total lipid to total drug molar ratio of 6.4:1.

tioned trapping agents. Therefore, TEA-SBE-β-CD was selected as the trapping agent to further encapsulate the dual drugs within the liposome.

The morphology of the liposome was visualized by cryogenic transmission electron microscopy (Cryo-TEM). FIG. 19 revealed the TEM image of the dual-loaded PEGylated liposomal nanoparticles (DOX:IMT molar ratio at 1:5, TEA-SBE-β-CD) exhibited a spherical shape with unilamellar structure with a dense core (precipitates of DOX and IMT) and ~100 nm mean particle size. The dark interior indicates that the internal compartment is heavily electron dense,

TABLE 9

Comparison of Mean Particle Size (diameter) and Encapsulation Efficiency (EE %) of
Doxorubicin and/or Sunitinib in PEGylated DOX/SUN-L with Various Trapping Agents

| | $(NH_4)_2SO_4$ | | TEA-SOS | | TEA-SBE-CD | |
|---|---|---|---|---|---|---|
| Sample Name (Molar Ratio) | Mean Particle Size (nm) | EE % (DOX/SUN) | Mean Particle Size (nm) | EE % (DOX/SUN) | Mean Particle Size (nm) | EE % (DOX/SUN) |
| DOX-L | 94 | 99.1 | 97 | 99.5 | 102 | 99.1 |
| SUN-L | 98 | 99.5 | 101 | 99.8 | 104 | 99.8 |
| DOX/SUN-L (1:10) | 97 | 99.8/99.9 | 100 | 99.6/99.7 | 102 | 99.2/99.8 |
| DOX/SUN-L (1:5) | 96 | 99.8/99.6 | 100 | 99.9/99.5 | 102 | 99.0/99.9 |
| DOX/SUN-L (1:1) | 96 | 99.9/99.7 | 99 | 99.8/99.6 | 103 | 99.3/99.7 |

AS: ammonium sulfate;
TEA-SOS: triethylammonium sucrose octasulfate;
TEA-SBE-CD: triethylammonium sulfobutyl ether beta-cyclodextrin For the in-vitro drug release, it was found that the drug release rate of DOX/IMT or DOX/SUN in the PEGylated DOX/IMT-L and DOX/SUN-L show a dependence on the type of trapping agent and its concentration. At the appropriate concentrations of the trapping agents, the drug release rate is in the order of $(NH_4)_2SO_4$>copper gluconate>TEA-SOS>Tris-SBE-β-CD>TEA-SBE-β-CD. In addition, with ammonium sulfate, the drug release rate of DOX and IMT in PEGylated DOX/IMT-L are much slow than in DOX/IMT-DSPG-L.

Based on above results, it was demonstrated that drug loaded with TEA-SBE-β-CD as the trapping agent in the liposome exhibited excellent encapsulation efficiency and a superior payload retention comparing to other above menwhich reflects an aggregation state of the API interacting with the trapping agent. Those results confirmed that both drugs were well co-encapsulated in the aqueous core compartment of the liposome in an aggregation/precipitation state.

Example 14

General Preparation of Liposome Via
Passive/Active Dual Drug Loading

For the combination dual agents loading, the two drugs could be encapsulated into the liposome by coupled active and passive loading methods. For example, both drugs are loaded via a passive loading approach or one is passive loading while for another is active loading. As described in Experimental methods, PEGylated lipid compositions were also employed here with DSPC (>10 mol % of total lipid), cholesterol (0-50 mol % of total lipid) and mPEG-2000-DSPE (PEGylated liposome) at various lipid ratios. Briefly, an example of general coupled active and passive loading liposomal preparation is described below:

General Preparation of Liposome Via Coupled Active and Passive Dual Drug Loading 1) Preparation of multilamellar vesicles containing one drug: all lipids were dissolved in organic solvent. One drug (e.g. gemcitabine hydrochloride, GEM) and a select trapping agent (e.g. TEA-SBE-β-CD aqueous solution) were dissolved in water with appropriate concentrations, and then warmed to 60-70° C. The lipid solution was then dispersed into the above aqueous solution under vigorous stirring to form the multilamellar vesicles for about 5 hours. 2) Liposome size reduction: extrusion was conducted by multiple passes through polycarbonate membranes with a pore size of 50-100 nm. The target liposome size range is 50-200 nm, preferably between 80-110 nm. 3) Diafiltration: to remove the external trapping agent and the external first loaded drug, transfer the passive loaded liposomes into the active loading solution at a pH of 6-7.5. 4) Active loading of the second drug: the second drug stock solution (e.g., sunitinib malate) was prepared by dissolving the agent in aqueous solution to achieve the desired concentration and synergetic ratio to first therapeutic agent. Add the second therapeutic agent stock solution into the liposome dispersion prepared in Step 3 to achieve the lipid/drug input molar ratio >1.0. The mixture was incubated 60-70° C. for about 1-3 hours. The liposome drug product was cooled to room temperature and stored at 2-8° C.

The physicochemical characterization method on the PEGylated GEM/SUN-L liposome was performed as described in the Experimental Methods. As an example, with above co-loaded PEGylated GEM/SUN-L liposome, Table 10 showed the mean particle size (diameter), encapsulation efficiency (%), and total GEM/SUN to total lipid molar ratio of GEM/SUN-L dual drug loaded liposome with the TEA-β-SBE-SD trapping agent. The GEM/SUN-L liposome leakage studies demonstrated both GEM and SUN in GEM/SUN-L are stable for at least four weeks under refrigerator condition. In addition, the cell line (preferred NSCLC cell lines) studies demonstrated that synergistic combination of gemcitabine and sunitinib is at 5:1, 1:1, and 1:5 molar ratios.

TABLE 10

Characterization on Gemcitabine (GEM) and Sunitinib (SUN) Co-encapsulated Liposomes

| Sample Name Molar Ratio | Molar Ratio GEM/SUN to Total Lipids | Particle Size (nm)/PDI | Encapsulation Efficiency (%) |
|---|---|---|---|
| GEM/SUN-L 1:1 | 0.17 (GEM) 0.12 (SUN) | 98/0.074 | 99.1 (GEM) 98.9 (SUN) |

Example 15

DOX/IMT Liposome In-Vitro Inhibition of Cell Growth

To compare the liposome in-vitro inhibition of cell growth, SK-MEL-28 melanoma cells were treated with PEGylated DOX-L, IMT-L, DOX/IMT-L with DOX:IMT at 1:5 (synergic) and 5:1 (antagonistic) molar ratios. A brief experimental procedure is stated as follows: SK-MEL-28 melanoma cells were seeded onto the 96-well plate with appropriate seeding density. The cell seeded plate was incubated for 24 hours at 37° C. and 5% $CO_2$ in a standard cell culture incubator before drug treatment. The following day, drug dilutions on either PEGylated solo DOX-L, IMT-L, or DOX/IMT-L liposomal drug combinations at 1:5 or 5:1 molar ratio were prepared using respective cell culture media. The previous cell culture media in the 96-well plate was then replaced by fresh media containing related liposome drugs. After a total of 96 hours of incubation, cell viability was assessed by the MTT assay following the manufacture's protocols. Relative percent survival was determined by subtracting absorbance values obtained by media-only wells from drug treated wells and then normalizing to the no-drug control wells (cell only control). The percentage of cell growth inhibition is calculated by subtracting the % of cell viability from 100%.

As shown in Table 11, the cell growth inhibition capability of PEGylated liposomal DOX/IMT-L at their synergistic ratio (i.e. DOX/IMT=1:5) was significantly greater than what would be expected if each encapsulated drug had contributed in only an additive fashion to its activity. Specifically, cell growth inhibition values of 58.3% for 6.25 µM liposomal DOX-L and 18.2% for 31.25 µM liposomal IMT-L predict a value of cell growth inhibition of 76.5% for liposomal DOX/IMT-L (1:5 molar ratio) (see Table 6), which was dramatically lower than the observed cell growth inhibition value of 96.7%. In addition, the cell growth inhibition of liposomal DOX/IMT-L at their antagonistic molar ratio of 5:1 shows a significantly decreased value (22.8% for DOX/IMT=6.25/1.250 µM) than what can be predicted if each loaded drug had contributed in an additive fashion to its efficacy (58.3% for DOX at 6.25 µM plus 10.1% for IMT at 1.25 µM equals to 68.404). Overall, the above results echo the effect of drug ratios on their efficacy as observed in Example 1 and demonstrate the same synergistic or antagonistic effect based on DOX/IMT ratios when used as free drug solutions can be translated into the dual drug loaded liposome product when the corresponding drug ratios were employed.

TABLE 11

| | In-vitro Analysis on Anti-cancer Activities of PEGylated DOX/IMT-L in SK-MEL-28 Melanoma Cancer Cell Lines | | | | |
| --- | --- | --- | --- | --- | --- |
| | DOX/IMT-L at 1:5 ratio (synergistic) | DOX-L | IMT-L | | DOX/IMT-L at 5:1 ratio (antagonistic) |
| % of cell growth inhibition | 96.7% | 58.3% | 18.2% | 10.1% | 22.8% |
| Dose (μM) | 6.25/31.25 | 6.25 | 31.25 | 1.25 | 6.25/1.25 |

Example 16

In-Vivo Pharmacokinetic Study with DOX/IMT Liposome

In-vivo pharmacokinetic study of free doxorubicin, free imatinib, and DOX/IMT-L (1:5 molar ratio) liposome were carried out in CD-1 mice for a week. The preparation of PEGylated DOX/IMT-L with TEA-SBE-β-CD was described in the Experimental Methods. The free doxorubicin, free imatinib, and PEGylated DOX/IMT-L (molar ratio 1:5) were administered intravenously via the tail vein into CD-1 mice and the plasma DOX/IMT ratio was monitored over time. Doses of the liposomal formulations were 6.0 mg/kg of doxorubicin hydrochloride and 27.3 mg/kg of imatinib mesylate. After intravenous administration, blood was collected at multiple time points for a week by cardiac puncture (3 mice per time point) and placed into EDTA coated micro containers. The samples were centrifuged to separate plasma, and plasma was transferred to another tube. Then, DOX and IMT plasma levels were quantified with LC-MS. The PK parameters calculated from measured DOX and IMT plasma levels in the collect plasma samples after a single intravenous injection.

Based on the PK study results, it can be concluded that the free DOX and free IMT drug solutions were rapidly eliminated, the half-life ($T_{1/2}$) value of the free DOX and free IMT were 0.5 (DOX) and 0.88 hour (IMT), respectively. Comparing to the free drug solutions, the $T_{1/2}$ of PEGylated DOX/IMT-L liposome was extended by >26 (DOX) and >4.3 (IMT) fold. AUC (Area Under Curve) of both drugs in DOX/IMT-L liposome was increased >52 (DOX) and >600 (IMT) fold higher than those in the free drug solutions. MRT (Maximum Retention Time) of both drugs in PEGylated DOX/IMT-L liposome was increased >24 (DOX) and 8 (IMT) fold higher than those in the free drug solutions too. These PK results demonstrated the co-loaded DOX/IMT-L liposome significantly extended the drug retention and exhibits substantially increased plasma drug levels of DOX and IMT in mice comparing to the free drug DOX and IMT. This also indicates both doxorubicin and imatinib in PEGylated DOX/IMT-L have sustained and spontaneous release in blood of mice. In addition, it was also noticed that the DOX/IMT-L liposome drug product was well tolerated at the above-mentioned drug dose by the mice and no adverse event was observed in this PK study.

In addition, from this PK study, the molar ratio of DOX and IMT in plasma could also be determined at different time point. FIG. 20 showed the plot of the molar ratio of DOX/IMT in plasma at first 24 hours after intravenous administration to CD-1 mice. As a result, the molar ratio of DOX and IMT that are encapsulated in the PEGylated liposome was well maintained in the synergistic molar ratios of DOX/IMT at 1:5 to 1:1 as showed in Example 10 for ~20 hours after administration into CD-1 mice when the drugs were simultaneously delivered by the liposomes. Data points represent the molar ratios of DOX:IMT determined in plasma (+/−standard deviation) at the specified time points. As discussed in Example 1, a molar ratio of DOX:IMT above ~1:1 is necessary for the combinational drug to exhibit a synergistic effect in SK-EML-28. Therefore, the appropriately designed liposome drug delivery vehicles demonstrated the delivery of the desired molar ratio of DOX and IMT in CD-1 mice. Moreover, the LC-MS analysis indicated that circulating liposomal drug formulations contained intact drug and no evidence of degradation was observed for either compound.

Example 17

In-Vivo Tumor Regression in Mice Bearing SK-MEL-28 Xenograft Tumors

To maximize the therapeutic activity of drug combinations and to capture the synergistic benefits observed in-vitro, the drug combination needs to be delivered to the tumors site at the optimal drug to drug ratio. For this purpose, the liposome formulations containing DOX and IMT at the fixed ratios known to be synergistic in SK-MEL-28 cells in Example 10 was developed allowing coordinated in-vivo drug release as illustrated in Example 8. The anti-tumor activity of this formulation was then evaluated in SK-MEL-28 melanoma model in-vivo. The PEGylated liposomes co-encapsulated with DOX and IMT at a synergistic molar ratio 1:5 with TEA-SBE-β-CD employed as the trapping agent was used for this study.

In order to perform tumor studies on mice (BALB/c Nude), animals are inoculated subcutaneously at the right flank of the mice with $10 \times 10^6$ SK-MEL-28 tumor cells for tumor development. The inoculated tumor was then allowed to grow for about five weeks prior to initiation of the treatment. Mice were organized into appropriate treatment groups consisting of saline control and drug treated groups including (1) DOX-L (2) DOX/IMT mixed free drug cocktail solution and (3) DOX/IMT-L (DOX:IMT molar ratio of 1:5). Mice were injected intravenously with the required volume of sample to administer the targeted dose (6 mg/kg DOX, 27.3 mg/kg IMT) to the animals based on the weight of each individual mice each week for two weeks. The tumor volume and mice weight are measured and monitored.

As shown in FIG. 21A, in general, the dual drug-loaded liposome (DOX/IMT-L) significantly restrained tumor growth as compared to those observed in the tumor bearing saline control group as well as other drug treated groups including DOX-L monotherapy, IMT-L monotherapy and combination free DOX/IMT cocktail solution. This suppression of the tumor growth is due to the enhanced permeability and retention (EPR) effect of the nanosized liposome formulation, which can improve the drug delivery specificity in the tumor site. Therefore, the comparison on the efficacy between free drug cocktail and liposomal drug combination reflects that the superior biodistribution achieved by the current liposome formulation can lead to more efficient tumor suppression. Compared to other drug treated groups, the DOX-L monotherapy has the similar tumor growth rate as observed in the saline control group, which confirms the intrinsic doxorubicin resistant properties of SK-MEL-28 cell line. Also, the effect on tumor growth inhibition imposed by DOX/IMT-L combination was stronger as compared to that from either DOX-L or IMT-L monotherapies. The result indicates that the synergistic effect between DOX and IMT found from in-vitro studies (Example 10) can be well translated into the liposome formulation in the in-vivo settings. In addition, there is no significant reduction on body weight in all groups investigated in the in-vivo efficacy study (FIG. 21B). Overall, the above results demonstrated that fixing synergistic DOX:IMT molar ratio by encapsulating them inside liposomes can dramatically improve anti-tumor activity.

The foregoing embodiments and examples are provided for illustrative purposes only and are not intended to limit the scope of the invention. Many variations to those described above may be possible. Since various modifications and variations to the embodiments and examples described above will be apparent to those of skill in this art based on the present disclosure, such modifications and variations are within the spirit and scope of the present invention. All patent or non-patent literature cited are incorporated herein by reference in their entireties without admission of them as prior art.

What is claimed is:

1. A pharmaceutical composition comprising liposomes suspended in a liquid medium, wherein the liquid medium comprises water and a pH buffer agent; wherein the liposome comprises an interior compartment surrounded by an outer lipid bilayer membrane, wherein the interior compartment comprises a hydrophilic chemotherapeutic agent, a protein kinase inhibitor, and a trapping agent selected from ammonium or substituted ammonium salts of polyanionized sulfobutyl ether cyclodextrin, ammonium or substituted ammonium salts of polyanionized sulfated carbohydrates, ammonium or substituted ammonium salt of polyphosphate, transition metal salts, quaternary ammonium compounds, polyoxyethylene, and coconut amine, in an aqueous medium; wherein the lipid bilayer membrane comprises a hydrophilic inner surface forming the interior compartment, a lipophilic bilayer, and a hydrophilic outer surface in contact with the liquid medium of the composition; and wherein the hydrophilic chemotherapeutic agent and protein kinase inhibitor can be released from the liposomes in a synergistic mode.

2. The pharmaceutical composition of claim 1, wherein the lipid bilayer membrane comprises (a) at least 10 mol % of a phospholipid selected from the group consisting of phosphatidylcholine, phosphatidylglycerol, phosphatidylinositol, glyceroglycolipids, sphingoglycolipids, and combinations thereof; (b) 0-60 mol % cholesterol, or a derivative thereof; and (c) optionally a charged phospholipid derivatized to polyethylene glycol.

3. The pharmaceutical composition of claim 1, wherein the one or more lipids are independently selected from the group consisting of HSPC, DSPC, DPPC, DMPC, DSPG, mPEG-DSPE-2000, and cholesterol.

4. The pharmaceutical composition of claim 1, wherein the trapping agent is selected from ammonium or substituted ammonium salts of polyanionized sulfobutyl ether cyclodextrin, ammonium or substituted ammonium salts of polyanionized sulfated carbohydrates, ammonium or substituted ammonium salt of polyphosphate, transition metal salts, and quaternary ammonium compounds.

5. The pharmaceutical composition of claim 4, wherein the ammonium or substituted ammonium salts of polyanionized sulfobutyl ether cyclodextrin are selected from TEA-SBE-α-cyclodextrin, TEA-SBE-β-cyclodextrin, TEA-SBE-γ-cyclodextrin, Tris-SBE-α-cyclodextrin, Tris-SBE-β-cyclodextrin and Tris-SBE-γ-cyclodextrin; the ammonium or substituted ammonium salts of polyanionized sulfated carbohydrates are selected from TEA-SOS and Tris-SOS; the ammonium or substituted ammonium salt of polyphosphate is selected from triethylammonium inositol hexaphosphate and tris(hydroxymethyl) aminomethane inositol hexaphosphate; the transition metal salts are selected from salts of copper, zinc, manganese, nickel, cobalt, or the like, with halide, sulfate and gluconate; and the quaternary ammonium compounds are selected from benzalkonium chloride, benzethonium chloride, cetrimonium bromide, and stearyl dimethylbenzyl ammonium chloride.

6. The pharmaceutical composition of claim 1, wherein the outer surface of the lipid bilayer membrane comprises a surface negative charged lipid or a surface-modifying agent containing polyethylene glycol, wherein the molar ratio of the total lipid to the protein kinase inhibitor, or the total amount of the hydrophilic chemotherapeutic agent and protein kinase inhibitor combined when both present, is at least equivalent (1:1).

7. The pharmaceutical composition of claim 1, wherein the chemotherapeutic agent is selected from the group consisting of doxorubicin, cyclophosphamide, carboplatin, paclitaxel, daunorubicin, epirubicin, 5-fluorouracil, gemcitabine, eribulin, ixabepilone, methotrexate, mutamycin, mitoxantrone, vinorelbine, docetaxel, thiotepa, bleomycin, vincristine, dacarbazine, capecitabine, prednisone, camptothecin, topotecan, irinotecan, BCNU, carmustine, cis-platin, lenalidomide, and pemetrexed.

8. The pharmaceutical composition of claim 1, wherein the protein kinase inhibitor is selected from the group consisting of imatinib, sunitinib, afatinib, nintedanib, ponatinib, ruxolitinib, crizotinib, ibrutinib, acalabrutinib, abemaciclib, aflibercept, alectinib, avapritinib, axitinib, bosutinib, cabozantinib, capmatinib, ceritinib, cobimetinib, crizotinib, dabrafenib, dacomitinib, dasatinib, encorafenib, entrectinib, erdafitinib, erlotinib, everolimus, fedratinib, fostamatinib, gefitinib, gilteritinib, ibrutinib, lapatinib, larotrectinib, lenvatinib, lorlatinib, nintedanib, neratinib, nilotinib, netarsudil, osimertinib, pacritinib, pazopanib, pexidartinib, pemigatinib, palbociclib, ponatinib, pexidartinib, pralsetinib, quizartinib, regorafenib, ribociclib, ripretinib, selpercatinib, selumetinib, sorafenib, temsirolimus, tofacitinib, trametinib, tucatinib, upadacitinib, vandetanib, vemurafenib, zanubrutinib, and ziv-aflibercept.

9. The pharmaceutical composition of claim 1, wherein the interior compartment of the liposome comprises an anticancer agent or a combination selected from the group consisting of the following:

(b) doxorubicin and imatinib co-encapsulated;

(d) doxorubicin and sunitinib co-encapsulated;

(f) gemcitabine and sunitinib co-encapsulated;

(g) doxorubicin and imatinib in about 30:1 to about 1:30 molar ratio;

(h) doxorubicin and sunitinib in about 30:1 to about 1:30 molar ratio; and (i) gemcitabine and sunitinib in about 30:1 to about 1:30 molar ratio.

10. The pharmaceutical composition of claim 1, wherein the liposomes have a mean particle size between 4.5 nm and 450 nm, inclusive.

11. The pharmaceutical composition of claim 1, wherein molar ratio of the chemotherapeutic agent and protein kinase inhibitor is such that when said ratio is provided to cancer cells relevant to said cancer in an in-vitro assay over the concentration range at which the fraction of affected cells is about 0.20 to 0.80, synergy is exhibited over at least 20% of said range.

12. The pharmaceutical composition of claim 1, wherein the liposome encapsulated with a chemotherapeutic agent and a protein kinase inhibitor, maintains for at least one hour of the said synergistic molar drug ratio in blood after in-vivo administration.

13. A method of treating a cancer or drug resistance of a cancer, comprising administering to a subject in need of treatment a therapeutically effective amount of a pharmaceutical composition according to claim 1, wherein the cancer is selected from breast cancer, melanoma, gastrointestinal cancer, lung cancer, colorectal cancer, Ewing sarcoma, pancreatic cancer, prostate cancer, bladder cancer, kidney cancer, thyroid cancer, uterine cancer, and gastrointestinal stromal tumors.

14. The method of claim 13, wherein the breast cancer is triple negative breast cancer, and wherein the lung cancer is caused by either a high level of phosphorylation of a wild-type EGFR or a mutation within an EGFR amino acid sequence.

15. A method of preparing a liposomal pharmaceutical composition according to claim 1, wherein the liposome is made by a process comprising the steps of:

(a) forming multilamellar liposome vesicles in a solution comprising water, lipid(s), and trapping agent(s) selected from ammonium or substituted ammonium salts of polyanionized sulfobutyl ether cyclodextrin, ammonium or substituted ammonium salts of polyanionized sulfated carbohydrates, ammonium or substituted ammonium salts of polyphosphate, transition metal salts, quaternary ammonium compounds, polyoxyethylene, and coconut amine;

(b) extruding the multilamellar liposome vesicles multiple times at an elevated temperature through a polycarbonate membrane to form unilamellar liposomes;

(c) substantially removing the trapping agent(s) that are outside of the liposomes by diafiltration or size exclusion chromatography, or other buffer exchanging methods; and (d) heating the unloaded liposomes at an elevated temperature in an aqueous solution comprising a chemotherapeutic agent and a protein kinase inhibitor, thereby forming drug encapsulated liposomes.

16. The method of claim 15, wherein the lipid is selected from the group consisting of: (a) at least 10 mol % of a phospholipid selected from the group consisting of phosphatidylcholine, phosphatidylglycerol, phosphatidylinositol, glyceroglycolipids, sphingoglycolipids, and combinations thereof; (b) 0-60 mol % cholesterol, or a derivative thereof; and (c) optionally a charged phospholipid derivatized to polyethylene glycol.

17. The method of claim 15, wherein the ammonium or substituted ammonium salts of polyanionized sulfobutyl ether cyclodextrin are selected from TEA-SBE-α-cyclodextrin, TEA-SBE-β-cyclodextrin, TEA-SBE-γ-cyclodextrin, Tris-SBE-α-cyclodextrin, Tris-SBE-β-cyclodextrin and Tris-SBE-γ-cyclodextrin; the ammonium or substituted ammonium salts of polyanionized sulfated carbohydrates are selected from TEA-SOS and Tris-SOS; the ammonium or substituted ammonium salts of polyphosphate are selected from triethylammonium inositol hexaphosphate and tris (hydroxymethyl) aminomethane inositol hexaphosphate; the transition metal salts are selected from salts of copper, zinc, manganese, nickel, cobalt, or the like, with halide, sulfate, are gluconate; and the quaternary ammonium compounds are selected from benzalkonium chloride, benzethonium chloride, cetrimonium bromide, and stearyl dimethylbenzyl ammonium chloride.

18. The method of claim 15, comprising a process selected from: active loading, passive loading, and combination thereof; wherein the active or passive loading is selected from:

(a) pH gradient-based active loading method, which encapsulates the chemotherapeutic agent and protein kinase inhibitor based on a transmembrane pH gradient, wherein the pH value of the interior aqueous compartment of the liposome is lower than that outside the liposome;

(b) transition metal-based active loading method, which encapsulates the chemotherapeutic agent and protein kinase inhibitor by utilizing transition metal ions to drive the uptake of the chemotherapeutic agent and protein kinase inhibitor into liposomes via complexation;

(c) passive loading method, which encapsulates the chemotherapeutic agent and protein kinase inhibitor during the liposome formation; and (d) passive loading method, which involves passive equilibration after the formation of liposomes.

19. The method of claim 18, wherein the pH gradient is formed by a concentration gradient of an ammonium ion or a concentration gradient of an organic compound having an ammonium derivative or substituted ammonium capable of being protonated.

20. The method of claim 15, wherein the chemotherapeutic agent is selected from the group consisting of doxorubicin, cyclophosphamide, carboplatin, paclitaxel, daunorubicin, epirubicin, 5-fluorouracil, gemcitabine, eribulin, ixabepilone, methotrexate, mitomycins, mitoxantrone, vinorelbine, docetaxel, thiotepa, bleomycin, vincristine, dacarbazine, capecitabine, prednisone, camptothecin, topotecan, irinotecan, carmustine, cis-platin, BCNU, lenalidomide, and pemetrexed; and wherein the protein kinase inhibitor is selected from the group consisting of imatinib, sunitinib, afatinib, nintedanib, ponatinib, ruxolitinib, crizotinib, ibrutinib, acalabrutinib, abemaciclib, aflibercept, alectinib, avapritinib, axitinib, bosutinib, cabozantinib, capmatinib, ceritinib, cobimetinib, crizotinib, dabrafenib, dacomitinib, dasatinib, encorafenib, entrectinib, erdafitinib, erlotinib, everolimus, fedratinib, fostamatinib, gefitinib, gilteritinib, ibrutinib, lapatinib, larotrectinib, lenvatinib, lorlatinib, nintedanib, neratinib, nilotinib, netarsudil, osimertinib, pacritinib, pazopanib, pexidartinib, pemigatinib, palbociclib, ponatinib, pexidartinib, pralsetinib, quizartinib, regorafenib, ribociclib, ripretinib, selpercatinib, selumetinib, sorafenib, temsirolimus, tofacitinib, trametinib, tucatinib, upadacitinib, vandetanib, vemurafenib, zanubrutinib, ziv-aflibercept, and combinations thereof.

21. The method of claim 15, where the liposomes have a mean particle size in the range of between 4.5 nm and 450 nm, inclusive.

22. A treatment kit comprising a container and a plurality of the drug-loaded liposomes of claim 1 in the container, wherein the drug-loaded liposomes are or can be suspended in a sterile diluent solution ready for administration to a subject in need of treatment.

* * * * *